US008754037B2

(12) United States Patent
Kim et al.

(10) Patent No.: US 8,754,037 B2
(45) Date of Patent: Jun. 17, 2014

(54) MODIFIED HUMAN TUMOR NECROSIS FACTOR RECEPTOR-1 POLYPEPTIDE OR FRAGMENT THEREOF, AND METHOD FOR PREPARING SAME

(75) Inventors: Sung Wuk Kim, Seongnam-si (KR); Sung Soo Jun, Seongnam-si (KR); Seung Kook Park, Seoul (KR); Song Young Kim, Suwon-si (KR); Eun Sun Kim, Suwon-si (KR); Jae Kap Jeong, Suwon-si (KR); Ha Na Kim, Suwon-si (KR); Yeon Jung Song, Yongon-si (KR)

(73) Assignee: Hanall Biopharma Co., Ltd., Daejeon (KR)

(*) Notice: Subject to any disclaimer, the term of this patent is extended or adjusted under 35 U.S.C. 154(b) by 0 days.

(21) Appl. No.: 13/513,803

(22) PCT Filed: Dec. 21, 2011

(86) PCT No.: PCT/KR2011/009914

§ 371 (c)(1), (2), (4) Date: Jun. 4, 2012

(87) PCT Pub. No.: WO2012/087017

PCT Pub. Date: Jun. 28, 2012

(65) Prior Publication Data

US 2012/0277142 A1 Nov. 1, 2012

(30) Foreign Application Priority Data

Dec. 23, 2010 (KR) ........................ 10-2010-0132955

(51) Int. Cl.

| | |
|---|---|
| ***C07K 14/715*** | (2006.01) |
| ***C12N 15/70*** | (2006.01) |
| ***A61K 38/17*** | (2006.01) |
| ***A61P 5/00*** | (2006.01) |
| ***A61P 11/00*** | (2006.01) |
| ***A61P 3/04*** | (2006.01) |
| ***A61P 3/10*** | (2006.01) |
| ***A61P 19/02*** | (2006.01) |
| ***A61P 19/08*** | (2006.01) |
| ***A61P 25/08*** | (2006.01) |
| ***A61P 35/00*** | (2006.01) |
| ***A61P 27/02*** | (2006.01) |
| ***A61K 31/7088*** | (2006.01) |
| ***C07H 21/04*** | (2006.01) |
| ***A61P 41/00*** | (2006.01) |
| ***A61P 29/00*** | (2006.01) |
| ***A61P 1/00*** | (2006.01) |
| ***A61P 25/28*** | (2006.01) |
| ***A61P 1/18*** | (2006.01) |
| ***C12N 1/21*** | (2006.01) |

(52) U.S. Cl.

USPC .................... 514/1.4; 435/252.33; 435/320.1; 514/1.1; 514/1.5; 514/4.8; 514/6.9; 514/16.6; 514/16.7; 514/16.8; 514/17.7; 514/17.9; 514/18.3; 514/19.3; 514/20.8; 514/44 R; 530/350; 536/23.5

(58) Field of Classification Search

None

See application file for complete search history.

(56) References Cited

U.S. PATENT DOCUMENTS 7,144,987 B1 12/2006 Chirino et al.
2004/0170975 A1 9/2004 Savitzky et al.

FOREIGN PATENT DOCUMENTS

EP 2 221 314 A1 8/2010
WO WO 99/41374 * 2/1999
WO WO 2010124262 A1 * 10/2010
WO 2012/036410 A2 3/2012

OTHER PUBLICATIONS

Caminero et al. Clin & Exp Immunology. 338-345:2011.*
Schneider-Brachert et al. Immunity. 21;415-428:2004.*
International Searching Authority, International Search Report issued in corresponding PCT Application No. PCT/KR2011/009914, dated Dec. 21, 2011.

* cited by examiner

*Primary Examiner* — Karlheinz R Skowronek
*Assistant Examiner* — Schuyler Milton
(74) *Attorney, Agent, or Firm* — Sughrue Mion, PLLC

(57) ABSTRACT

Provided is a modified human tumor necrosis factor receptor-1 polypeptide or a fragment thereof that binds to a tumor necrosis factor in vivo or ex vivo. The modified human tumor necrosis factor receptor-1 polypeptide or fragment exhibits improved ability to bind tumor necrosis factor and resistance to proteases.

24 Claims, 12 Drawing Sheets

** P<0.01, Comparison with vehicle group

# P<0.05, Comparison with Enbrel group

** P<0.01, Comparison with vehicle group

MODIFIED HUMAN TUMOR NECROSIS FACTOR RECEPTOR-1 POLYPEPTIDE OR FRAGMENT THEREOF, AND METHOD FOR PREPARING SAME

CROSS REFERENCE TO RELATED APPLICATION

This application is a National Stage of International Application No. PCT/KR2011/009914 filed Dec. 21, 2011, claiming priority based on Korean Patent Application No. 10-2010-0132955 filed Dec. 23, 2010, the contents of all of which are incorporated herein by reference in their entirety.

TECHNICAL FIELD

The present invention relates to a modified human tumor necrosis factor receptor-I polypeptide or a fragment thereof which is capable of binding to a tumor necrosis factor in vivo or ex vivo and a method for producing the same.

BACKGROUND ART

Inflammation is the body's defense response which is induced by antigenic stimulation. An inflammatory response may worsen pathologically when inflammation takes place even after the removal of injurious antigenic substances or an inflammatory response is induced by an inappropriate stimulus such as an auto-antigen. Such an inflammatory response involves a variety of cytokines. In particular, as a cytokine which serves to control inflammation, a tumor necrosis factor (hereinafter, referred to as "TNF") was identified.

TNF was originally discovered as a protein which eliminates tumor cells (Carswell et al., PNAS 72:3666-3670, 1975). TNF is a class of cytokines produced by numerous cell types, including monocytes and macrophages, and is directly involved in inflammatory responses. At least two TNFs (TNF-$\alpha$ and TNF-$\beta$) have been previously described, and each is active as a trimeric molecule and is believed to initiate intracellular signaling by crosslinking receptors (Engelmann et al., J. Biol. Chem., 265:14497-14504). TNFs induce inflammatory responses in vivo to regulate cell-mediated immune responses and defense mechanisms and have important physiological effects on a number of different target cells (Selby et al., Lancep 1:483, 1988). However, it was demonstrated that an excess of TNFs results in a pathological condition such as rheumatoid arthritis, degenerative arthritis, psoriasis or Crohn's disease, and suppression of TNFs exhibits therapeutic effects on the diseases (Feldmann et al., Nat. Med. 9:1245-1250, 2003).

Tumor necrosis factor receptor (hereinafter, referred to as "TNFR") is a cytokine receptor which binds to TNF.

Two types of TNFRs, known as p55-TNFRI and p75-TNFRII, have been currently discovered. Expression of TNFRI can be demonstrated in almost every mammalian cell while TNFRII expression is largely limited to cells of the immune system and endothelial cells.

The two TNF receptors exhibit 28% amino acid sequence similarity therebetween. Both receptors have an extracellular domain and have four cysteine-rich domains.

The cytoplasmic portion of TNFRI contains a "death domain" which initiates apoptotic signaling. TNFRII has no death domain and the function thereof has not been yet clearly defined. In addition, TNFRI and TNFRII exhibit a difference in terms of affinity for TNF-$\alpha$ which is a ligand. It is known that TNFRI exhibits an affinity 30 times or higher than that of TNFRII (Tartaglia et al., J. Biol. Chem. 268:18542-18548, 1993). Due to such affinity difference, a variety of attempts have been made for the development of pharmaceuticals regarding TNFRI.

TNFR adhering to the cell surface is cleaved by protease to produce soluble TNFR. The soluble TNFR neutralizes an excess of TNF to control the level of TNF. In cases such as autoimmune disease and chronic inflammation excessively high levels of TNF overwhelms the ability to self-regulate.

In order to artificially control TNF signaling, various strategies of blocking TNF have been attempted including inhibition of TNF synthesis, inhibition of TNF secretion or shedding, and inhibition of TNF signaling. Among TNF blocking methods, a method of blocking TNF signaling by preventing binding of TNFR to TNF has been applied for the development of pharmaceuticals. For example, etanercept, which is prepared by fusing a TNFRII extracellular region to the Fc region of an antibody, and antibodies capable of binding to TNF, adalimumab and infliximab have been used globally as a therapeutic agent for treating rheumatoid arthritis, psoriasis, ankylosing spondylitis, or the like.

Lenercept, which is a fusion protein of an antibody Fc to a TNFRI extracellular domain produced by applying the same technique as in the anti-rheumatoid arthritis drug etanercept, has completed a phase II clinical trial in Europe and USA (Furst et al., J. Rheumatol. 30:2123-2126, 2003). In addition, research has been carried out for a TNFRI dimer and a pegylated soluble TNFRI molecule (Carl et al., Ann. Rheum. Dis. 58:173-181, 1999).

Further, as an approach to reduce immunogenicity of TNFRI and increase the ability of TNFRI to bind with TNF, modification of amino acid sequences has been studied. In particular, a TNFRI mutant, against which the occurrence of an antibody has been decreased through partial substitution of the amino acid sequence of TNFRI, and a TNFRI mutant, which has an increased ability of TNFRI to bind with TNF, are known (U.S. Pat. No. 7,144,987).

Research has been actively made to find an active site responsible for binding of TNFR to TNF, and it is known that the fourth domain of TNFR is not essential for binding with TNF, and when deletion of the second and third domains results in loss of TNF binding activity (Corcoran et al., Eur. J. Biochem. 233:831-840, 1994). Further, a certain region of the third domain for binding of TNFRI to TNF may be made deficient, and the amino acid sequence consisting of amino acid residues 59 to 143 of a human TNFRI polypeptide (SEQ ID NO: 1) is known to be a region showing a biological activity of TNFRI (U.S. Pat. No. 6,989,147).

Therefore, since binding of TNFRI to TNF is made in this region, other regions may include considerable added groups, eliminated groups or substituted groups. Meanwhile, in order to enhance bioavailability, TFNRI is used in the form of a TNFRI polypeptide fragment rather than full-length TNFRI. For the purpose of producing an effective injection and oral formulation capable of minimizing protease cleavability and enhancing cellular permeability, TFNRI needs to be prepared as small in size as possible.

Since protein therapeutics are cleared by general processes such as metabolism during in vivo circulation, glomerular filtration, and action of proteases in gastrointestinal tracts, tissues and blood, there is difficulty in delivery of a protein therapeutic to a target site while retaining an intrinsic activity of the protein in vivo. In particular, clearance of a drug by protease has significant effects on a half-life of a protein therapeutic upon administration thereof via oral administration, vascular injection, intramuscular injection, or the like.

A human tumor necrosis factor inhibitor, which is one of protein therapeutic drugs and controls in vivo TNF, has been developed in the form of an injection, but the administration of an injection has problems associated with pain and risk of infection. Therefore, another approach is required such as reduction of injection frequency or oral administration. Enhancement of stability of a human tumor necrosis factor inhibitor is essential for this purpose, but protease-induced degradation constitutes a great obstacle thereto.

Meanwhile, while wild-type TFNRI regulates intracellular actions of TNF-α via binding with TNF-α, the binding ability of TNFRI is not as high as that of antibodies. Thus, wild-type TNFRI is poorer at inhibiting TNF-α than are the antibodies. The development of protein therapeutics using TNFRI requires the selection of a TNFRI capable of strongly coupling with TNF-α.

Therefore, one of the main goals in the development of protein therapeutics is to improve the biological activity and resistance to proteases.

This subject was conducted as part of a program for the development of industrial original technology (subject ID No. 10040233) with the support of the Korea Evaluation Institute of Industrial Technology, the Ministry of Knowledge Economy of the Korean Government

DISCLOSURE

Technical Problem

The object of the present invention is to provide a modified human tumor necrosis factor receptor-I (TNFRI) polypeptide or a fragment thereof, which has increased binding ability to TNF in vivo or ex vivo as well as improved resistance to proteases present in the gastrointestinal tract, cytoplasm and blood.

Technical Solution

Unless stated otherwise, all technical and scientific terms used in the specification, examples and appended claims have the meanings defined below.

As used herein, the term "human tumor necrosis factor receptor-I" or "human tumor necrosis factor receptor-I polypeptide" (hereinafter, referred to as "TNFRI" or "TNFRI polypeptide") refers to a polypeptide consisting of 455 amino acids derived from a human and capable of binding to TNF.

As used herein, the term "human tumor necrosis factor receptor-I fragment" or "human tumor necrosis factor receptor-I polypeptide fragment" (hereinafter, referred to as "TNFRI fragment" or "TNFRI polypeptide fragment") refers to a fragment of TNFRI which has an amino acid sequence 100% identical to a corresponding amino acid sequence of full length TNFRI and which shows a deletion of at least one amino acid residue of the TNFRI. The deleted amino acid residue(s) may be located at any position of the polypeptide, such as the N-terminus, the C-terminus, or in between these. The fragment shares at least one biological property with full-length TNFRI. Representative is a fragment consisting of a 105- or 126- or 171-amino acid sequence extending from amino acid residue 41 of the N-terminus of TNFRI, each herein being designated as TNFRI105, TNFRI126 and TNFRI 171, respectively.

As used herein, the term "TNFRI variant" or "TNFRI mutant" or "TNFRI fragment variant", "TNFRI fragment mutant" or "modified TNFRI polypeptide", or "modified TNFRI polypeptide fragment" refers to a TNFRI polypeptide or a fragment thereof which shares a sequence identity of less than 100% with the TNFRI polypeptide or TNFRI fragment isolated from the native or recombinant cells as defined below. Typically, the TNFRI mutant has an amino acid sequence identity of approximately 70% or higher with a wild-type or native TNFRI or TNFRI fragment. The sequence identity is preferably at least approximately 75%, more preferably at least approximately 80%, still more preferably at least approximately 85%, even more preferably at least approximately 90%, and most preferably at least approximately 95%.

As used herein, the term "quadruple mutant" refers to a mutant with mutations at four positions in the amino acid sequence of a human tumor necrosis factor receptor-I or human tumor necrosis factor receptor-I fragment.

As used herein, the term "quintuple mutant" refers to a mutant with mutations at five positions in the amino acid sequence of a human tumor necrosis factor receptor-I or human tumor necrosis factor receptor-I fragment.

As used herein, the term "sextuple mutant" refers to a mutant with mutations at six positions in the amino acid sequence of a human tumor necrosis factor receptor-I or human tumor necrosis factor receptor-I fragment.

As used herein, the term "septuple mutant" refers to a mutant with mutations at seven positions in the amino acid sequence of a human tumor necrosis factor receptor-I or human tumor necrosis factor receptor-I fragment.

As used herein, the term "TNFRIm" refers to a TNFRI fragment having an amino acid sequence consisting of an m number of amino acids extending from amino acid residue 41 of the N-terminus of the amino acid sequence of TNFRI. For example, the TNFRI105 fragment refers to a TNFRI fragment having a 105-amino acid sequence extending from amino acid residue 41 of the TNFRI N-terminus. Another example is TNFRI126 that has a 126-amino acid sequence extending from amino acid residue 41 of the TNFRI N-terminus.

As used herein, the term "Met-TNFRIm" refers to a TNFRI fragment having an amino acid sequence consisting of an m number of amino acids extending from amino acid residue 41 of the TNFRI N-terminus in which methionine originally absent in TNFRI amino acid sequence has been added to the N-terminus for the purpose of expression of TNFRI in *E. coli.*

The amino acids that occur in the various sequences of amino acids provided herein are identified according to their known, three- or one-letter abbreviations. The nucleotides which occur in the various nucleic acid fragments are designated by the standard single-letter designations used routinely in the art.

The symbol "xAz," as used herein refers to the substitution of amino acid x at position A with amino acid z in the amino acid sequence. For example, K48Q refers to a glutamine (Gln) residue substituted for a lysine (Lys) residue at position 48.

The present invention relates to a modified TNFRI polypeptide or a fragment thereof having increased ability to bind with TNF-α in vivo and/or ex vivo as well as improved protease resistance, a method for producing the same, and use thereof.

Leading to the present invention, intensive and thorough research into TNFR1 mutants with improved affinity for TNF and in in vivo and/or in vitro stability conducted by the present inventors, resulted in the finding that substitution at four or more amino acid residues within the TNFRI site to which TNF is expected to bind elicits an improvement in the affinity for TNF. However, because resultant mutants having increased affinity for TNF were susceptible to enzymatic degradation, additional modification(s) to increase protease resistance was(were) added to the mutants to select mutant(s) having protease resistance similar or higher than native TNFRI.

Therefore, the present invention provides a modified TNFRI polypeptide or a fragment thereof that has improved ability to bind with TNF as well as protease resistance, by substituting amino acids at five or more positions in specific sites of the amino acid sequence of native TNFRI.

Stably bound to TNF, the modified TNFRI polypeptides or fragments thereof in accordance with the present invention can effectively inhibit actions of TNF. In addition, they can be prepared in microbial cells as well as animal cells because their activity is independent of modification with a sugar chain.

A more detailed description will be given of the present invention, below.

The present invention provides modified tumor necrosis factor receptor-1 (TNFRI) or a fragment thereof, comprising modifications of 5 amino acid residues consisting of 4 amino acid residues at positions 92, 95, 97 and 98, and 1 amino acid residue at one selected from among positions 68, 161, 200 and 207 in the amino acid sequence of a wild-type TNFRI polypeptide represented by SEQ ID NO: 1 or a functionally active fragment thereof, whereby said modified TNFRI polypeptide or fragment has improved ability to bind to TNF compared to the wild-type human tumor necrosis factor receptor-1 (TNFRI) polypeptide and protease resistance comparable or higher than the wild-type human tumor necrosis factor receptor-1 (TNFRI) polypeptide.

The present invention also provides a modified tumor necrosis factor receptor-1 (TNFRI) or a fragment thereof, comprising a further amino acid modification at position 93 in the amino acid sequence of a wild-type TNFRI polypeptide represented by SEQ ID NO: 1 or a functionally active fragment thereof, in addition to the modifications of 5 amino acid residues consisting of 4 amino acid residues at positions 92, 95, 97 and 98, and 1 amino acid residue at one selected from among positions 68, 161, 200 and 207.

Preferably, the present invention provides a modified tumor necrosis factor receptor-1 (TNFRI) or a fragment thereof, comprising modifications of amino acid residues at positions 68, 92, 95, 97 and 98 in the amino acid sequence of a wild-type TNFRI polypeptide represented by SEQ ID NO: 1 or a functionally active fragment thereof. Furthermore, the present invention provides a modified tumor necrosis factor receptor-1 (TNFRI) or a fragment thereof, comprising a further modification of an amino acid residue at position 161 or 207 in the amino acid sequence of a wild-type TNFRI polypeptide represented by SEQ ID NO: 1 or a functionally active fragment thereof, in addition to modifications amino acid residues at positions 68, 92, 95, 97, and 98.

The present invention provides a modified tumor necrosis factor receptor-1 (TNFRI) or a fragment thereof, comprising modifications of 6 amino acid residues consisting of 4 amino acid residues at positions 92, 95, 97 and 98, and 2 amino acid residues at two selected from among positions 68, 161, 200 and 207 in the amino acid sequence of a wild-type TNFRI polypeptide represented by SEQ ID NO: 1 or a functionally active fragment thereof.

The modification is intended to bring about an improvement in ability to bind to TNF as well as to guarantee the same or higher resistance to proteases compared to the wild-type TNFRI polypeptide or its fragment. Representative is amino acid substitution. However, so long as it provides the increased binding ability and the equivalent or improved resistance to enzymatic degradation, any modification may be used in the present invention, including chemical modifications on amino acid residues at the same positions, such as post-translational modifications, among which are glycosylation with carbohydrate moiety, acylation (e.g., acetylation or succinylation), methylation, phosphorylation, hasylation, carbamylation, sulfation, prenylation, oxidation, guanidination, amidination, carbamylation (e.g., carbamoylation), trinitrophenylation, nitration, and PEGylation.

In the case of the modification of an amino acid substitution on the amino acid sequence of a wild-type human tumor necrosis factor-1 (TNFRI) polypeptide represented by SEQ ID NO:1 or a functionally active fragment thereof, L at position 68 is substituted with V; S at position 92 with I, L, F, M, W, Q, T, Y, K, H, E, A, V, P, N or R; E at position 93 with P; H at position 95 with F; R at position 97 with P, L or I; H at position 98 with A or G; K at position 161 with Q or N; E at position 200 with Q; and D at position 207 with N. Preferably, S at position 92 is substituted with I, M or H; R at position 97 with P.

More preferably, the present invention provides a modified human tumor necrosis factor receptor-1 or a fragment thereof, comprising an amino acid modification selected from the group consisting of L68V/S92I/H95F/R97P/H98A, L68V/S92M/H95F/R97P/H98A, L68V/S92H/H95F/R97P/H98A, L68V/S92I/H95F/R97P/H98G, L68V/S92M/H95F/R97P/H98G, L68V/S92I/H95F/R97P/H98A/K161Q, L68V/S92I/H95F/R97P/H98A/K161N, L68V/S92I/H95F/R97P/H98A/D207N, L68V/S92M/H95F/R97P/H98A/K161Q, L68V/S92M/H95F/R97P/H98A/K161N, L68V/S92M/H95F/R97P/H98A/D207N, L68V/S92H/H95F/R97P/H98A/K161Q, L68V/S92H/H95F/R97P/H98A/K161N, L68V/S92H/H95F/R97P/H98A/D207N, L68V/S92I/H95F/R97P/H98G/K161Q, and L68V/S92M/H95F/R97P/H98G/K161N in the amino acid sequence of a wild-type human TNFRI polypeptide or a functionally active fragment thereof, represented by SEQ ID NO: 1.

As used herein the term "functionally active fragment" of the wild-type human TNFRI polypeptide set forth in the amino acid sequence of SEQ ID NO: 1, means a part of the wild-type human TNFR1 polypeptide that performs substantially the same functions as those of the intact polypeptide. In particular, the present invention employs an amino acid sequence consisting of amino acid residues 41-211 (SEQ ID NO: 2; TNFRI171) of the amino acid sequence of native human TNFRI as set forth in SEQ ID NO: 1; an amino acid sequence consisting of amino acid residues 41-166 (SEQ ID NO: 3; TNFRI126) of the amino acid sequence of native human TNFRI as set forth in SEQ ID NO: 1; and an amino acid sequence consisting of amino acid residues 41-145 (SEQ ID NO: 4; TNFRI105) of the amino acid sequence of native human TNFRI as set forth in SEQ ID NO: 1. For reference, it is well known that a fragment extending from position 59 to position 143 in the amino acid sequence of human TNFRI polypeptide (SEQ ID NO: 1) exhibits the biological activity of TNFRI (U.S. Pat. No. 6,989,147).

As used herein, the term "fragment" of the modified TNFRI polypeptide refers to a part of the modified TNFRI polypeptide which has substantially the same effect as that of the modified TNFRI polypeptide and which can be readily prepared by those skilled in the art.

Within the scope of the modified TNFR1 polypeptide and the fragment thereof that is improved in affinity for TNF and has the same or improved resistance to proteases, those described below are included.

The present invention provides a modified human tumor necrosis factor receptor-1 polypeptide or a fragment thereof, having an amino acid sequence consisting of amino acids 41-211 of the amino acid sequence of wild-type human tumor necrosis factor receptor-1 polypeptide, represented by SEQ ID NO: 1, with amino acid substitutions of L at position 68 with V; S at position 92 with I, L, F, M, W, Q, T, Y, K, H, E, A, V, P, N or R; H at position 95 with F; R at position 97 with P, L or I; and H at position 98 with A or G. More preferably, the present invention provides a modified human tumor necrosis factor receptor-1 polypeptide or a fragment thereof, having an amino acid sequence consisting of amino acids 41-211 of the amino acid sequence of wild-type human tumor necrosis factor receptor-1 polypeptide, represented by SEQ ID NO: 1, with a modification selected from among L68V/S92I/H95F/R97P/H98A, L68V/S92M/H95F/R97P/H98A, L68V/S92H/H95F/R97P/H98A, L68V/S92I/H95F/R97P/H98G and L68V/S92M/H95F/R97P/H98G.

Also, the present invention provides a modified human tumor necrosis factor receptor-1 polypeptide or a fragment thereof, having an amino acid sequence consisting of amino acids 41-211 of the amino acid sequence of wild-type human tumor necrosis factor receptor-1 polypeptide, represented by SEQ ID NO: 1, with an amino acid substitution of K at position 161 with Q or N, or D at position 207 with N, in addition to the above-mentioned substitutions. The modified human tumor necrosis factor receptor-1 polypeptide or a fragment thereof of the present invention contains a modification selected from among L68V/S92I/H95F/R97P/H98A/K161Q, L68V/S92I/H95F/R97P/H98A/K161N, L68V/S92I/H95F/R97P/H98A/D207N, L68V/S92M/H95F/R97P/H98A/K161Q, L68V/S92M/H95F/R97P/H98A/K161N, L68V/S92M/H95F/R97P/H98A/D207N, L68V/S92H/H95F/R97P/H98A/K161Q, L68V/S92H/H95F/R97P/H98A/K161N, L68V/S92H/H95F/R97P/H98A/D207N, L68V/S92I/H95F/R97P/H98G/K161Q, and L68V/S92M/H95F/R97P/H98G/K161N.

The present invention provides a modified human tumor necrosis factor receptor-1 polypeptide or a fragment thereof, having an amino acid sequence consisting of amino acids 41-166 of the amino acid sequence of wild-type human tumor necrosis factor receptor-1 polypeptide, represented by SEQ ID NO: 1, with amino acid substitutions of L at position 68 with V; S at position 92 with I, L, F, M, W, Q, T, Y, K, H, E, A, V, P, N or R; H at position 95 with F; R at position 97 with P, L or I; and H at position 98 with A or G. More preferably, the present invention provides a modified human tumor necrosis factor receptor-1 polypeptide or a fragment thereof, having an amino acid sequence consisting of amino acids 41-166 of the amino acid sequence of wild-type human tumor necrosis factor receptor-1 polypeptide, represented by SEQ ID NO: 1, with a modification selected from among L68V/S92I/H95F/R97P/H98A, L68V/S92M/H95F/R97P/H98A, L68V/S92H/H95F/R97P/H98A, L68V/S92I/H95F/R97P/H98G and L68V/S92M/H95F/R97P/H98G.

Also, the present invention provides a modified human tumor necrosis factor receptor-1 polypeptide or a fragment thereof, having an amino acid sequence consisting of amino acids 41-166 of the amino acid sequence of wild-type human tumor necrosis factor receptor-1 polypeptide, represented by SEQ ID NO: 1, with an amino acid substitution of K at position 161 with Q or N in addition to the above-mentioned substitutions. The modified human tumor necrosis factor receptor-1 polypeptide or a fragment thereof of the present invention contains a modification selected from among L68V/S92I/H95F/R97P/H98A/K161Q, L68V/S92I/H95F/R97P/H98A/K161N, L68V/S92M/H95F/R97P/H98A/K161Q, L68V/S92M/H95F/R97P/H98A/K161N, L68V/S92H/H95F/R97P/H98A/K161Q, L68V/S92H/H95F/R97P/H98A/K161N, L68V/S92I/H95F/R97P/H98G/K161Q, and L68V/S92M/H95F/R97P/H98G/K161N.

The present invention provides a modified human tumor necrosis factor receptor-1 polypeptide or a fragment thereof, having an amino acid sequence consisting of amino acids 41-145 of the amino acid sequence of wild-type human tumor necrosis factor receptor-1 polypeptide, represented by SEQ ID NO: 1, with amino acid substitutions of L at position 68 with V; S at position 92 with I, L, F, M, W, Q, T, Y, K, H, E, A, V, P, N or R; H at position 95 with F; R at position 97 with P, L or I; and H at position 98 with A or G. More preferably, the present invention provides a modified human tumor necrosis factor receptor-1 polypeptide or a fragment thereof, having an amino acid sequence consisting of amino acids 41-145 of the amino acid sequence of wild-type human tumor necrosis factor receptor-1 polypeptide, represented by SEQ ID NO: 1, with a modification selected from among L68V/S92I/H95F/R97P/H98A, L68V/S92M/H95F/R97P/H98A, L68V/S92H/H95F/R97P/H98A, L68V/S92I/H95F/R97P/H98G and L68V/S92M/H95F/R97P/H98G.

In addition, the present invention provides a modified human tumor necrosis factor receptor-1 polypeptide or a fragment thereof, having an amino acid sequence sharing a sequence homology of at least 90%, at least 95%, at least 96%, at least 97%, at least 98% or at least 99% with that of the wild-type human TNFRI, represented by SEQ ID NO: 1, with modifications at positions corresponding to positions 68, 92, 95, 97 and 98 of the amino acid sequence of SEQ ID NO: 1. In one embodiment, the modification is amino acid substitution of L with V; S with I, L, F, M, W, Q, T, Y, K, H, E, A, V, P, N or R; H with F; R with P, L or I; and H with A or G at respective positions corresponding to positions 68, 92, 95, 97 and 98 of the amino acid sequence of SEQ ID NO: 1. The modified human tumor necrosis factor-1 polypeptide or the fragment thereof may further comprise an amino acid substitution of K with Q or N; or D with N at respective positions corresponding to positions 161 and 207 of the amino acid sequence of SEQ ID NO: 1.

Also, the present invention provides a modified TNFRI polypeptide or a fragment thereof, having an amino acid sequence substantially identical to that of SEQ ID NO: 1, with the above-mentioned or corresponding amino acid modifications imposed thereon. As used herein, the term "a polypeptide having an amino acid sequence substantially identical to that of SEQ ID NO: 1" means a TNFRI polypeptide having an amino acid modification, such as amino acid substitution, deletion, addition, in such a number and kind as not to detract from its inherent TNFRI activity. More particularly, the present invention provides a modified TNFRI polypeptide or a fragment thereof, having an amino acid sequence sharing a sequence homology of at least 90%, at least 95%, at least 96%, at least 97%, at least 98% or at least 99% with that of SEQ ID NO: 1, with a modification corresponding to the above-mentioned amino acid modification.

The above-mentioned variant has sequence homology of more than 90%, more than 95%, more than 96%, more than 97%, more than 98%, or more than 99% with a polypeptide having the sequence as set forth in SEQ ID NO: 1, except the above-mentioned amino acid modifications of the present invention, and includes allelic variant isoforms of human TNFRI polypeptide, tissue-specific isoforms and allelic variants thereof, synthetic variants with one or more amino acid mutations, replacements, deletions, insertions or additions, synthetic molecules prepared by translation of nucleic acids, proteins isolated from human and non-human tissue and cells, chimeric TNFRI polypeptides and modified forms thereof.

As used herein, the term "corresponding modification" refers to a modification of residues compared among or between polypeptides that are other isoforms. That is, the "corresponding modification" means a modification corresponding to the amino acid modification of the present invention for improving binding ability, and maintaining or dimproving resistance to protease at the position having a residue identified to be functionally unchangeable upon sequence alignment with the amino acid sequence of a native human TNFRI polypeptide as set forth in SEQ ID NO: 1. Those skilled in the art can readily identify modifications of residues that correspond between or among such polypeptides. For example, by aligning the sequences of TNFRI polypeptides, one of skill in the art can identify corresponding residues, using conserved and identical amino acid residues as guides.

Preferably, the present invention provides a TNFRI polypeptide or a fragment thereof containing the amino acid sequence represented by any one of SEQ ID NOS:6, 11, 16, 21, 22, 28-39, 44, 49, 54, 55, 61-72, 75, 78, 81, 82 or 86-98.

The modified TNFRI polypeptide or a fragment thereof in accordance with the present invention may further contain other chemical modifications such as post-translational modifications of a protein, for example, glycosylation by a carbohydrate moiety, acylation (e.g., acetylation or succinylation), methylation, phosphorylation, hesylation, carbamylation, sulfation, prenylation, oxidation, guanidination, amidination, carbamylation (e.g., carbamoylation), trinitrophenylation, nitration, and PEGylation, for the purpose of increasing protease resistance, decreasing immunogenicity, or maintaining or enhancing biological activity, in addition to the above-mentioned amino acid modifications.

In accordance with another aspect thereof, the present invention provides a multimeric polypeptide (or "polypeptide complex") comprising two or more copies of the modified human TNFRI polypeptide or the fragment thereof.

Further, the present invention provides a gene encoding the foregoing TNFRI polypeptide or a fragment thereof.

The gene encoding a TNFRI polypeptide or a fragment thereof in accordance with the present invention includes a gene engineered for optimization of the expression in *E. coli*. Due to the difference in gene codon between human and *E. coli*, when a human gene is expressed in *E. coli*, an expression yield of the gene is low. For this reason, a gene engineered to be suitable for the expression in *E. coli* based on a human TNFRI gene, for example the TNFRI gene of SEQ ID NO: 5 may be used in the present invention. Such a gene exhibits a higher expression level than a human TNFRI gene, when it is inserted into an *E. coli* expression vector (for example, pET44a (Cat. No: 71122-3, Novagen)) and then expressed in an *E. coli* cell with no addition of codon (e.g.: BL21(DE3)). Therefore, using the above gene, a TNFRI fragment and a TNFRI mutant may be efficiently produced in *E. coli*.

Further, the present invention provides a vector containing the same gene. The vector that can be used for the introduction of a gene in the present invention may be a vector known in the art, preferably a vector having a cleavage map of FIG. 1.

Further, the present invention provides a cell (microbial or animal cell) transformed with the vector. The microbial or animal cell that can be used for the transformation of a vector in the present invention may be a known microbial or animal cell for transformation used in the art, preferably an *E. coli* cell, a CHO cell, or an HEK293 cell, and more preferably an *E. coli* cell (for example, *E. coli* BL21(DE3)).

The present invention provides a method for producing TNFRI using *E. coli*.

TNFRI may be produced by using an animal cell (Bernie et al., The Journal of Pharmacology and Experimental Therapeutics. 301: 418-426, 2002; and Scallon et al., Cytokine. 7:759-770, 1995).

Since when it is expressed in *E. coli*, TNFRI is expressed in the form of an inclusion body which is not conformationally active, a process of refolding into an active protein is required (Silvia et al., Analytical Biochemistry 230: 85-90, 1995; and Karin et al., Cytokine. 7:26-38, 1995). Therefore, the modified TNFRI polypeptide or a fragment thereof in accordance with the present invention may be produced by expressing TNFRI in the form of an inclusion body in *E. coli*, refolding the expressed TNFRI into active TNFRI, and purifying the active TNFRI by using gel filtration chromatography or the like. Alternatively, the modified TNFRI polypeptide or a fragment thereof in accordance with the present invention may be produced in the form of a soluble protein instead of an inclusion body in *E. coli*, using an expression method involving attachment of a hydrophilic fusion protein, a low-temperature culture method, or the like. As an example, TNFRI as a soluble protein is produced in *E. coli* by linking a hydrophilic NusA protein to the N-terminus of a TNFRI protein.

Further, the present invention provides a method for producing a TNFRI polypeptide or a fragment thereof, including introducing the gene into a suitable vector, transforming the vector into a host cell to give a transformant, and culturing the transformant in a medium to express the TNFRI polypeptide or a fragment thereof.

Further, the present invention provides a method for the treatment of a TNF-mediated disease or internal symptom (hereinafter, referred to as "TNF-mediated disease"). Examples of the TNF-mediated disease, the related sequelae and symptoms associated therewith include: adult respiratory distress syndrome; anorexia; cancer (e.g., leukemia); chronic fatigue syndrome; graft-versus-host rejection; hyperalgesia; inflammatory bowel disease; neuroinflammatory disease; ischemic/reperfusion injury, including cerebral ischemia (brain injury as a result of trauma, epilepsy, hemorrhage or stroke, each of which may lead to neurodegeneration); diabetes (e.g., juvenile onset Type 1 diabetes mellitus); multiple sclerosis; ocular diseases; pain; pancreatitis; pulmonary fibrosis; rheumatic diseases (e.g., rheumatoid arthritis, osteoarthritis, juvenile (rheumatoid) arthritis, seronegative polyarthritis, ankylosing spondylitis, Reiter's syndrome and reactive arthritis, psoriatic arthritis, enteropathic arthritis, polymyositis, dermatomyositis, scleroderma, systemic sclerosis, vasculitis, cerebral vasculitis, Sjogren's syndrome, rheumatic fever, polychondritis and polymyalgia rheumatica and giant cell arteritis); septic shock; radiotherapy-induced side effects; systemic lupus erythematous; temporomandibular joint disease; thyroiditis and tissue transplantation. The TNF-mediated diseases are well known in the art.

Further, the present invention provides a composition for the prevention or treatment of rheumatoid arthritis or TNF-mediated disease, containing the modified TNFRI polypeptide or a fragment thereof.

Further, the present invention provides a composition for the prevention or treatment of rheumatoid arthritis or TNF-mediated disease, containing a gene encoding the modified TNFRI polypeptide or a fragment thereof, a vector containing the gene or a microbial or animal cell transformed with the vector.

Further, the present invention provides a method of preventing or treating rheumatoid arthritis or TNF-mediated disease, comprising administering the composition for the prevention or treatment of the TNF-mediated disease to a subject in need thereof.

The pharmaceutical composition of the present invention may be administered orally, sublingually, rectally, transdermally, subcutaneously, intramuscularly, intraperitoneally, intravenously or intra-arterially. The pharmaceutical composition may be prepared for storage or administration by mixing a TNFRI mutant having desired purity with pharmaceutically acceptable carriers, excipients or stabilizers.

Acceptable carriers, excipients or stabilizers are nontoxic to recipients in the dosages and concentrations employed, and include buffers such as phosphate, citrate, acetate and other organic acid salts; antioxidants such as ascorbic acid; low-molecular weight (less than about 10 residues in length) peptides including polyarginine and proteins such as serum albumin, gelatin or immunoglobulin; hydrophilic polymers such as polyvinylpyrrolidone; amino acids such as glycine, glutamic acid, aspartic acid or arginine; and other carbohydrates including monosaccharides, disaccharides, cellulose and derivatives thereof, glucose, mannose or dextrins; chelating agents such as EDTA; sugar alcohols such as mannitol or sorbitol; counterions such as sodium; and/or non-ionic surfactants such as Tween, Pluronics or polyethylene glycol (PEG).

The pharmaceutical composition of the present invention may be formulated in the form of a sterile composition for injection according to a conventional method known in the art. The sterile composition for injection may contain a solution or suspension of the active compound in a vehicle such as water or naturally occurring vegetable oil like sesame, peanut or cottonseed oil or a synthetic fatty vehicle like ethyl oleate. The sterile composition for injection may be incorporated into a buffer, a preservative, an antioxidant and the like according to an accepted pharmaceutical practice.

A modified TNFRI polypeptide or a fragment thereof, or a gene encoding the same, or a vector containing the same gene, or a microbial or animal cell transformed with the vector in accordance with the present invention is incorporated in a therapeutically effective amount for the TNF-mediated disease in a pharmaceutical composition.

As used herein, the term "therapeutically effective amount" refers to the amount/dose of an active ingredient or pharmaceutical composition that is sufficient to elicit an effective response (i.e., a biological or medical response of an animal or human sought by a researcher, veterinarian, medical doctor or other clinician) upon administration to a subject. The therapeutically effective amount is intended to encompass an amount to produce symptomatic alleviation of the disease or disorder being treated. It is apparent to those skilled in the art that the therapeutically effective amount and dosing frequency of the active ingredient of the present invention will vary depending on desired effects. Therefore, an optimum dosage can be readily determined by those skilled in the art and may be adjusted according to various factors such as type and severity of the disease, contents of active ingredients and other ingredients in the composition, dosage form, and the age, weight, physical condition and gender of the subject, as well as diet, administration timing and route and excretion rate of the composition, duration of treatment, and concurrent medication. For example, for adults, the TNFRI mutant of the present invention is preferably administered at a dose of 0.01 to 1,000 mg/kg once a day, and more preferably 0.1 to 100 mg/kg once a day.

The TNFRI polypeptide or a fragment thereof in accordance with the present invention may be administered as an addition for other therapies and may be administered with other pharmaceutical compositions suitable for the indication being treated. The TNFRI polypeptide or a fragment thereof in accordance with the present invention and any of one or more known or novel anti-inflammatory drugs may be administered separately or in combination. Information regarding the compounds corresponding to such drugs can be found in "The Merck Manual of Diagnosis and Therapy", Sixteenth Edition, Merck, Sharp & Dohme Research Laboratories, Merck & Co., Rahway, N.J. (1992) and in "Pharmaprojects", PJB Publications Ltd.

As an example of the combination use, the TNFRI polypeptide or a fragment thereof in accordance with the present invention may be used in combination with first line drugs for control of inflammation, classified as non-steroidal, anti-inflammatory drugs (NSAIDs), for the treatment of TNF-mediated diseases, including acute and chronic inflammation such as rheumatic diseases (e.g., lyme disease, juvenile (rheumatoid) arthritis, osteoarthritis, psoriatic arthritis, rheumatoid arthritis and staphylococcal-induced ("septic") arthritis).

As another example of the combination use, the TNFRI polypeptide or a fragment thereof in accordance with the present invention may be used in combination with any of one or more slow-acting antirheumatic drugs (SAARDs) or disease modifying antirheumatic drugs (DMARDS), prodrug esters or pharmaceutically acceptable salts thereof, for the treatment of TNF-mediated diseases and multiple sclerosis as defined above.

As a further example of the combination use, the TNFRI polypeptide or a fragment thereof in accordance with the present invention may be used in combination with any of one or more COX2 inhibitors, prodrug esters or pharmaceutically acceptable salts thereof for the treatment of TNF-mediated diseases as defined above.

Further, the TNFRI polypeptide or a fragment thereof in accordance with the present invention may be used in combination with any of one or more antibacterial drugs, prodrug esters or pharmaceutically acceptable salts thereof for the treatment of TNF-mediated diseases as defined above.

The TNFRI polypeptide or a fragment thereof in accordance with the present invention may be used for the treatment of TNF-mediated diseases as defined above, in combination with any of one or more compounds given below: granulocyte colony stimulating factor; thalidomide; tenidap; tiapafant; nimesulide; panavir; rolipram; sulfasalazine; balsalazide; olsalazine; mesalazine; prednisolone; budesonide; methylprednisolone; hydrocortisone; methotrexate; cyclosporin; peptide T; (1R,3S)-cis-1-[9-(2,6-diaminopurinyl)]-3-hydroxy-4-cyclopentene hydrochloride; (1R,3R)-trans-1-[9-(2,6-diamino)purine]-3-acetoxycyclopentane; (1R,3R)-trans-1-[9-adenyl)-3-azidocyclopentane hydrochloride and (1R,3R)-trans-1-[6-hydroxy-purin-9-yl)-3-azidocyclopentane.

The TNFRI polypeptide or a fragment thereof in accordance with the present invention may be used in combination with one or more additional TNF inhibitors for the treatment of TNF-mediated diseases as defined above. Such TNF inhibitors include compounds and proteins which block in vivo synthesis or extracellular release of TNF: for example, anti-TNF antibodies including MAK 195F Fab antibody (Holler et al. (1993), 1st International Symposium on Cytokines in Bone Marrow Transplantation, 147); CDP 571 anti-TNF monoclonal antibody (Rankin et al. (1995), British Journal of Rheumatology, 34:334-342); BAY X 1351 murine anti-tumor necrosis factor monoclonal antibody (Kieft et al. (1995), 7th European Congress of Clinical Microbiology and Infectious Diseases, 9); CenTNF cA2 anti-TNF monoclonal antibody (Elliott et al. (1994), Lancet, 344:1125-1127 and Elliott et al. (1994), Lancet, 344:1105-1110).

Further, the present invention provides a pharmaceutical preparation containing the TNFRI polypeptide or a fragment thereof. Preferably, the pharmaceutical preparation of the present invention further contains a pharmaceutically acceptable excipient. The pharmaceutical preparation of the present invention may be in the form of a pharmaceutical formulation selected from the group consisting of an oral formulation, an inhaler, an injection, a transmucosal formulation, and an external application.

The pharmaceutical preparation of the present invention contains a therapeutically effective amount of a pharmaceutically acceptable diluent, preservative, solubilizer, emulsifier, adjuvant or carrier.

In addition, the pharmaceutical preparation of the present invention contains additives including buffer (e.g. Tris buffer, acetate buffer, or phosphate buffer), detergents (e.g. Tween 80), antioxidants (e.g. ascorbic acid, sodium metabisulfite), preservatives (e.g. Thimerosal, benzyl alcohol) and bulking substances (e.g. lactose, mannitol) which have been commonly used in the art. The additives may be incorporated into particulate preparations of polymeric compounds such as polylactic acid or polyglycolic acid or into liposomes. The pharmaceutical preparation of the present invention may contain hyaluronic acid for the purpose of promoting sustained duration in circulation. The pharmaceutical preparation of the present invention may optionally contain pharmaceutically acceptable liquid, semisolid, or solid diluents that serve as pharmaceutical vehicles, excipients, or media, including, but not being limited to, polyoxyethylene sorbitan monolaurate, starches, sucrose, dextrose, gum acacia, calcium phosphate, mineral oil, cocoa butter, and theobroma oil.

The pharmaceutical preparation of the present invention also contains inert additives which furnish protection against the stomach environment, and release of the biologically active material in the intestine.

The pharmaceutical preparation of the present invention is prepared using known techniques, including mixing, dissolving, granulating, dragee-making, levigating, emulsifying, encapsulating, entrapping or tabletting processes.

The pharmaceutical preparation of the present invention may be in the form of a liquid (e.g., a suspension, elixir and/or solution) or a solid (e.g., a powder, tablet and/or capsule), or may be formulated in the form of a depot. The depot preparation is typically longer acting than non-depot preparations. The depot preparation is prepared using suitable polymeric or hydrophobic materials (for example, an emulsion in a suitable oil) or ion exchange resins, or as sparingly soluble derivatives, for example, as a sparingly soluble salt. Further, the pharmaceutical preparation of the present invention contains a delivery system such as liposome or emulsion. Certain delivery systems are useful for preparing certain pharmaceutical preparations including those containing hydrophobic compounds. In certain embodiments, organic solvents such as dimethyl sulfoxide are used. In another aspect of the present invention, the pharmaceutical preparation of the present invention contains one or more tissue-specific delivery molecules designed to deliver pharmaceutical agents to specific tissues or cell types. For example, in certain embodiments, the pharmaceutical preparation contains a liposome coated with a tissue-specific antibody.

Preferably, the pharmaceutical preparation of the present invention may be formulated into an oral solid dosage form. Solid dosage forms include tablets, capsules, pills, troches or pellets.

Also, liposomal or proteinoid encapsulation may be used to formulate the composition of the present invention. Liposomes may be prepared from phospholipids, such as phosphatidylcholine (PC), phosphatidylethanolamine (PE), phosphatidic acid (PA), phosphatidylinositol (PI) and sphingomyelin (SM); and hydrophilic polymers, such as polyvinylpyrrolidone, polyvinylmethyl ether, polymethyl oxazoline, polyethyl oxazoline, polyhydroxypropyl oxazoline, polyhydroxypropyl methacrylamide, polymethacrylamide, polydimethylacrylamide, polyhydroxypropyl methacrylate, polyhydroxyethyl acrylate, hydroxymethyl cellulose, hydroxyethyl cellulose, polyethylene glycol and polyaspartamide.

If necessary, the TNFRI polypeptide or a fragment thereof contained in the pharmaceutical preparation of the present invention may be chemically modified so that oral delivery is efficacious. Generally, the chemical modification contemplated is the attachment of at least one moiety to the TNFRI mutant polypeptide, where the moiety may be a substance which confers resistance to protease or helps uptake into the blood stream from the stomach or intestine. Preferably, the moiety for chemical modification may be a moiety for chemical modification to increase an overall stability of the pharmaceutical preparation of the present invention and therefore increase its circulation time in the body. Examples of the moiety include polyethylene glycol, copolymers of ethylene glycol and propylene glycol, carboxymethyl cellulose, dextran, polyvinyl alcohol, polyvinylpyrrolidone and polyproline. Other polymers that can be used are poly-1,3-dioxane and poly-1,3,6-trioxocane. Most preferred is a polyethylene glycol moiety (PEGylation).

As a carrier to enhance absorption of the pharmaceutical preparation of the present invention in the oral dosage form, a salt of a modified aliphatic amino acid, such as sodium N-(8-[2-hydroxybenzoyl]amino) caprylate (SNAC), may be used.

The pharmaceutical preparation of the present invention may be formulated as fine multiparticulates in the form of granules or pellets of a particle size of about 1 mm. In this case, the pharmaceutical may be in the form of a capsule. The multiparticulate preparation may be in the form of a powder, lightly compressed plug or tablet. The preparation may be prepared by compression.

The pharmaceutical preparation of the present invention may also be formulated in the form of, for example, liposome or microsphere encapsulation with further incorporation of colorants and flavoring agents.

Further, in order to enhance uptake of the TNFRI polypeptide or a fragment thereof which is an active ingredient in the pharmaceutical preparation of the present invention, additives may be used including fatty acids such as oleic acid or linoleic acid.

The pharmaceutical preparation of the present invention may be a controlled-release formulation. The TNFRI polypeptide or a fragment thereof, which is an active ingredient in such a formulation, may be incorporated into an inert carrier which permits controlled release by either diffusion or dissolution mechanisms. Further, the controlled-release formulation may contain a slowly disintegrating matrix, e.g., alginate or polysaccharide. Another form of the controlled-release formulation may be based on an Osmotic Release Oral delivery System (OROS, Alza Corp.). In the controlled-release formulation, the TNFRI mutant which is the active ingredient of the present invention is enclosed in a semi-permeable membrane which allows water to enter and push the active ingredient out through a single small opening due to osmotic effects. The controlled-release formulation of the present invention may have an enteric coating to exhibit a delayed release effect of the drug.

The pharmaceutical preparation of the present invention may be in the form of a film-coated tablet. The materials used in film coating are divided into two groups. The first group is a nonenteric material and includes methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, povidone and polyethylene glycol. The second group consists of enteric materials such as esters of phthalic acid. In detail, an enteric polymer as the enteric material is selected from the group consisting of an enteric cellulose derivative, an enteric acrylic copolymer, an enteric maleic copolymer, an enteric polyvinyl derivative, and a combination thereof. The enteric cellulose derivative is at least one selected from the group consisting of hypromellose acetate succinate, hypromellose phthalate, hydroxymethylethyl cellulose phthalate, cellulose acetate phthalate, cellulose acetate succinate, cellulose acetate maleate, cellulose benzoate phthalate, cellulose propionate phthalate, methylcellulose phthalate, carboxymethylethyl cellulose and ethylhydroxyethyl cellulose phthalate. The enteric acrylic copolymer is at least one selected from the group consisting of a styrene-acrylic acid copolymer, a methyl acrylate-acrylic acid copolymer, an acrylic acid-methyl methacrylate copolymer, a butyl acrylate-styrene-acrylic acid copolymer, a methacrylic acid-methyl methacrylate copolymer (e.g., Eudragit L 100, Eudragit S, Degussa), a methacrylic acid-ethyl acrylate copolymer (e.g., Eudragit L 100-55, Degussa), and methyl acrylate-methacrylic acid-octyl acrylate copolymer. The enteric maleic copolymer is at least one selected from the group consisting of a vinyl acetate-maleic anhydride copolymer, a styrene-maleic anhydride copolymer, a styrene-maleic acid monoester copolymer, a vinylmethylether-maleic anhydride copolymer, an ethylene-maleic anhydride copolymer, a vinylbutylether-maleic anhydride copolymer, an acrylonitrile-methyl acrylate-maleic anhydride copolymer, and a butyl acrylate-styrene-maleic anhydride copolymer. The enteric polyvinyl derivative is at least one selected from the group consisting of polyvinylalcohol phthalate, polyvinylacetal phthalate, polyvinylbutyrate phthalate, and polyvinylacetacetal phthalate.

A mixture of the above-mentioned coating materials may be used to provide the optimum film coating. Film coating may be carried out in a pan coater or in a fluidized bed granulator or by a compression coater.

The controlled-release pharmaceutical preparation of the present invention may contain the TNFRI polypeptide of the present invention or a fragment thereof in a semi-permeable matrix of a solid hydrophobic polymer in the form of a shaped article, e.g., film or microcapsule, for the purpose of sustained release of the drug. Examples of the sustained-release matrix include polyesters, hydrogels [e.g., poly(2-hydroxyethyl-methacrylate) or poly(vinylalcohol) as described by Langer et al., J. Biomed. Mater. Res., 15:167-277, 1981 and Langer, Chem. Tech., 12:98-105, 1982], polylactides (U.S. Pat. No. 3,773,919, EP 58,481), copolymers of L-glutamic acid and gamma ethyl-L-glutamate (Sidman et al., Biopolymers 22:547-556, 1983), non-degradable ethylene-vinyl acetate (Langer et al., supra), degradable lactic acid-glycolic acid copolymers (e.g., Lupron Depot™ (injectable microspheres composed of lactic acid-glycolic acid copolymer and leuprolide acetate), and poly-D-(−)-3-hydroxybutyric acid (EP 133,988).

When encapsulated proteins remain in the body for a long time, they may denature or aggregate as a result of being exposed to moisture at 37° C., resulting in a loss of biological activity and possible changes in immunogenicity. Rational strategies can be devised for protein stabilization depending on the mechanism involved. For example, if the aggregation mechanism is discovered to form intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Further, the present invention provides a TNFRI mutant of the present invention, and use of a pharmaceutical preparation containing the same. Such a pharmaceutical preparation may be administered via injection, or by oral, nasal, transdermal or other forms of administration, including, e.g., by intravenous, intradermal, intramuscular, intramammary, intraperitoneal, intrathecal, intraocular, intrapulmonary or subcutaneous injection; by sublingual, anal, vaginal, or by surgical implantation. The treatment may consist of a single dose or a plurality of doses over a period of time.

Further, the pharmaceutical preparation of the present invention may be delivered by a pulmonary delivery method. The pharmaceutical preparation of the present invention is delivered to the lung of a mammal while inhaling and traverses across the pulmonary epithelial lining to the blood stream.

A wide range of mechanical devices designed for pulmonary delivery of the drug may be used for pulmonary delivery of the pharmaceutical preparation of the present invention. Examples of such devices include nebulizers, metered dose inhalers, and powder inhalers, all of which are commercially available in the art.

The pharmaceutical preparation of the present invention may be appropriately formulated for optimum use in the foregoing devices. Typically, each formulation is specific to the type of device employed and may involve the use of an appropriate propellant, in addition to diluents, adjuvants or carriers useful in therapy.

The pharmaceutical preparation of the present invention for pulmonary delivery is preferably provided as a particulate form with an average particle size of approximately 10 μm or less, most preferably about 0.5 to 5 μm for effective delivery to the distal lung.

The pharmaceutical preparation of the present invention for pulmonary delivery may also contain a carbohydrate such as trehalose, mannitol, xylitol, sucrose, lactose or sorbitol, as a carrier. The pharmaceutical preparation may further contain dipalmitoylphosphatidylcholine (DPPC), dioleoylphoshatidyl ethanolamine (DOPE), distearoylphosphatidylcholine (DSPC) and dioleoylphosphatidylcholine (DOPC). The pharmaceutical preparation may also contain natural or synthetic surfactants. The pharmaceutical preparation may further contain polyethylene glycol, dextran such as cyclodextran, bile acid and other related derivatives, and amino acids used in a buffer formulation.

Also, the use of liposomes, microcapsules or microspheres, inclusion complexes, or other types of carriers is contemplated for pulmonary delivery of the pharmaceutical preparation of the present invention.

Pulmonary delivery of the pharmaceutical preparation of the present invention may be carried out using a nebulizer with either jet or ultrasonic means. The pharmaceutical preparation of the present invention suitable for use of a nebulizer contains the TNFRI mutant dissolved in water at a concentration of about 0.1 to 25 mg of biologically active protein per mL of solution. The nebulizer formulation may also include a buffer and monosaccharides, which, for example, contributes to protein stabilization and the regulation of osmotic pressure. The nebulizer formulation may also contain a surfactant to reduce or prevent surface inducing aggregation of the protein caused by atomization of the solution in forming the aerosol.

The pharmaceutical preparation of the present invention for use with a metered-dose inhaler device will generally contain a finely divided powder of the composition containing the TNFRI mutant of the present invention suspended in a propellant with the aid of a surfactant. The propellant may be a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or a combination thereof. Examples of a suitable surfactant that can be used herein include sorbitan trioleate and soya lecithin. Oleic acid may also be used as a surfactant.

The pharmaceutical preparation of the present invention for dispensing from a powder inhaler device is composed of a finely divided dry powder of the composition containing the TNFRI mutant of the present invention and may also contain a bulking agent such as lactose, sorbitol, sucrose, mannitol, trehalose or xylitol. These may facilitate dispersion of the powder from the device.

Nasal delivery of the pharmaceutical preparation of the present invention is also contemplated. Nasal delivery allows the passage of a protein therapeutic to the blood stream directly after administering the protein therapeutic to the nose, thus preventing pulmonary deposition of the therapeutic product. The pharmaceutical preparation of the present invention for nasal delivery contains dextran or cyclodextran, etc. Delivery via transport across other mucous membranes is also contemplated for the pharmaceutical preparation of the present invention.

The dosage regimen of the pharmaceutical preparation of the present invention involved in a method for treating the above-described diseases or conditions will be determined by the attending physician, in light of various factors which modify the action of drugs, e.g. the age, condition, body weight, sex and diet of the patient, the severity of any infection, the time of administration and other clinical factors.

The pharmaceutical preparation of the present invention may be administered via single dosing or continuous dosing, but is preferably administered by an initial bolus followed by a continuous infusion to maintain therapeutic levels of the drug in circulation. Typical techniques known in the art will readily optimize effective dosages and administration regimens. The frequency of dosing will depend on the pharmacokinetic parameters of the agents and the route of administration. The dosage regimen, administration regimen and frequency of dosing may also be optimized according to the physical state, stability, rate of in vivo release, and rate of in vivo clearance of the administered agents. For each route of administration, a suitable dose may be calculated according to body weight, body surface area or organ size. Appropriate dosages may be ascertained due to established assays used for determining blood level dosages in conjunction with appropriate dose-response data. The final dosage regimen will be determined by the attending physician, in light of various factors which modify the action of drugs, e.g. the drug's specific activity, the severity and the responsiveness of the patient, the age, condition, body weight, sex and diet of the patient and other clinical factors. As studies are conducted, further information will emerge regarding the appropriate dosage levels and duration of treatment for various diseases and conditions.

Advantageous Effects

The modified human tumor necrosis factor receptor-1 polypeptide or the fragment thereof in accordance with the present invention has improved ability to bind with TNF, as well as equivalent or higher protease resistance, compared to the wild-type human tumor necrosis factor receptor-1 polypeptide or a fragment thereof. Having these advantages over the wild-type polypeptide, the modified polypeptide of the present invention exhibits increased in-vivo half-life and guarantees improved bioavailability and absorption rate upon oral administration or injection. Therefore, the modified human tumor necrosis factor receptor-1 polypeptide or a fragment thereof in accordance with the present invention can be advantageously used as an active ingredient in a long-acting injection or oral formulation

MODE FOR INVENTION

Figure 1:
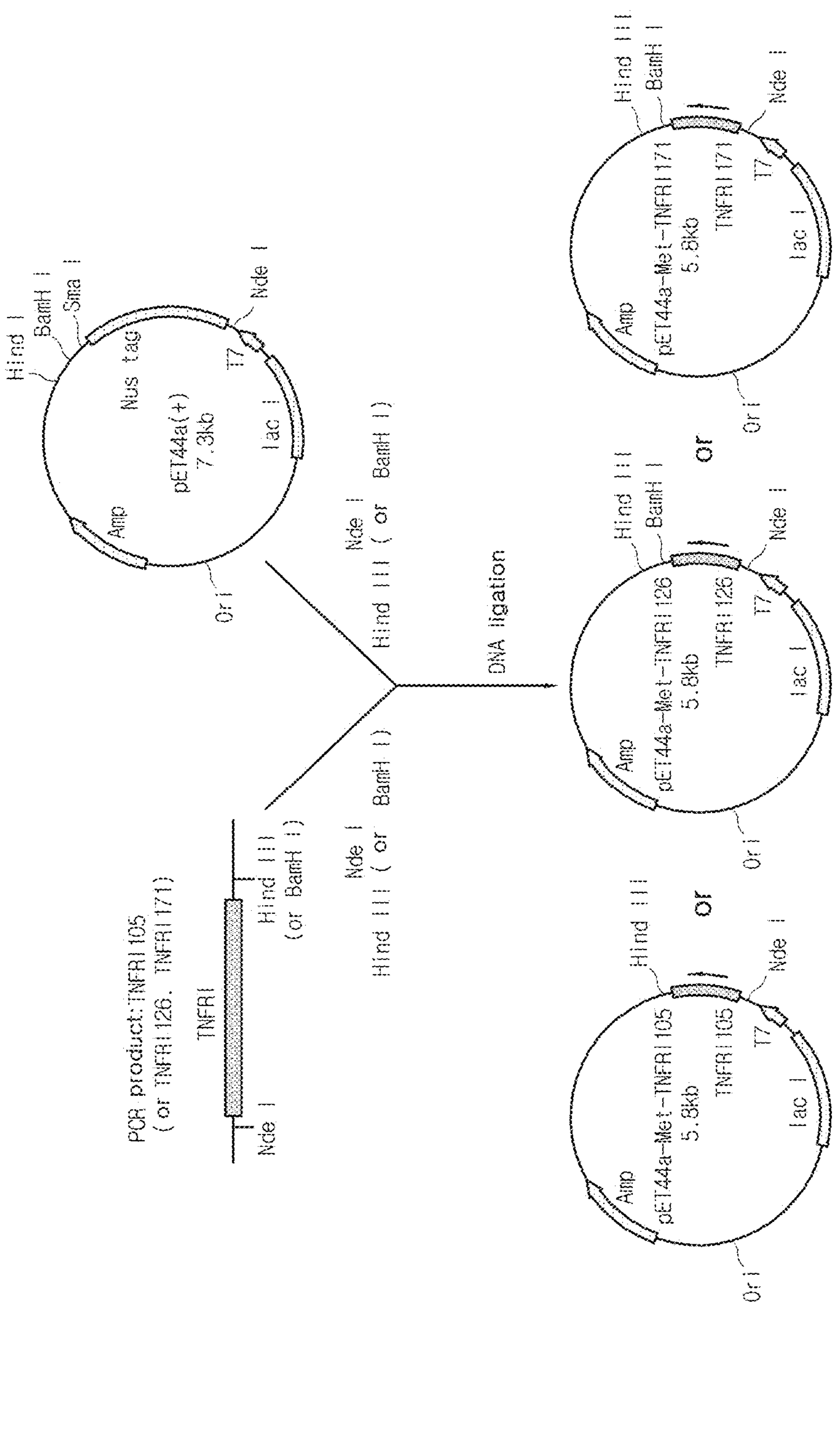
FIG. 1 is a schematic diagram illustrating the construction of Met-TNFRI105, Met-TNFRI126 or Met-TNFRI171 expression vectors for *E. coli*, by inserting a Met-TNFRI105, Met-TNFRI126 or Met-TNFRI171 gene into pET44a FIG. 2A is a gel filtration chromatogram showing the elution of Met-TNFRI105, Met-TNFRI126 and Met-TNFRI171 proteins (fraction A4)

The above and other objects, features and other advantages of the present invention will be more clearly understood from the following Examples. However, the present invention is not limited to the examples disclosed below.

The modified TNFRI polypeptide or a fragment thereof in accordance with the present invention was prepared using information of a human TNFRI genome whose genome has been already publicly disclosed.

PREPARATION EXAMPLE 1

Construction of TNFRI Gene Fragment and Vector for Expression (1) Construction of TNFRI171 Gene Fragment It is reported that human TNFRI has 4 extracellular domains, binding of TNFRI to TNF-α is possible even with only three domains of TNFRI (TNFRI126), and more deficiency of the extracellular domains has no effect on the binding of TNFRI to TNF-α. Based on this fact, TNFRI171 having 171 amino acid residues extending from amino acid residue 41 of the human TNFRI polypeptide as set forth in SEQ ID NO: 1, TNFRI126 having 126 amino acid residues extending from amino acid residue 41 of human TNFRI, and TNFRI105 having 105 amino acid residues extending from amino acid residue 41 of human TNFRI were selected as candidate peptides for constructing mutants of the present invention. For producing such mutants, the nucleotide sequence of TNFRI171 was modified to be convenient for expression in *E. coli*, using codons being matched with *E. coli* (SEQ ID NO: 5). This sequence was constructed by PCR-based gene synthesis method.

In order to insert the synthesized gene sequences into a pGEM-T (Cat. No: A1380, Promega) vector, 3 μl of the synthetic gene was added to 1 μl of the pGEM-T vector, and 1 μl of ligase (Cat. No: M2200S, NEB) and a ligation solution (2× ligation buffer) were added thereto, followed by reaction at room temperature for 10 minutes. 2 μl of the reaction solution was taken and added to an XL1-blue competent cell (Cat. No: RH119-J80, RBC) which was then transformed by applying heat shock at 37° C. for 2 minutes, followed by static culture in an LB solid medium containing ampicillin to obtain a colony. The colony was cultured in an LB liquid medium containing ampicillin, the plasmid was isolated therefrom and the gene sequence was confirmed by fluorescence-labeling of ddNTP using PCR (SolGent Inc., South Korea). This gene was designated as pGEM-TNFRI171. Hereinafter, TNFRI126 and TNFRI105 genes were obtained by PCR using the above-obtained pGEM-TNFRI171 gene as a template.

(2) Construction of TNFRI Expression Vector: Construction of TNFRI105, TNFR126 and TNFRI171 Expression Vectors A commercially available vector pET44a (Novagen, Cat. No: 71122-3) was used to constitute an expression vector.

Specifically, the Met-TNFRI105 gene (SEQ ID NO: 100) was obtained by PCR using the above-prepared pGEM-TNFRI171 plasmid as a template. The gene was designed to have the restriction enzyme sites Nde I and Hind III at 5' and 3' termini, respectively, which allow to clone the gene into the pET44a vector.

The primers used for this PCR amplification had the following base sequences:

```
Forward primer:
                                    (SEQ ID NO: 103)
5'-acatatggatagcgtgtgcccgc-3'

Reverse primer:
                                    (SEQ ID NO: 104)
5'-taagcttattaattaaaacactggaac-3'
```

The PCR started with denaturation at 95° C. for 5 min and proceeded with 25 cycles of denaturation at 95° C. for 1 min, annealing 60° C. for 40 sec and extension at 72° C. for 1 min, followed by final extension at 72° C. for 10 min. The PCR product thus obtained and the pET44a vector were separately digested at 37° C. for 3 hours with the restriction enzymes (Nde I, Hind III). After the enzymatic digestion, the digests were run on 1% agarose gel by electrophoresis, and DNA bands detected at the pertinent sizes were excised with a razor and extracted using a DNA extraction kit (GeneAll, Cat. No: 102-102). A ligation buffer (2× buffer) were mixed with 50 ng of the linearized pET44a vector, 200 ng of the Met-TNFRI105 gene, 1 μL of ligase (NEB, Cat. No: M2200S) and sterile distilled water to form a total volume of 20 μL, followed by incubation at room temperature for 10 min. 2 μl of the reaction solution was taken and added to an XL1-blue competent cell, which was then transformed by applying heat shock at 37° C. for 2 minutes, followed by static culture in an LB solid medium containing ampicillin to obtain a colony. The colony was cultured in an LB liquid medium containing ampicillin, the plasmid was isolated therefrom and the gene sequence was confirmed. The resulting recombinant plasmid was named pET44a-Met-TNFRI105 (FIG. 1).

The Met-TNFRI126 gene (SEQ ID NO: 101) was obtained by PCR using the pGEM-TNFRI171 plasmid as a template. The gene was designed to have the restriction enzyme sites Nde I and BamH I at 5' and 3' termini, respectively, which allow to clone the gene into the pET44a vector.

The primers used for this PCR amplification had the following base sequences:

```
Forward primer:
                                    (SEQ ID NO: 105)
5'-acatatggatagcgtgtgcccgc-3'

Reverse primer:
                                    (SEQ ID NO: 106)
5'-cggatccttaacaaactgtattctgcttc-3'
```

PCR reaction was performed in the same manner as was that for the Met-TNFRI105 gene. Also, the same procedure as in the construction of the Met-TNFRI105 expression vector was repeated with the exception that the restriction enzymes Nde I and BamH I were used. The resulting recombinant plasmid prepared from a culture of the colonies grown on a plate was named pET44a-Met-TNFRI126. The cloning of the gene of interest was confirmed by isolation of a plasmid from the colony, and base sequencing thereof (FIG. 1).

The Met-TNFRI171 gene (SEQ ID NO: 102) was obtained by PCR using the pGEM-TNFRI171 plasmid as a template. The gene was designed to have the restriction enzyme sites Nde I and BamH I at 5' and 3' termini, respectively, which allow to clone the gene into the pET44a vector.

The primers used for this PCR amplification had the following base sequences:

```
Forward primer:
                                    (SEQ ID NO: 107)
5'-acatatggatagcgtgtgcccgc-3'

Reverse primer:
                                    (SEQ ID NO: 108)
5'-cggatccttatgtggtgcctgagtcctc-3'
```

PCR reaction and the construction of *E. coli* expression vector were performed in the same manner as those for the Met-TNFRI126 gene. The resulting recombinant plasmid prepared from a culture of a colony was named pET44a-Met-TNFRI171. The cloning of the gene of interest was confirmed by isolation of a plasmid from the colony and, base sequencing on the plasmid (FIG. 1).

PREPARATION EXAMPLE 2

Construction of TNFRI Fragment Mutant with Improved Ability to Bind to TNF-α

(1) Design of TNFRI Mutant

Amino acid modifications that were applied to TNFRI105, TNFRI126 and TNFRI171 are listed in Table 1, below. In the amino acid sequence of SEQ ID NO: 1 for the wild-type human TNFRI, amino acid residues that were expected to be involved in binding to TNF-α were analyzed. The amino acid residues determined were substituted with other amino acids that were expected to improve the affinity of TNFRI for TNF-α.

TABLE 1

List of Designed TNFRI Amino Acid Modification

| No. | Position and Kind of Amino Acid Modification |
|---|---|
| #1 | H95F, R97P, H98A |
| #2 | S92I, H95F, R97P, H98A |
| #3 | S92G, H95F, R97P, H98A |
| #4 | S92A, H95F, R97P, H98A |
| #5 | S92V, H95F, R97P, H98A |
| #6 | S92L, H95F, R97P, H98A |
| #7 | S92P, H95F, R97P, H98A |
| #8 | S92F, H95F, R97P, H98A |
| #9 | S92M, H95F, R97P, H98A |
| #10 | S92W, H95F, R97P, H98A |
| #11 | S92C, H95F, R97P, H98A |
| #12 | S92N, H95F, R97P, H98A |
| #13 | S92Q, H95F, R97P, H98A |
| #14 | S92T, H95F, R97P, H98A |
| #15 | S92Y, H95F, R97P, H98A |
| #16 | S92K, H95F, R97P, H98A |
| #17 | S92R, H95F, R97P, H98A |
| #18 | S92H, H95F, R97P, H98A |
| #19 | S92D, H95F, R97P, H98A |
| #20 | S92E, H95F, R97P, H98A |
| #21 | S92I, H95F, R97P, H98G |
| #22 | S92M, H95F, R97P, H98G |
| #23 | S92I, E93P, H95F, R97L, H98A |
| #24 | S92I, E93P, H95F, R97I, H98A |
| #25 | S92I, E93P, H95F, R97F, H98A |
| #26 | S92I, E93P, H95F, R97P, H98G |
| #27 | S92I, E93P, H95F, R97L, H98G |
| #28 | S92I, E93P, H95F, R97I, H98G |
| #29 | S92I, E93P, H95F, R97F, H98G |
| #30 | S92I, E93P, H95F, R97P, H98A |

Mutants resulting from the introduction of the amino acid modifications suggested as Nos. 1 to 30 in Table 1 into TNFRI105, TNFRI126 and TNFRI171 were named TNFRI105-A1 to TNFRI105-A30, TNFRI126-A1 to TNFRI126-A30, and TNFRI171-A1 to TNFRI171-A30, respectively (the symbol "A" stands for affinity-increased mutant candidate. For example, TNFRI105-A1 means a TNFRI105 mutant candidate No. 1 that is expected to have increased affinity for TNF-α).

(2) Construction of DNA Encoding the TNFRI Mutants

Site-specific TNFRI mutants were constructed using site-directed mutagenesis. Primers that were employed for the construction of TNFRI mutants comprising the 30 amino acid mutations listed in Table 1 are summarized in Table 2, below.

Specifically, each of the primer pairs was dissolved at a concentration of 20 pM in distilled water and used to construct site-directed mutants by PCR in the presence of Pfu polymerase, with the TNFRI plasmid (pET44a-Met-TNFRI105, pET44a-Met-TNFRI126 or pET44a-Met-TNFRI171, previously constructed) serving as a template.

TNFRI105-A1, TNFRI-126-A1, TNFRI-171-A1, TNFRI105-A30, TNFRI-126-A30, and TNFRI-171-A30 genes were amplified using the primers corresponding to A30 and A1 of Table 2, with the above-prepared pET44a-Met-TNFRI105, pET44a-Met-TNFRI126 or pET44a-Met-TNFRI171 plasmid serving as a template and inserted into plasmids to construct recombinants plasmids (named pET-TNFRI105_A1, pET-TNFRI-126_A1, pET-TNFRI-171_A1, pET-TNFRI105_A30, pET-TNFRI126_A30, and pET-TNFRI171_A30, respectively). As described in Table 2, below, then, the plasmids were used as templates to construct pET-TNFRI_A2 to pET-TNFRI_A29.

The compositions used for the amplification are as follows: a total 50.0 μl of reaction solution containing 1.0 μl of each template plasmid DNA, 1.0 μl of 20 pmole N-primers, 1.0 μl of 20 pmole C-primers, 25.0 μl of 2× PrimeSTAR PCR buffer, 4.0 μl of 200 μM dNTP, 0.5 μl of PrimeSTAR HS DNA polymerase (Takara, Cat. No: R044A), and 17.5 μl of distilled water.

PCR started with denaturation 98° C. for 5 min and proceeded with 17 cycles of denaturation at 98° C. for 30 sec, annealing at 55° C. for 30 sec and extension at 72° C. for 9 min, followed by final extension at 72° C. for 10 min.

The reaction mixture was treated with Dpn I enzyme at 37° C. for 2 hours to degrade *E. coli*-derived DNA while the PCR product remained intact. 2 μl of DNA reaction solution was taken and added to an XL1-blue competent cell, which was then transformed by applying heat shock at 42° C. for 1 minutes, followed by static culture in an LB solid medium containing ampicillin to obtain a colony. The colony was cultured in an LB liquid medium containing ampicillin, the plasmid was isolated therefrom and the construction of site specific TNFRI mutants was confirmed by base sequencing.

TABLE 2

| Primers for Site-Directed Mutagenesis | | |
|---|---|---|
| | Primer | |
| No. | PCR Template | Primer Sequence |
| A30 | pET44a-Met-TNFRI105, pET44a-Met-TNFRI126, or pET44a-Met-TNFRI171 | 5'-GAGTGGGTCATTTACAGCGATTCCGAATTTTCTGCCGGCGTGCCTGAGCTGTTCTAAG-3' (SEQ ID NO: 109) 5'-cttagaacagctcaggcacgccggcagaaaattcggaatcgctgtaaatgacccactc-3' (SEQ ID NO: 110) |
| A1 | pET44a-Met-TNFRI105, pET44a-Met-TNFRI126, or pET44a-Met-TNFRI171 | 1' PCR 5'-CATTTACAGCGAGTGAGAATTTTCTGCGCGCGTGCCTGAGCTGTTCTAAG-3' (SEQ ID NO: 111) 5' cttagaacagctcaggcacgcgcgcagaaaattctcactcgctgtaaatg-3' (SEQ ID NO: 112) 2' pcr 5' GAGTGAGAATTTTCTGCCGGCGTGCCTGAGCTGT-3' (SEQ ID NO: 113) 5' ACAGCTCAGGCACGCCGGCAGAAAATTCTCACTC-3' (SEQ ID NO: 114) |
| A2 | pET-TNFRI_A30 | 5'-GTCATTTACAGCGattGAGAATTTTCTGCCGGC-3' (SEQ ID NO: 115) 5'-GCCGGCAGAAAATTCTCAATCGCTGTAAATGAC-3' (SEQ ID NO: 116) |
| A3 | pET-TNFRI_A2 | 5'-GGGTCATTTACAGCGgggGAGAATTTTCTGC-3' (SEQ ID NO: 117) 5'-GCAGAAAATTCTCcccCGCTGTAAATGACCC-3' (SEQ ID NO: 118) |
| A4 | pET-TNFRI_A2 | 5'-GGGTCATTTACAGCGgcgGAGAATTTTCTGC-3' (SEQ ID NO: 119) 5'-GCAGAAAATTCTCcgcCGCTGTAAATGACCC-3' (SEQ ID NO: 120) |
| A5 | pET-TNFRI_A2 | 5'-GGGTCATTTACAGCGgttGAGAATTTTCTGC-3' (SEQ ID NO: 121) 5'-GCAGAAAATTCTCaacCGCTGTAAATGACCC-3' (SEQ ID NO: 122) |
| A6 | pET-TNFRI_A2 | 5'-GGGTCATTTACAGCGctgGAGAATTTTCTGC-3' (SEQ ID NO: 123) 5'-GCAGAAAATTCTCcagCGCTGTAAATGACCC-3' (SEQ ID NO: 124) |
| A7 | pET-TNFRI_A2 | 5'-GGGTCATTTACAGCGccgGAGAATTTTCTGC-3' (SEQ ID NO: 125) 5'-GCAGAAAATTCTCcggCGCTGTAAATGACCC-3' (SEQ ID NO: 126) |
| A8 | pET-TNFRI_A2 | 5'-GGGTCATTTACAGCGtttGAGAATTTTCTGC-3' (SEQ ID NO: 127) 5'-GCAGAAAATTCTCaaaCGCTGTAAATGACCC-3' (SEQ ID NO: 128) |
| A9 | pET-TNFRI_A2 | 5'-GGGTCATTTACAGCGatgGAGAATTTTCTGC-3' (SEQ ID NO: 129) 5'-GCAGAAAATTCTCcatCGCTGTAAATGACCC-3' (SEQ ID NO: 130) |
| A10 | pET-TNFRI_A2 | 5'-GGGTCATTTACAGCGtggGAGAATTTTCTGC-3' (SEQ ID NO: 131) 5'-GCAGAAAATTCTCccaCGCTGTAAATGACCC-3' (SEQ ID NO: 132) |

TABLE 2-continued

| Primers for Site-Directed Mutagenesis | | |
|---|---|---|
| | | Primer |
| No. | PCR Template | Primer Sequence |
| A11 | pET-TNFRI_A2 | 5'-GGGTCATTTACACCGtgcGAGAATTTTCTGC-3' (SEQ ID NO: 133)<br>5'-GCAGAAAATTCTCgcaCGCTGTAAATGACCC-3' (SEQ ID NO: 134) |
| A12 | pET-TNFRI_A2 | 5'-GGGTCATTTACAGCGaatGAGAATTTTCTGC-3' SEQ ID NO: 135)<br>5'-GCAGAAAATTCTCattCGCTGTAAATGACCC-3' (SEQ ID NO: 136) |
| A13 | pET-TNFRI_A2 | 5'-GGGTCATTTACAGCGcagGAGAATTTTCTGC-3' (SEQ ID NO: 137)<br>5'-GCAGAAAATTCTCctgCGCTGTAAATGACCC-3' (SEQ ID NO: 138) |
| A14 | pET-TNFRI_A2 | 5'-GGGTCATTTACAGCGacaGAGAATTTTCTGC-3' (SEQ ID NO: 139)<br>5'-GCAGAAAATTCTCtgtCGCTGTAAATGACCC-3' (SEQ ID NO: 140) |
| A15 | pET-TNFRI_A2 | 5'-GGGTCATTTACAGCGtacGAGAATTTTCTGC-3' (SEQ ID NO: 141)<br>5'-GCAGAAAATTCTCgtaCGCTGTAAATGACCC-3' (SEQ ID NO: 142) |
| A16 | pET-TNFRI_A2 | 5'-GGGTCATTTACAGCGaagGAGAATTTTCTGC-3' (SEQ ID NO: 143)<br>5'-GCAGAAAATTCTCcttCGCTGTAAATGACCC-3' (SEQ ID NO: 144) |
| A17 | pET-TNFRI_A2 | 5'-GGGTCATTTACAGCGcgcGAGAATTTTCTGC-3' (SEQ ID NO: 145)<br>5'-GCAGAAAATTCTCgcgCGCTGTAAATGACCC-3' (SEQ ID NO: 146) |
| A18 | pET-TNFRI_A2 | 5'-GGGTCATTTACAGCGcatGAGAATTTTCTGC-3' (SEQ ID NO: 147)<br>5'-GCAGAAAATTCTCatgCGCTGTAAATGACCC-3' (SEQ ID NO: 148) |
| A19 | pET-TNFRI_A2 | 5'-GGGTCATTTACAGCGgatGAGAATTTTCTGC-3' (SEQ ID NO: 149)<br>5'-GCAGAAAATTCTCatcCGCTGTAAATGACCC-3' (SEQ ID NO: 150) |
| A20 | pET-TNFRI_A2 | 5'-GGGTCATTTACAGCGgaaGAGAATTTTCTGC-3' (SEQ ID NO: 151)<br>5'-GCAGAAAATTCTCttcCGCTGTAAATGACCC-3' (SEQ ID NO: 152) |
| A21 | pET-TNFRI_A2 | 5'-GAGAATTTTCTGCCGGGGTGCCTGAGCTGTTCTA-3' (SEQ ID NO: 153)<br>5'-TAgaacagctcaggcaccccggcagaaaattCTC-3' (SEQ ID NO: 154) |
| A22 | pET-TNFRI_A9 | 5'-GAGAATTTTCTGCCGGGGTGCCTGAGCTGTTCTA-3' (SEQ ID NO: 155)<br>5'-TAgaacagctcaggcaccccggcagaaaattCTC-3' (SEQ ID NO: 156) |
| A23 | pET-TNFRI_A30 | 5'-GATTCCGAATTTTCTGCTGGCGTGCCTGAGCTGT-3' (SEQ ID NO: 157)<br>5'-acagctcaggcacgccagcagaaaattcggaatc-3' (SEQ ID NO: 158) |
| A24 | pET-TNFRI_A30 | 5'-GATTCCGAATTTTCTGATTGCGTGCCTGAGCTGT-3' (SEQ ID NO: 159) |

TABLE 2-continued

| Primers for Site-Directed Mutagenesis | | |
|---|---|---|
| | | Primer |
| No. | PCR Template | Primer Sequence |
| | | 5'-acagctcaggcacgcaatcagaaaattcggaatc-3' (SEQ ID NO: 160) |
| A25 | pET-TNFRI_A30 | 5'-GATTCCGAATTTTCTGTTTGCGTGCCTGAGCTGT-3' (SEQ ID NO: 161) 5'-acagctcaggcacgcaaacagaaaattcggaatc-3' (SEQ ID NO: 162) |
| A26 | pET-TNFRI_A30 | 5'-TCCGAATTTTCTGCCGGGGTGCCTGAGCTGTTC-3' (SEQ ID NO: 163) 5'-gaacagctcaggcaccccggcagaaaattcgga-3' (SEQ ID NO: 164) |
| A27 | pET-TNFRI_A30 | 5'-AGCGATTCCGAATTTTCTGCTGGGGTGCCTGAGCTGTTCTAAG-3' (SEQ ID NO: 165) 5'-CTTAgaacagctcaggcaccccagcagaaaattcggaatcgct-3' (SEQ ID NO: 166) |
| A28 | pET-TNFRI_A30 | 5'-AGCGATTCCGAATTTTCTGATTgggTGCCTGAGCTGTTCTAAG-3' (SEQ ID NO: 167) 5'-CTTAgaacagctcaggcacccaatcagaaaattcggaatcgct-3' (SEQ ID NO: 168) |
| A29 | pET-TNFRI_A30 | 5'-AGCGATTCCGAATTTTCTGTTTgggTGCCTGAGCTGTTCTAAG-3' (SEQ ID NO: 169) 5'-CTTAgaacagctcaggcacccaaacagaaaattcggaatcgct-3' (SEQ ID NO 170) |

(3) Production of Biologically Active Met-TNFRI and Met-TNFRI Mutants in *E. coli*

(a) Expression of Met-TNFRI and Met-TNFRI Mutants

BL21Star (DE3) (Invitrogen, Cat. No: C6010-03) competent cells were transformed with 1 μL of the constructed plasmid by heat shock at 42° C. for 1 min and incubated on LB plates to form colonies. The *E. coli* BL21Star (DE3) anchoring the expression vector therein was inoculated into 50 mL of YP broth (yeast extract: Merck, Cat. No: 103753, peptone: BD, Cat. No: 243620, NaCl: Merck, Cat. No: 1064049025) containing 100 μg/mL ampicillin and incubated at 37° C. for 16 hours with aeration. The culture was inoculated to an O.D. of 0.1 at 600 nm into 250 mL of YP broth containing 100 μg/ml ampicillin in a 1 L flask. When the cells were grown at 37° C. to an O.D. of 3~4 at 600 nm, IPTG was added at a final concentration of 1.0 mM to induce expression. After IPTG induction, the cells were incubated at 37° C. for an additional 3 hours with aeration and harvested by spinning at 6000 rpm for 20 min.

(b) Recovery of Insoluble Met-TNFRI and Met-TNFRI Mutants

The collected cells were resuspended in a resuspension solution (50 mM Tris, 0.5 mM EDTA, pH 8.5) and disrupted with a sonicator (Sonics, Cat. No: VCX 750). After centrifugation at 8000×g and 10° C. for 30 min, the supernatant was discarded and the pellet was suspended in washing buffer 1 (50 mM Tris, 10 mM EDTA, 0.5% Triton X-100, pH 8.0) and centrifuged at 8000×g and 10° C. for 20 min. The supernatant was discarded and the resulting pellet was resuspended in a resuspension solution and centrifuged at 8000×g and 10° C. for 20 min. The pellet was used immediately or freeze-stored at −80° C. until use.

(c) Solubilization and Refolding of Met-TNFRI and Met-TNFRI Mutants

The pellet was solubilized in 6 mL of a denaturation solution (6~8 M urea or 6~8 M guanidine-HCl, 10 mM dithiothreitol (DTT), 2.0 mM EDTA, 0.2 M NaCl). The insoluble part of the pellet was filtered off through a 0.45 μm syringe filter. The pellet-solubilized solution was 20-fold diluted in a refolding solution (50 mM Tris, 1.0 mM EDTA, 0.5 M L-arginine, 6.0 mM GSH, 4.0 mM GSSG, 240 mM NaCl, 10 mM KCl, pH 9.0) and gently stirred at 4° C. for 12~24 hours to induce refolding.

(d) Purification of Refolded Met-TNFRI and Met-TNFRI Mutants

In order to purify refolded Met-TNFRI and Met-TNFRI mutants, the refolding solutions were 20-fold concentrated using a 3 kD Amicon Ultra (Millipore, Cat. No: UFC900324), followed by gel filtration chromatography using a Superdex 75 prep grade resin (GE)-packed XK25/70 column (GE, Cat. No: 19-0146-01).

Figure 2A:
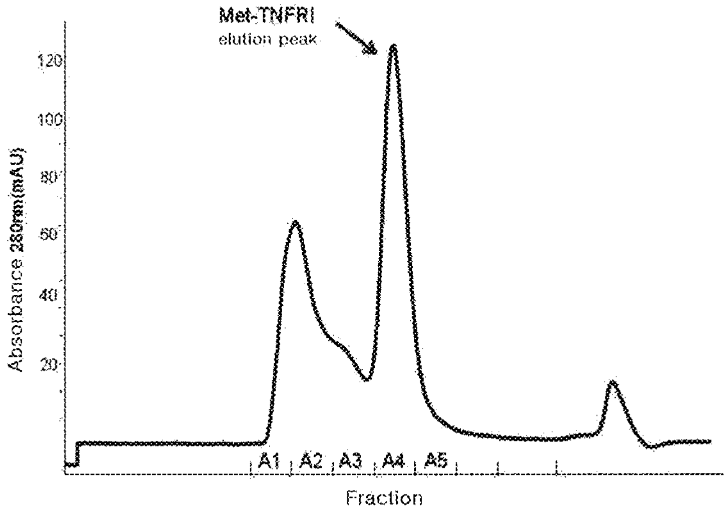
FIG. 2B is a photograph showing purified Met-TNFRI105, Met-TNFRI126 and Met-TNFRI171 separated by SDS-PAGE (silver staining).
Figure 2B:
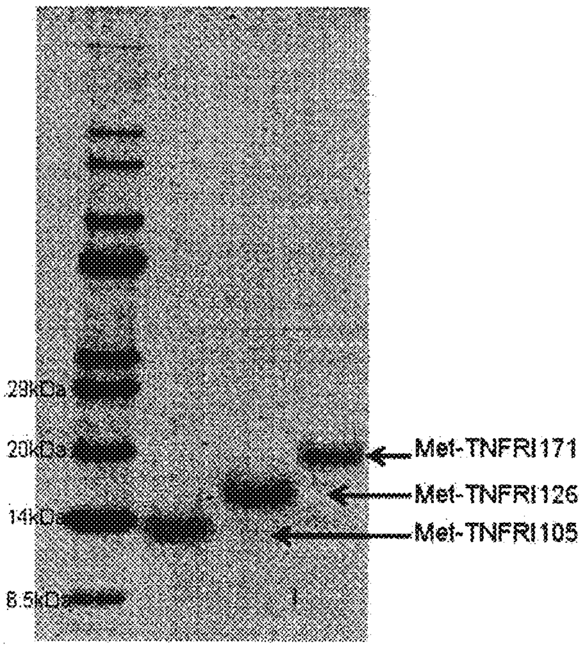

Before the refolded sample was loaded thereonto, the column was equilibrated with 4-5 volumes of an equilibration buffer (50 mM sodium phosphate, 100 mM NaCl, pH 7.0). After 2 mL of the sample was loaded onto the equilibrated column, the equilibration solution was allowed to flow through the column at a flow rate of 5 mL/min and 5 mL fractions were taken. Only the fractions that were observed to have a purity of 90% or higher, as analyzed by SDS-PAGE, were used. Through this procedure, Met-TNFRI105, Met-TNFRI126, Met-TNFRI171, a Met-TNFRI105 mutant, a Met-TNFRI126 mutant and a Met-TNFRI171 mutant were purified (FIG. 2).

EXPERIMENTAL EXAMPLE 1

Analysis of the Affinity of Met-TNFRI for the Ligand (TNF-α)

The Met-TNFRI and the Met-TNFRI mutant, both having a purity of 90% or higher, were quantitatively analyzed using the Bradford method and assayed for affinity for TNF-α using, ELISA.

TNFRI190 (consisting of 190 amino acid residues extending from position 22 to position 211 in the amino acid sequence of TNFRI of SEQ ID NO: 1; R&D, Cat No: 636-R1-025-CF) was plated at a concentration of 1 μg/ml in an amount of 100 μL into 96-well plates and immobilized at 4° C. for 16 hours. Each well was washed three times with 300 μL of washing buffer (0.05% Tween-20, PBS, pH 7.4) and incubated at room temperature for 2 hours with 300 μL of a blocking buffer (5% skim milk, PBS, pH 7.4). Then, each well was washed as mentioned above. A sample of interest was diluted to concentrations of 500 nM, 125 nM, 31 nM, 7.8 nM, 1.9 nM, 0.48 nM, 0.12 nM, and 0.03 nM in series and loaded in an amount of 100 μL into each well in duplicate. To each well was added 100 μL of 50 ng/ml TNF-α, followed by incubation at room temperature for 2 hours. After the wells were washed with a washing buffer, 100 μg/mL anti-TNF-α antibody solution was diluted 1/1000, added in an amount of 100 μL per each well, and incubated at room temperature for 2 hours. After the plates were washed with a washing buffer, a substrate was added in an amount of 100 μL to each well and reacted at room temperature for 15 min. In each well, 100 μL of the substrate 3,3',5,5'-tetramethylbenzidine (RnD, Cat. No: DY999) was reacted at room temperature for 15 min, followed by adding 50 μL of 1.0 M sulfuric acid (Samchun Chemical, Cat. No: 52129) to each well to stop the reaction. Absorbance at 450 and 540 nm was read on a Vmax reader (MD, Model: VersaMax).

Figure 3:
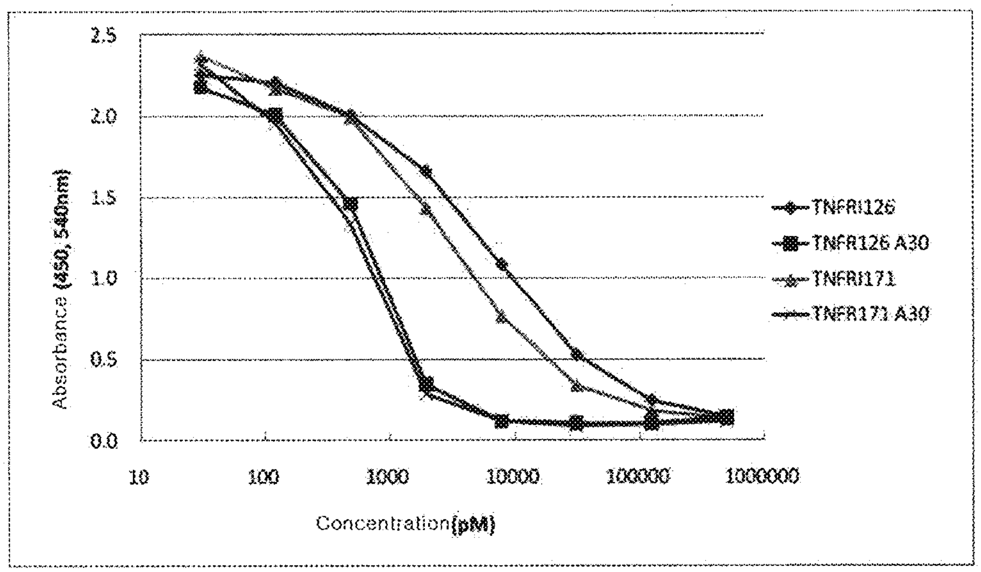
FIG. 3 is a graph showing the binding ability of TNFRI fragments (TNFRI126, TNFRI171) and TNFRI mutant fragments (TNFRI126-A30, TNFRI171-A30) to bind TNF-α as analyzed by ELISA.

Affinity of Met-TNFRI and Met-TNFRI mutants for TNF-α was determined by measuring an absorbance change with concentration and evaluating $IC_{50}$ value by measuring an absorbance change with concentration. Affinity of Met-TNFRI mutant relative to the wild-type TNFRI was determined therefrom. The results are shown in Table 3, below. Data of the representative mutants TNFRI126-A30 and TNFRI171-A30 are depicted in FIG. 3. As can be seen in FIG. 3, TNFRI126 and TNFRI171 have substantially the same effect. In addition, the TNFRI mutants of the present invention exhibited affinity improved by as high as 1,400% compared to that of the wild-type TNFRI.

EXPERIMENTAL EXAMPLE 2

Assay of Evaluation Met-TNFRI and Met-TNFRI Mutants for Biological Activity by Neutralization of Cytotoxicity of TNF-α

Purified Met-TNFRI and Met-TNFRI mutants were quantitatively analyzed using the Bradford method and were applied to WEHI cells (ATCC, Cat. No: CRL-2148), which are susceptible to a certain concentration of TNF-α, to measure the protection of the cells from the cytotoxicity of TNF-α.

Specifically, WEHI(ATCC, Cat. No: CRL-2148) cells were suspended at a density of $2\times10^5$ cells/ml in RPMI medium supplemented with 5% fetal bovine serum, 50 U/ml penicillin and 50 mg/ml streptomycin. The cell suspension was plated in an amount of 100 μL/well into 96-well microtiter plates and cultured at 37° C. for 24 hours in a 5% $CO_2$ atmosphere. To each well was added 100 μL of 70 pg/mL TNF-α in a medium containing actinomycin-D. In PBS, 100 μg/mL of each mutant sample was diluted from 3.0 nM to 0.18 pM, and added to each well containing TNF-α. For reference, Enbrel (Amgen, chemical name: etanercept) was applied at a concentration of from 0.04 pM to 3.0 nM while the wild-type TNFRI was used at a concentration of from 12 pM to 200 nM. WEHI cells were incubated at 37° C. for 24 hours in a 5% $CO_2$ atmosphere and then for an additional 4-6 hours with an MTT reagent (MTT assay kit, Roche, Cat. No: 11455007001). A solubilizing reagent was added into each well. After incubation for 24 hours, dissolution of the purple formazan was identified, after which absorbance at 570 nm was read on a Vmax reader. Activities of the Met-TNFRI and the Met-TNFRI mutants were determined by measuring $ND_{50}$ values through absorbance change with concentrations and calculating relative activity to the wild-type TNFRI. The result was summarized in Table 4, below. Data of the representative mutants TNFRI126-A30, TNFRI171-A2, TNFRI171-A9, TNFRI171-A21, TNFRI171-A22, and TNFRI171-A30 are shown in FIG. 4.

Figure 4A:
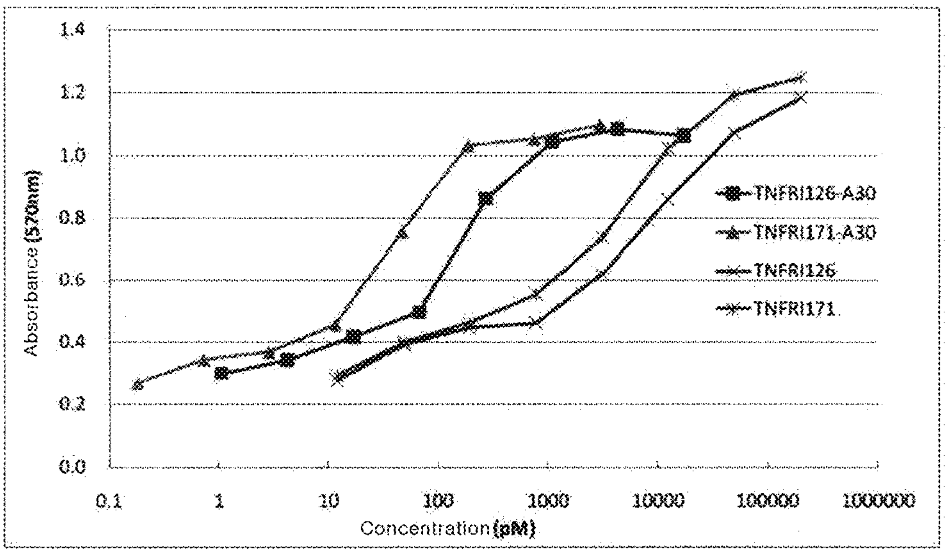
FIG. 4A is a graph showing the biological activity of TNFRI fragments (TNFRI126, TNFRI171) and TNFRI fragment mutants (TNFRI126-A30, TNFRI171-A30) as analyzed by neutralization against the cytotoxicity of TNF-α.
Figure 4B:
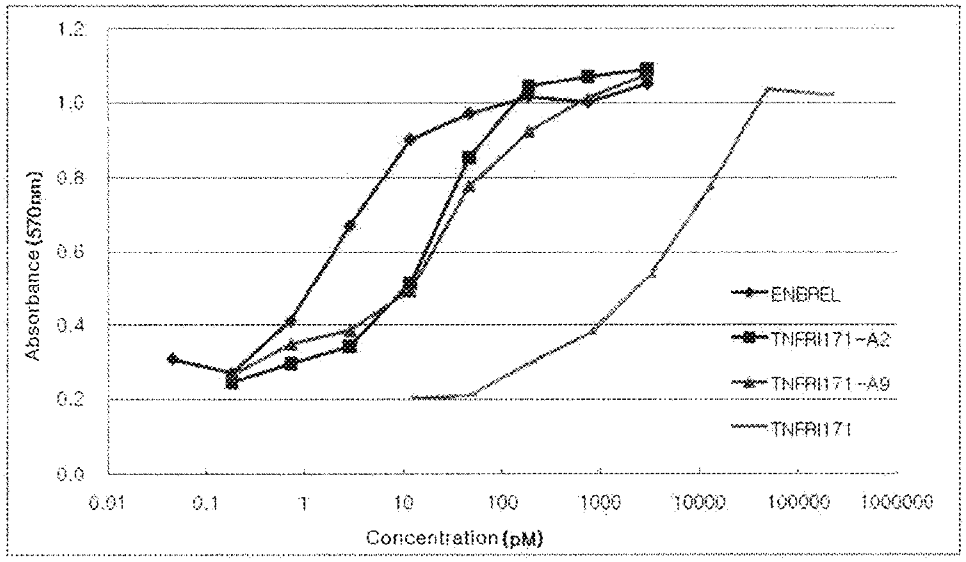
FIG. 4B is a graph showing the biological activity of ENBREL™, a TNFRI fragment (TNFRI171) and TNFRI fragment mutants (TNFRI171-A2, TNFRI171-A9) as analyzed by neutralization against the cytotoxicity of TNF-α.
Figure 4C:
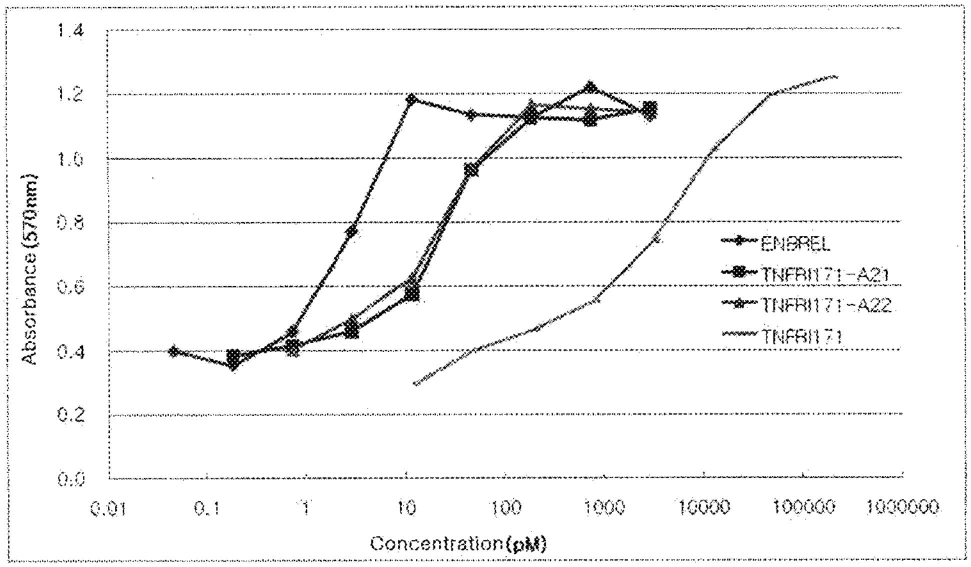
FIG. 4C is a graph showing the biological activity of ENBREL™, a TNFRI fragment (TNFRI171) and TNFRI fragment mutants (TNFRI171-A21, TNFRI171-A22) as analyzed by neutralization against the cytotoxicity of TNF-α.

As can be seen in FIG. 4A, TNFRI126 and TNFRI171 were observed to exhibit substantially the same effect. In addition, the biological activity of the Met-TNFRI mutants according to the present invention were higher than that of the wild-type TNFRI. For example, TNFRI171-A2, TNFRI171-A21, and TNFRI171-A22 were 200-fold higher in biological activity than the wild-type TNFRI as analyzed for neutralization against the cytotoxicity of TNF-α (Table 4). Therefore, the cytotoxicity-neutralizing activity of TNFRI mutants increased with an increase in the affinity for TNF-α.

EXPERIMENTAL EXAMPLE 3

Resistance of Met-TNFRI and Met-TNFRI to Proteases

Met-TNFRI and Met-TNFRI mutants were assayed for protease resistance. First, the total protein concentration of a purified protein (e.g., TNFRI) solution was determined using the Bradford method. Swine pancreatin (Sigma, Cat. No: P7545) was treated in an amount of 40% of the total protein concentration to degrade the purified protein. The half-life of each mutant according to treatment with pancreatin was determined and compared to that of the wild-type TNFRI.

Specifically, concentrations of Met-TNFRI and each mutant were determined by the Bradford method and adjusted into 100 μg/ml using PBS. Each of the protein samples thus obtained was placed in an amount of 250 μL in a 500 μL-centrifuge tube. To this tube was added 30 μL of 0.1 M sodium phosphate containing 10 μg of pancreatin, followed by incubation at 37° C. At 0 min, 5 min, 10 min, 15 min, 20 min, 30 min, 40 min, 60 min after the incubation, 30 μL of each sample was taken, mixed with 270 μL of 5% BSA solution containing 5 μL of a protease inhibitor (Roche, Cat. No: 11836170001) and stored in liquid nitrogen. The half-life of each of the Met-TNFRI mutants was determined by quantitatively analyzing intact protein using ELISA (RnD, Cat. No: DY225). The half-life of each of the mutants is expressed as a percentage of that of Met-TNFRI (Tables 3 and 4). As shown, the Met-TNFRI mutants having increased affinity were found to be more readily degraded by proteases.

TABLE 3

Determination of Affinity and Protease Resistance of the Mutants by ELISA Assay

| Mutant No. | Results Affinity (%) | Resistance (%) |
|---|---|---|
| Wild-type (TNFRI126) | 100 | 100 |
| TNFRI126-A1 | 324 | N/A |
| TNFRI126-A2 | 829 | 70 |
| TNFRI126-A3 | 341 | N/A |
| TNFRI126-A4 | 524 | N/A |
| TNFRI126-A5 | 712 | N/A |
| TNFRI126-A6 | 741 | N/A |
| TNFRI126-A7 | 600 | N/A |
| TNFRI126-A8 | 865 | 64 |
| TNFRI126-A9 | 941 | 69 |
| TNFRI126-A10 | 800 | 43 |
| TNFRI126-A11 | N/A | N/A |
| TNFRI126-A12 | 659 | N/A |
| TNFRI126-A13 | 806 | 45 |
| TNFRI126-A14 | 765 | N/A |
| TNFRI126-A15 | 941 | 66 |
| TNFRI126-A16 | 882 | 56 |
| TNFRI126-A17 | 771 | N/A |
| TNFRI126-A18 | 1012 | 82 |
| TNFRI126-A19 | 482 | N/A |
| TNFRI126-A20 | 782 | N/A |
| TNFRI126-A21 | 1404 | 50 |
| TNFRI126-A22 | 1434 | 52 |
| TNFRI126-A23 | 1105 | N/A |

TABLE 3-continued

Determination of Affinity and Protease Resistance of the Mutants by ELISA Assay

| Mutant No. | Results Affinity (%) | Resistance (%) |
|---|---|---|
| TNFRI126-A24 | 1059 | N/A |
| TNFRI126-A25 | 682 | N/A |
| TNFRI126-A26 | 1141 | 46 |
| TNFRI126-A27 | 894 | N/A |
| TNFRI126-A28 | N/A | N/A |
| TNFRI126-A29 | 435 | N/A |
| TNFRI126-A30 | 952 | 45 |

TABLE 4

Determination of Biological Activity by Cytotoxicity Assay and Protease Resistance of the Mutants

| Mutant No. | Relative Activity (Cytotoxicity-neutralizing activity) (fold) | Relative Resistance to Protease (%) |
|---|---|---|
| Wild-type (TNFRI171) | 1 | 100 |
| TNFRI171-A2 | 207 | 45 |
| TNFRI171-A8 | 120 | 47 |
| TNFRI171-A9 | 158 | 47 |
| TNFRI171-A10 | 44 | 26 |
| TNFRI171-A15 | 142 | 45 |
| TNFRI171-A16 | 139 | 33 |
| TNFRI171-A18 | 126 | 68 |
| TNFRI171-A21 | 226 | 30 |
| TNFRI171-A22 | 242 | 39 |
| TNFRI171-A26 | 196 | 16 |
| TNFRI171-A30 | 127 | 28 |

PREPARATION EXAMPLE 3

Selection of Mutants Improved in Protease Resistance (1) Design of TNFRI Mutants Mutants were designed to have resistance to proteases. Mutagenesis positions in the amino acid sequence of TNFRI117 were inferred by analyzing the cleavage sites of 10 typical proteases present in the gastrointestinal tract, cells and blood with the aid of the peptide cutter program (http://www.expasy.org/tools/peptidecutter/) provided by Expasy (Expert Protein Analysis System). Amino acid residues in the inferred cleavage sites were substituted with amino acids that are resistant to the proteases and cause as little a structural change as possible. The PAM250 matrix was used to determine the amino acids to substitute for the inferred residues. Referring to the PAM250 matrix suggesting 19 amino acids that have positive, zero and negative values for each amino acid, amino acids that are not cleaved by proteases and have positive or zero values were determined as substituents.

TABLE 5

| Protease-Specific Amino Acids and Resistance-Inducing Amino Acid | | |
|---|---|---|
| Protease | Recognized and Cleaved Amino Acid | Cleavage Resistance Inducing Amino Acid |
| Arg-C Protease | R | H or Q |
| Asp-N endopeptidase | -D | N or Q |
| Chymotrypsin | [FYWML] (SEQ ID NO: 171), not before P | S or I, H |
| Enterokinase | K | N or Q |
| Glutamyl endopeptidase | E | N or Q |
| Lys-C | K | N or Q |
| Lys-N | K | N or Q |
| Proline endopeptidase | H, K or R, -P | A or S |
| Thrombin | R | N or Q |
| Trypsin | K | N or Q |

The TNFRI mutants designed are listed in Table 6, below.

TABLE 6

| List of Designed TNFRI Mutant | |
|---|---|
| Mutant No. | Mutation |
| TNFRIx-R1 | K48Q |
| TNFRIx-R2 | K48N |
| TNFRIx-R3 | Y49I |
| TNFRIx-R4 | Y49H |
| TNFRIx-R5 | P52A |
| TNFRIx-R6 | P52S |
| TNFRIx-R7 | K61Q |
| TNFRIx-R8 | K61N |
| TNFRIx-R9 | K64Q |
| TNFRIx-R10 | K64N |
| TNFRIx-R11 | Y67I |
| TNFRIx-R12 | Y67H |
| TNFRIx-R13 | L68I |
| TNFRIx-R14 | L68V |
| TNFRIx-R15 | Y69I |
| TNFRIx-R16 | Y69H |
| TNFRIx-R17 | D71N |
| TNFRIx-R18 | D71Q |
| TNFRIx-R19 | D78N |
| TNFRIx-R20 | D78Q |
| TNFRIx-R21 | D80N |
| TNFRIx-R22 | D80Q |
| TNFRIx-R23 | R82H |
| TNFRIx-R24 | R82Q |
| TNFRIx-R25 | E83Q |
| TNFRIx-R26 | E83N |
| TNFRIx-R27 | E85Q |
| TNFRIx-R28 | E85N |
| TNFRIx-R29 | F89I |
| TNFRIx-R30 | F89V |
| TNFRIx-R31 | E93Q |
| TNFRIx-R32 | E93N |
| TNFRIx-R33 | L96I |
| TNFRIx-R34 | L96V |
| TNFRIx-R35 | R97H |
| TNFRIx-R36 | R97Q |
| TNFRIx-R37 | L100I |
| TNFRIx-R38 | L100V |
| TNFRIx-R39 | K104Q |
| TNFRIx-R40 | K104N |
| TNFRIx-R41 | R106H |
| TNFRIx-R42 | R106Q |
| TNFRIx-R43 | K107Q |
| TNFRIx-R44 | K107N |
| TNFRIx-R45 | E108Q |
| TNFRIx-R46 | E108N |

TABLE 6-continued

| List of Designed TNFRI Mutant | |
|---|---|
| Mutant No. | Mutation |
| TNFRIx-R47 | M109I |
| TNFRIx-R48 | M109V |
| TNFRIx-R49 | E113Q |
| TNFRIx-R50 | E113N |
| TNFRIx-R51 | D120N |
| TNFRIx-R52 | D120Q |
| TNFRIx-R53 | R121H |
| TNFRIx-R54 | R121Q |
| TNFRIx-R55 | D122N |
| TNFRIx-R56 | D122Q |
| TNFRIx-R57 | R128H |
| TNFRIx-R58 | R128Q |
| TNFRIx-R59 | K129Q |
| TNFRIx-R60 | K129N |
| TNFRIx-R61 | Y132I |
| TNFRIx-R62 | Y132H |
| TNFRIx-R63 | R133H |
| TNFRIx-R64 | R133Q |
| TNFRIx-R65 | Y135I |
| TNFRIx-R66 | Y135H |
| TNFRIx-R67 | W136H |
| TNFRIx-R68 | W136S |
| TNFRIx-R69 | E138Q |
| TNFRIx-R70 | E138N |
| TNFRIx-R71 | L140I |
| TNFRIx-R72 | L140V |
| TNFRIx-R73 | F141I |
| TNFRIx-R74 | F141V |
| TNFRIx-R75 | F144I |
| TNFRIx-R76 | F144V |
| TNFRIx-R77 | L150I |
| TNFRIx-R78 | L150V |
| TNFRIx-R79 | L156I |
| TNFRIx-R80 | L156V |
| TNFRIx-R81 | E160Q |
| TNFRIx-R82 | E160N |
| TNFRIx-R83 | K161Q |
| TNFRIx-R84 | K161N |
| TNFRIx-R85 | E200Q |
| TNFRIx-R86 | E200N |
| TNFRIx-R87 | K203Q |
| TNFRIx-R88 | K203N |
| TNFRIx-R89 | E206Q |
| TNFRIx-R90 | E206N |
| TNFRIx-R91 | D207Q |
| TNFRIx-R92 | D207N |

(*In the context of the following examples, the symbol x represents 108, 126, or 171 for mutant Nos. R1 to R76, 126 or 171 for mutant Nos. R77 to R84, and 171 for mutant Nos. R85 to R92. The symbol "R" stands for protease resistance-increased mutant candidate. For example, TNFRIx-R1 means a TNFRIx mutant candidate No. 1 that is expected to have increased protease resistance).

(2) Construction of TNFRI108 Gene and Expression Vector

To express soluble TNFRI108 protein in *E. coli*, a commercially available vector pET44a (Novagen, Cat. No: 71122-3) was used to constitute an expression vector.

Specifically, the TNFRI108 gene was obtained by PCR in the presence of the following primers using as a template the pGEM-TNFRI171 plasmid constructed in Preparation Example 1. The gene was designed to have the restriction enzyme sites Sma I and Hind III at 5' and 3' termini, respectively, which allow to clone the gene into the pET44a vector.

Forward Primer:

(SEQ ID NO: 172)

5'-
ccccggggcgatgacgatgacaaagatagcgtgtgcccg-3'

Reverse Primer:

(SEQ ID NO: 173)

5'- taagcttattacagggagcaattaaaacactgg-3'

PCR was performed as in (2) of [Preparation Example 1]. Into the pcDNA3.3 TOPO TA vector (Invitrogen, Cat. No: K8300-01), 2 μL of the PCR product was inserted according to the instructions of the manufacturer. 2 μl of the reaction solution was taken and added to an XL1-blue competent cell (RBC, Cat. No: RH119-J80), which was then transformed by applying heat shock at 42° C. for 1 minute, followed by static culture in an LB solid medium containing ampicillin to obtain a colony. The colony was cultured in an LB liquid medium containing ampicillin, the plasmid was isolated therefrom and gene sequence was confirmed with fluorescent ddNTP (Solgent, Korea). The resulting recombinant plasmid was named pcDNA3.3-TNFRI108.

Figure 5:
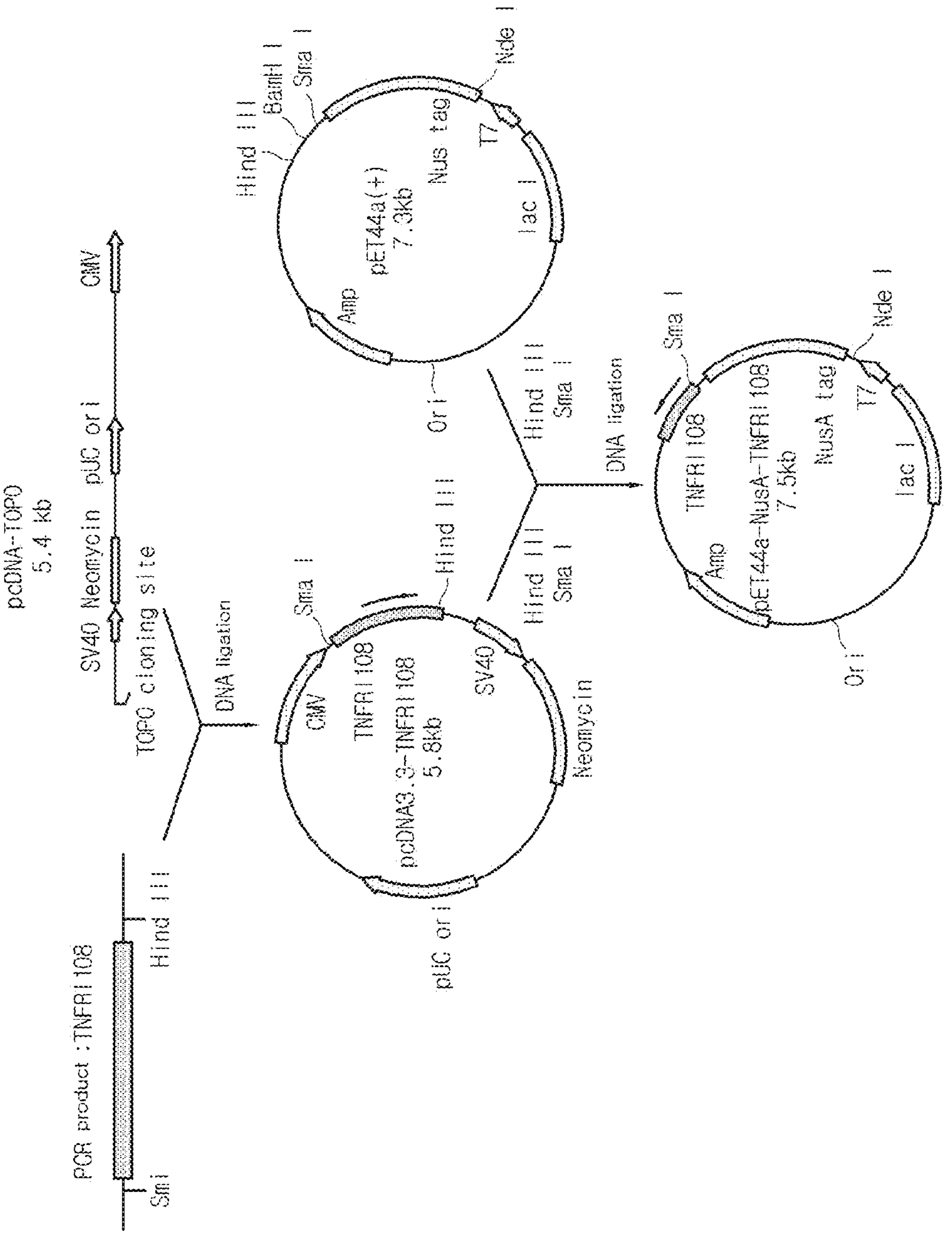
FIG. 5 is a schematic diagram illustrating the construction of a TNFRI108 expression vector for *E. coli*, by inserting a TNFRI108 gene into a pET44a vector carrying a NusA gene.

The above-prepared pcDNA3.3-TNFRI108 and pET44a were separately treated with restriction enzymes (Sma I, Hind III) at 37° C. for 3 hours. After enzymatic digestion, the digests were run on 1% agarose gel by electrophoresis, and DNA bands detected at the pertinent sizes were excised with a razor and extracted using a DNA extraction kit (GeneAll, Cat. No: 102-102). The pET44a vector was ligated with TNFRI108 gene in the presence of a ligase (NEB, Cat. No: M2200S). 2 μl of the reaction solution was taken and added to an XL1-blue competent cell (RBC, Cat. No: RH119-J80), which was then transformed by applying heat shock at 37° C. for 2 minutes, followed by static culture in an LB solid medium containing ampicillin to obtain a colony. The colony was cultured in an LB liquid medium containing ampicillin, the plasmid was isolated therefrom to construct a TNFRI108 expression vector (FIG. 5). The resulting recombinant expression vector was named pET44a-NusA-TNFRI108.

(3) Construction of DNA Encoding TNFRI108 Single Mutants

Site-specific TNFRI108 single mutants were constructed using site-directed mutagenesis. Primers that were employed for the construction of TNFRI108 single mutants are summarized in Table 7, below.

DNAs coding for the TNFRI108 single mutants were constructed in the same manner as in (2) of [Preparation Example 2], with the exception that the pET44a-NusA-TNFRI108 plasmid was used as a template in the presence of each of the primer pairs for mutants R1-R76 of Table 7.

TABLE 7

Primer for Site-Directed Mutagenesis

| Mutant No. | Mutation | Primer Direction | Primer Sequence |
|---|---|---|---|
| TNFRI-R1 | K48Q | Forward | 5'-atagcgtgtgcccgcagggtcagtatattcatcc-3' (SEQ ID NO: 174) |
| | | Reverse | 5'-ggatgaatatactgaccctgcgggcacacgctat-3' (SEQ ID NO: 175) |
| TNFRI-R2 | K48N | Forward | 5'-gtgtgcccgcagggtaactatattcatccgcaaa-3' (SEQ ID NO: 176) |
| | | Reverse | 5'-tttgcggatgaatatagttaccctgcgggcacac-3' (SEQ ID NO: 177) |
| TNFRI-R3 | Y49I | Forward | 5'-gcccgcagggtaagattattcatccgcaaaat-3' (SEQ ID NO: 178) |
| | | Reverse | 5'-attttgcggatgaataatcttaccctgcgggc-3' (SEQ ID NO: 179) |
| TNFRI-R4 | Y49H | Forward | 5'-gtgcccgcagggtaagcatattcatccgcaaaat-3' (SEQ ID NO: 180) |
| | | Reverse | 5'-attttgcggatgaatatgcttaccctgcgggcac-3' (SEQ ID NO: 181) |
| TNFRI-R5 | P52A | Forward | 5'-cgcagggtaagtatattcatgcgcaaaataactc-3' (SEQ ID NO: 182) |
| | | Reverse | 5'-gagttattttgcgcatgaatatacttaccctgcg-3' (SEQ ID NO: 183) |

TABLE 7-continued

Primer for Site-Directed Mutagenesis

| Mutant No. | Mutation | Primer Direction | Primer Sequence |
|---|---|---|---|
| TNFRI-R6 | P52S | Forward | 5'-gggtaagtatattcatagccaaaataactctatc-3' (SEQ ID NO: 184) |
| | | Reverse | 5'-gatagagttattttggctatgaatatacttaccc-3' (SEQ ID NO: 185) |
| TNFRI-R7 | K61Q | Forward | 5'-taactctatctgttgcacacagtgtcacaaaggg-3' (SEQ ID NO: 186) |
| | | Reverse | 5'-ccctttgtgacactgtgtgcaacagatagagtta-3' (SEQ ID NO: 187) |
| TNFRI-R8 | K61N | Forward | 5'-ctctatctgttgcacaaactgtcacaaagggac-3' (SEQ ID NO: 188) |
| | | Reverse | 5'-gtccctttgtgacagtttgtgcaacagatagag-3' (SEQ ID NO: 189) |
| TNFRI-R9 | K64Q | Forward | 5'-gcacaaagtgtcaccaggggacgtacctgtat-3' (SEQ ID NO: 190) |
| | | Reverse | 5'-atacaggtacgtcccctggtgacactttgtgc-3' (SEQ ID NO: 191) |
| TNFRI-R10 | K64N | Forward | 5'-gcacaaagtgtcacaacgggacgtacctgtata-3' (SEQ ID NO: 192) |
| | | Reverse | 5'-tatacaggtacgtcccgttgtgacactttgtgc-3' (SEQ ID NO: 193) |
| TNFRI-R11 | Y67I | Forward | 5'-gtcacaaagggacgattctgtataatgactgtc-3' (SEQ ID NO: 194) |
| | | Reverse | 5'-gacagtcattatacagaatcgtccctttgtgac-3' (SEQ ID NO: 195) |
| TNFRI-R12 | Y67H | Forward | 5'-gtgtcacaaagggacgcatctgtataatgactg-3' (SEQ ID NO: 196) |
| | | Reverse | 5'-cagtcattatacagatgcgtccctttgtgacac-3' (SEQ ID NO: 197) |
| TNFRI-R13 | L68I | Forward | 5'-cacaaagggacgtacatttataatgactgtccgg-3' (SEQ ID NO: 198) |
| | | Reverse | 5'-ccggacagtcattataaatgtacgtccctttgtg-3' (SEQ ID NO: 199) |
| TNFRI-R14 | L68V | Forward | 5'-gtgtcacaaagggacgcatctgtataatgactg-3' (SEQ ID NO: 200) |
| | | Reverse | 5'-cagtcattatacagatgcgtccctttgtgacac-3' (SEQ ID NO: 201) |
| TNFRI-R15 | Y69I | Forward | 5'-caaagggacgtacctgattaatgactgtccgggg-3' (SEQ ID NO: 202) |

TABLE 7-continued

Primer for Site-Directed Mutagenesis

| Mutant No. | Mutation | Primer Direction | Primer Sequence |
|---|---|---|---|
| | | Reverse | 5'-ccccggacagtcattaatcaggtacgtccctttg-3' (SEQ ID NO: 203) |
| TNFRI-R16 | Y69H | Forward | 5'-caaagggacgtacctgcataatgactgtccggg-3' (SEQ ID NO: 204) |
| | | Reverse | 5'-cccggacagtcattatgcaggtacgtccctttg-3' (SEQ ID NO: 205) |
| TNFRI-R17 | D71N | Forward | 5'-gggacgtacctgtataataactgtccggggc-3' (SEQ ID NO: 206) |
| | | Reverse | 5'-gccccggacagttattatacaggtacgtccc-3' (SEQ ID NO: 207) |
| TNFRI-R18 | D71Q | Forward | 5'-gggacgtacctgtataatcagtgtccggggcc-3' (SEQ ID NO: 208) |
| | | Reverse | 5'-ggccccggacactgattatacaggtacgtccc-3' (SEQ ID NO: 209) |
| TNFRI-R19 | D78N | Forward | 5'-ggggccgggtcagaacaccgactgccgcg-3' (SEQ ID NO: 210) |
| | | Reverse | 5'-cgcggcagtcggtgttctgacccggccc-3' (SEQ ID NO: 211) |
| TNFRI-R20 | D78Q | Forward | 5'-gggccgggtcagcagaccgactgccgc-3' (SEQ ID NO: 212) |
| | | Reverse | 5'-gcggcagtcggtctgctgacccggccc-3' (SEQ ID NO: 213) |
| TNFRI-R21 | D80N | Forward | 5'-gggtcaggataccaactgccgcgagtg-3' (SEQ ID NO: 214) |
| | | Reverse | 5'-cactcgcggcagttggtatcctgaccc-3' (SEQ ID NO: 215) |
| TNFRI-R22 | D80Q | Forward | 5'-gggtcaggatacccagtgccgcgagtgcg-3' (SEQ ID NO: 216) |
| | | Reverse | 5'-cgcactcgcggcactgggtatcctgaccc-3' (SEQ ID NO: 217) |
| TNFRI-R23 | R82H | Forward | 5'-ggataccgactgccatgagtgcgagagtggg-3' (SEQ ID NO: 218) |
| | | Reverse | 5'-cccactctcgcactcatggcagtcggtatcc-3' (SEQ ID NO: 219) |
| TNFRI-R24 | R82Q | Forward | 5'-ggataccgactgccaggagtgcgagagtgg-3' (SEQ ID NO: 220) |
| | | Reverse | 5'-ccactctcgcactcctggcagtcggtatcc-3' (SEQ ID NO: 221) |
| TNFRI-R25 | E83Q | Forward | 5'-accgactgccgccagtgcgagagtg-3' (SEQ ID NO: 222) |
| | | Reverse | 5'-cactctcgcactggcggcagtcggt-3' (SEQ ID NO: 223) |
| TNFRI-R26 | E83N | Forward | 5'-ataccgactgccgcaactgcgagagtgggtc-3' (SEQ ID NO: 224) |
| | | Reverse | 5'-gacccactctcgcagttgcggcagtcggtat-3' (SEQ ID NO: 225) |
| TNFRI-R27 | E85Q | Forward | 5'-ctgccgcgagtgccagagtgggtcatt-3' (SEQ ID NO: 226) |
| | | Reverse | 5'-aatgacccactctggcactcgcggcag-3' (SEQ ID NO: 227) |

TABLE 7-continued

Primer for Site-Directed Mutagenesis

| Mutant No. | Mutation | Primer Direction | Primer Sequence |
|---|---|---|---|
| TNFRI-R28 | E85N | Forward | 5'-gactgccgcgagtgcaacagtgggtcatttacag-3' (SEQ ID NO: 228) |
| | | Reverse | 5'-ctgtaaatgacccactgttgcactcgcggcagtcg-3' (SEQ ID NO: 229) |
| TNFRI-R29 | F89I | Forward | 5'-gtgcgagagtgggtcaattacagcgagtgag-3' (SEQ ID NO: 230) |
| | | Reverse | 5'-ctcactcgctgtaattgacccactctcgcac-3' (SEQ ID NO: 231) |
| TNFRI-R30 | F89V | Forward | 5'-cgagtgcgagagtgggtcagtgacagcgagtg-3' (SEQ ID NO: 232) |
| | | Reverse | 5'-cactcgctgtcactgacccactctcgcactcg-3' (SEQ ID NO: 233) |
| TNFRI-R31 | E93Q | Forward | 5'-gtgggtcatttacagcgagtcagaatcatctgcg-3' (SEQ ID NO: 234) |
| | | Reverse | 5'-cgcagatgattctgactcgctgtaaatgacccac-3' (SEQ ID NO: 235) |
| TNFRI-R32 | E93N | Forward | 5'-gtcatttacagcgagtaacaatcatctgcgccac-3' (SEQ ID NO: 236) |
| | | Reverse | 5'-gtggcgcagatgattgttactcgctgtaaatgac-3' (SEQ ID NO: 237) |
| TNFRI-R33 | L96I | Forward | 5'-gcgagtgagaatcatattcgccactgcctgagc-3' (SEQ ID NO: 238) |
| | | Reverse | 5'-gctcaggcagtggcgaatatgattctcactcgc-3' (SEQ ID NO: 239) |
| TNFRI-R34 | L96V | Forward | 5'-tacagcgagtgagaatcatgtgcgccactgc-3' (SEQ ID NO: 240) |
| | | Reverse | 5'-gcagtggcgcacatgattctcactcgctgta-3' (SEQ ID NO: 241) |
| TNFRI-R35 | R97H | Forward | 5'-gagtgagaatcatctgcatcactgcctgagctg-3' (SEQ ID NO: 242) |
| | | Reverse | 5'-cagctcaggcagtgatgcagatgattctcactc-3' (SEQ ID NO: 243) |
| TNFRI-R36 | R97Q | Forward | 5'-gagtgagaatcatctgcagcactgcctgagctg-3' (SEQ ID NO: 244) |
| | | Reverse | 5'-cagctcaggcagtgctgcagatgattctcactc-3' (SEQ ID NO: 245) |
| TNFRI-R37 | L100I | Forward | 5'-catctgcgccactgcattagctgttctaagtgtc-3' (SEQ ID NO: 246) |

TABLE 7-continued

| Primer for Site-Directed Mutagenesis | | | |
|---|---|---|---|
| Mutant No. | Mutation | Primer Direction | Primer Sequence |
| | | Reverse | 5'-gacacttagaacagctaatgcagtggcgcagatg-3' (SEQ ID NO: 247) |
| TNFRI-R38 | L100V | Forward | 5'-catctgcgccactgcgtgagctgttctaag-3' (SEQ ID NO: 248) |
| | | Reverse | 5'-cttagaacagctcacgcagtggcgcagatg-3' (SEQ ID NO: 249) |
| TNFRI-R39 | K104Q | Forward | 5'-cgccactgcctgagctgttctcagtgtcgtaaa-3' (SEQ ID NO: 250) |
| | | Reverse | 5'-tttacgacactgagaacagctcaggcagtggcg-3' (SEQ ID NO: 251) |
| TNFRI-R40 | K104N | Forward | 5'-cactgcctgagctgttctaactgtcgtaaagag-3' (SEQ ID NO: 252) |
| | | Reverse | 5'-ctctttacgacagttagaacagctcaggcagtg-3' (SEQ ID NO: 253) |
| TNFRI-R41 | R106H | Forward | 5'-gctgttctaagtgtcataaagagatgggccaag-3' (SEQ ID NO: 254) |
| | | Reverse | 5'-cttggcccatctctttatgacacttagaacagc-3' (SEQ ID NO: 255) |
| TNFRI-R42 | R106Q | Forward | 5'-gctgttctaagtgtcagaaagagatgggccaag-3' (SEQ ID NO: 256) |
| | | Reverse | 5'-cttggcccatctctttctgacacttagaacagc-3' (SEQ ID NO: 257) |
| TNFRI-R43 | K107Q | Forward | 5'-gttctaagtgtcgtcaggagatgggccaagttg-3' (SEQ ID NO: 258) |
| | | Reverse | 5'-caacttggcccatctcctgacgacacttagaac-3' (SEQ ID NO: 259) |
| TNFRI-R44 | K107N | Forward | 5'-gttctaagtgtcgtaacgagatgggccaagttg-3' (SEQ ID NO: 260) |
| | | Reverse | 5'-caacttggcccatctcgttacgacacttagaac-3' (SEQ ID NO: 261) |
| TNFRI-R45 | E108Q | Forward | 5'-gctgttctaagtgtcgtaaacagatgggccaag-3' (SEQ ID NO: 262) |
| | | Reverse | 5'-cttggcccatctgtttacgacacttagaacagc-3' (SEQ ID NO: 263) |
| TNFRI-R46 | E108N | Forward | 5'-gttctaagtgtcgtaaaaacatgggccaagttg-3' (SEQ ID NO: 264) |
| | | Reverse | 5'-caacttggcccatgtttttacgacacttagaac-3' (SEQ ID NO: 265) |
| TNFRI-R47 | M109I | Forward | 5'-ctaagtgtcgtaaagagattggccaagttgaaat-3' (SEQ ID NO: 266) |
| | | Reverse | 5'-atttcaacttggccaatctctttacgacacttag-3' (SEQ ID NO: 267) |

TABLE 7-continued

| Primer for Site-Directed Mutagenesis | | | |
|---|---|---|---|
| Mutant No. | Mutation | Primer Direction | Primer Sequence |
| TNFRI-R48 | M109V | Forward | 5'-ctaagtgtcgtaaagaggtgggccaagttgaaat-3' (SEQ ID NO: 268) |
| | | Reverse | 5'-atttcaacttggcccacctctttacgacacttag-3' (SEQ ID NO: 269) |
| TNFRI-R49 | E113Q | Forward | 5'-gagatgggccaagttcagatttcttcatgtacgg-3' (SEQ ID NO: 270) |
| | | Reverse | 5'-ccgtacatgaagaaatctgaacttggcccatctc-3' (SEQ ID NO: 271) |
| TNFRI-R50 | E113N | Forward | 5'-gagatgggccaagttaacatttcttcatgtacgg-3' (SEQ ID NO: 272) |
| | | Reverse | 5'-ccgtacatgaagaaatgttaacttggcccatctc-3' (SEQ ID NO: 273) |
| TNFRI-R51 | D120N | Forward | 5'-tttcttcatgtacggtaaaccgcgatacggtatg-3' (SEQ ID NO: 274) |
| | | Reverse | 5'-cataccgtatcgcggtttaccgtacatgaagaaa-3' (SEQ ID NO: 275) |
| TNFRI-R52 | D120Q | Forward | 5'-tttcttcatgtacggtacagcgcgatacggtatg-3' (SEQ ID NO: 276) |
| | | Reverse | 5'-cataccgtatcgcgctgtaccgtacatgaagaaa-3' (SEQ ID NO: 277) |
| TNFRI-R53 | R121H | Forward | 5'-catgtacggtagaccatgatacggtatgtggttg-3' (SEQ ID NO: 278) |
| | | Reverse | 5'-caaccacataccgtatcatggtctaccgtacatg-3' (SEQ ID NO: 279) |
| TNFRI-R54 | R121Q | Forward | 5'-catgtacggtagaccaggatacggtatgtggttg-3' (SEQ ID NO: 280) |
| | | Reverse | 5'-caaccacataccgtatcctggtctaccgtacatg-3' (SEQ ID NO: 281) |
| TNFRI-R55 | D122N | Forward | 5'-gtacggtagaccgcaacacggtatgtggttgcc-3' (SEQ ID NO: 282) |
| | | Reverse | 5'-ggcaaccacataccgtgttgcggtctaccgtac-3' (SEQ ID NO: 283) |
| TNFRI-R56 | D122Q | Forward | 5'-gtacggtagaccgccagacggtatgtggttgcc-3' (SEQ ID NO: 284) |

TABLE 7-continued

Primer for Site-Directed Mutagenesis

| Mutant No. | Mutation | Primer Direction | Primer Sequence |
|---|---|---|---|
| | | Reverse | 5'-ggcaaccacataccgtctggcggtctaccgtac-3' (SEQ ID NO: 285) |
| TNFRI-R57 | R128H | Forward | 5'-cggtatgtggttgccataaaaaccagtatcgcc-3' (SEQ ID NO: 286) |
| | | Reverse | 5'-ggcgatactggtttttatggcaaccacataccg-3' (SEQ ID NO: 287) |
| TNFRI-R58 | R128Q | Forward | 5'-cggtatgtggttgccagaaaaaccagtatcgcc-3' (SEQ ID NO: 288) |
| | | Reverse | 5'-ggcgatactggtttttctggcaaccacataccg-3' (SEQ ID NO: 289) |
| TNFRI-R59 | K129Q | Forward | 5'-ggtatgtggttgccgtcagaaccagtatcgcc-3' (SEQ ID NO: 290) |
| | | Reverse | 5'-ggcgatactggttctgacggcaaccacatacc-3' (SEQ ID NO: 291) |
| TNFRI-R60 | K129N | Forward | 5'-ggtatgtggttgccgtaacaaccagtatcgcc-3' (SEQ ID NO: 292) |
| | | Reverse | 5'-ggcgatactggttgttacggcaaccacatacc-3' (SEQ ID NO: 293) |
| TNFRI-R61 | Y132I | Forward | 5'-gttgccgtaaaaaccagattcgccattattggtc-3' (SEQ ID NO: 294) |
| | | Reverse | 5'-gaccaataatggcgaatctggtttttacggcaac-3' (SEQ ID NO: 295) |
| TNFRI-R62 | Y132H | Forward | 5'-gttgccgtaaaaaccagcatcgccattattggtc-3' (SEQ ID NO: 296) |
| | | Reverse | 5'-gaccaataatggcgatgctggtttttacggcaac-3' (SEQ ID NO: 297) |
| TNFRI-R63 | R133H | Forward | 5'-gccgtaaaaaccagtatcatcattattggtcag-3' (SEQ ID NO: 298) |
| | | Reverse | 5'-ctgaccaataatgatgatactggtttttacggc-3' (SEQ ID NO: 299) |
| TNFRI-R64 | R133Q | Forward | 5'-gccgtaaaaaccagtatcagcattattggtcag-3' (SEQ ID NO: 300) |
| | | Reverse | 5'-ctgaccaataatgctgatactggtttttacggc-3' (SEQ ID NO: 301) |
| TNFRI-R65 | Y135I | Forward | 5'-ccagtatcgccatatttggtcagaaaacctgttc-3' (SEQ ID NO: 302) |
| | | Reverse | 5'-gaacaggttttctgaccaaatatggcgatactgg-3' (SEQ ID NO: 303) |

TABLE 7-continued

| Primer for Site-Directed Mutagenesis | | | |
|---|---|---|---|
| Mutant No. | Mutation | Primer Direction | Primer Sequence |
| TNFRI-R66 | Y135H | Forward | 5'-ccagtatcgccatcattggtcagaaaacctgttc-3' (SEQ ID NO: 304) |
| | | Reverse | 5'-gaacaggttttctgaccaatgatggcgatactgg-3' (SEQ ID NO: 305) |
| TNFRI-R67 | W136H | Forward | 5'-cagtatcgccattatcattcagaaaacctgttcc-3' (SEQ ID NO: 306) |
| | | Reverse | 5'-ggaacaggttttctgaatgataatggcgatactg-3' (SEQ ID NO: 307) |
| TNFRI-R68 | W136S | Forward | 5'-cagtatcgccattatagctcagaaaacctgttcc-3' (SEQ ID NO: 308) |
| | | Reverse | 5'-ggaacaggttttctgagctataatggcgatactg-3' (SEQ ID NO: 309) |
| TNFRI-R69 | E138Q | Forward | 5'-cgccattattggtcacagaacctgttccagtg-3' (SEQ ID NO: 310) |
| | | Reverse | 5'-cactggaacaggttctgtgaccaataatggcg-3' (SEQ ID NO: 311) |
| TNFRI-R70 | E138N | Forward | 5'-cgccattattggtcaaacaacctgttccagtg-3' (SEQ ID NO: 312) |
| | | Reverse | 5'-cactggaacaggttgtttgaccaataatggcg-3' (SEQ ID NO: 313) |
| TNFRI-R71 | L140I | Forward | 5'-attggtcagaaaacattttccagtgttttaattg-3' (SEQ ID NO: 314) |
| | | Reverse | 5'-caattaaaacactggaaaatgttttctgaccaat-3' (SEQ ID NO: 315) |
| TNFRI-R72 | L140V | Forward | 5'-attggtcagaaaacgtgttccagtgttttaattg-3' (SEQ ID NO: 316) |
| | | Reverse | 5'-caattaaaacactggaacacgttttctgaccaat-3' (SEQ ID NO: 317) |
| TNFRI-R73 | F141I | Forward | 5'-ggtcagaaaacctgattcagtgttttaattgctc-3' (SEQ ID NO: 318) |
| | | Reverse | 5'-gagcaattaaaacactgaatcaggttttctgacc-3' (SEQ ID NO: 319) |
| TNFRI-R74 | F141V | Forward | 5'-ggtcagaaaacctggtgcagtgttttaattgctc-3' (SEQ ID NO: 320) |

TABLE 7-continued

| Primer for Site-Directed Mutagenesis | | | |
|---|---|---|---|
| Mutant No. | Mutation | Primer Direction | Primer Sequence |
| | | Reverse | 5'-gagcaattaaaacactgcaccaggttttctgacc-3' (SEQ ID NO: 321) |
| TNFRI-R75 | F144I | Forward | 5'-gaaaacctgttccagtgtattaattgctccctg-3' (SEQ ID NO: 322) |
| | | Reverse | 5'-cagggagcaattaatacactggaacaggttttc-3' (SEQ ID NO: 323) |
| TNFRI-R76 | F144V | Forward | 5'-gaaaacctgttccagtgtgtgaattgctccctg-3' (SEQ ID NO: 324) |
| | | Reverse | 5'-cagggagcaattcacacactggaacaggttttc-3' (SEQ ID NO: 325) |

(4) Expression of TNFRI108 and TNFRI108 Mutants

BL21Star (DE3) (Invitrogen, Cat. No: C6010-03) competent cells were transformed with 1 μL of the constructed plasmid by heat shock at 42° C. for 1 min and incubated on LB plates to form colonies. The *E. coli* BL21Star (DE3) carrying the pET44a-NusA-TNFRI108 and TNFRI108 mutant vector therein was inoculated into 5 mL of LB broth (BD, Cat. No: 244620) containing 100 μg/mL ampicillin and incubated at 37° C. for 16 hours with aeration. The culture was inoculated into 50 mL of a medium containing 100 μg/ml ampicillin and grown to an O.D. of 0.6~0.8. IPTG (Sigma, Cat. No: 19003) was added at a final concentration of 1.0 mM to induce expression. After IPTG induction, the cells were incubated at 37° C. for an additional 3 hours with aeration and harvested by spinning at 5,000 rpm for 20 min.

(5) Purification of TNFRI108 and TNFRI108 Mutants

After disruption of the collected cells, the supernatant was primarily purified using metal affinity chromatography and then hydrophobic chromatography to proteins of interest with a purity of 90% or higher.

The harvested cells were resuspended in a solution (50 mM Tris (pH 8.5)) and disrupted with a sonicator (Sonics, Cat. No: VCX 750). After centrifugation at 12,000 rpm for 20 min, the supernatant was recovered. Hypercell resins (Pall, Cat No: 20093-010) were loaded in an amount of 300 μL/well into 96-well filter plates (Pall, Cat No: PN5065), washed with 4 column volumes of distilled water and treated with two column volumes of 0.1 M $NiCl_2$ to bind nickel ions to the resins. They were washed with two column volumes of distilled water and then equilibrated with 6 column volumes of an equilibration buffer (25 mM Tris, 0.1 M NaCl (pH 8.5)). Two column volumes of the sample were added to the resins and unbound samples were removed by flowing 4 column volumes of an equilibration buffer. After washing with 10 column volumes of a washing buffer (25 mM Tris, 0.1 M NaCl, 50 mM imidazole (pH 8.5)), TNFRI108 bound to the column was eluted with two column volumes of an eluent (25 mM Tris, 0.1 M NaCl, 250 mM imidazole (pH 8.5)).

Figure 6:
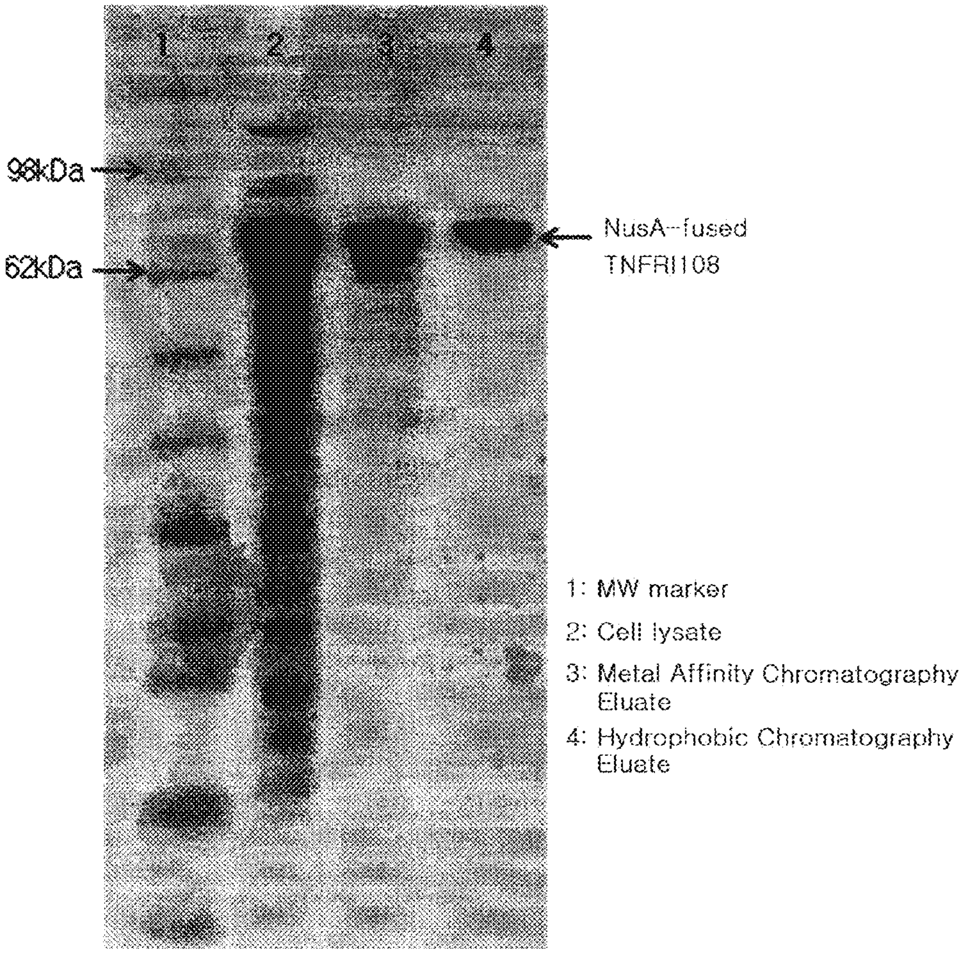
FIG. 6 is a photograph showing the expression of a NusA-fused TNFRI108 protein in *E. coli* transformed with the pET44a-NusA-TNFRI108 expression vector followed by purification by immobilized metal affinity chromatography and hydrophobic interaction chromatography.

In the protein solution eluted from the metal affinity chromatography, 1.0 M ammonium sulfate ($(NH_4)_2SO_4$) was diluted to 400 mM. Phenyl Sepharose resins (GE, Cat. No: 17-108201) were loaded in an amount of 300 μL/well into 96-well filter plates and equilibrated with 6 column volumes of an equilibration buffer (20 mM sodium phosphate ($Na_2PO_4$), 400 mM ammonium sulfate (pH 7.0)). The eluate from the metal affinity chromatography was added to the column and washed with 2 column volumes of an equilibration buffer to remove unbound proteins. After washing with 10 column volumes of a washing buffer (20 mM sodium phosphate ($Na_2PO_4$), 160 mM ammonium sulfate (pH 7.0)), elution was carried out with 6 column volumes of an eluent (20 mM sodium phosphate (pH 7.0)). The eluate was concentrated into at least 100 μg/mL before carrying out quantitative analysis using the Bradford method. Purity of all the purified samples was evaluated by SDS-PAGE (FIG. 6).

EXPERIMENTAL EXAMPLE 4

Resistance of TNFRI108 and TNFRI108 Mutants to Proteases

TNFRI108 and TNFRI108 mutants were assayed for Protease resistance. First, the total concentration of a purified protein (e.g., TNFRI108) solution was determined using the Bradford method. Swine pancreatin was used in an amount of 40% of the total protein concentration to degrade the purified protein. The half-life of each mutant according to treatment with pancreatin was determined and compared to that of the TNFRI108 polypeptide fragment.

Figure 7:
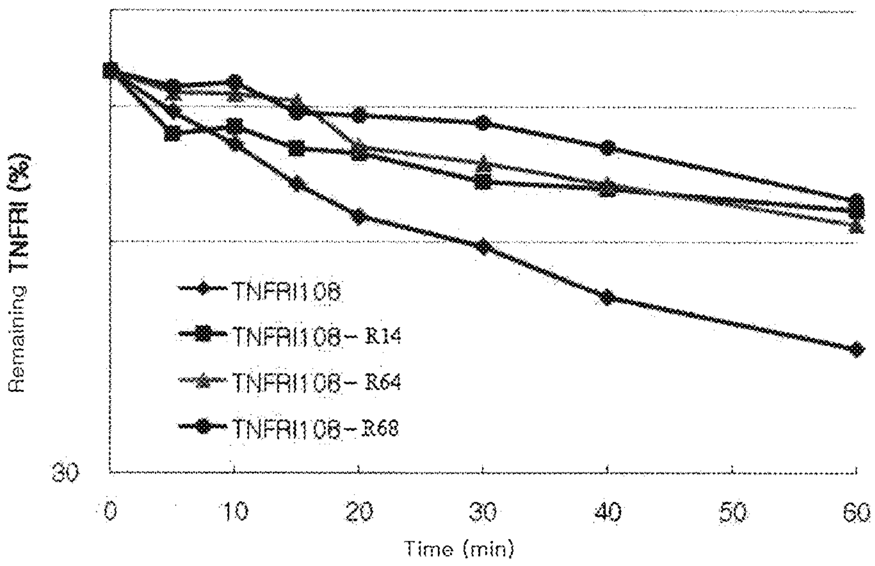
FIG. 7 is a graph showing the resistance of the TNFRI108 fragment and the TNFRI108 single mutants TNFRI108-R14, TNFRI108-R64, and TNFRI108-R68 to proteases.

In order to evaluate the resistance of TNFRI108 mutants to proteineases, half lives of the mutants were measured after treatment with pancreatin (Sigma, Cat. No: P7545) and compared to those of TNFRI108. Resistance of the representative mutants TNFRI108-R14, TNFRI108-R64 and TNFRI108-R68 to pancreatin is shown in FIG. 7. The same procedure as in [Experimental Example 3] was repeated with the exception that 250 μL of each protein sample was treated with 6 μg of pancreatin. The results are summarized in Table 8, below.

TABLE 8

| Protease Resistance of TNFRI108 Mutants (reacted at 37° C.) | |
|---|---|
| Mutant No. | Resistance compared to TNFRI108 |
| TNFRI108-R1 | 73% |

TABLE 8-continued

Protease Resistance of TNFRI108 Mutants (reacted at 37° C.)

| Mutant No. | Resistance compared to TNFRI108 |
|---|---|
| TNFRI108-R2 | 48% |
| TNFRI108-R3 | 5% |
| TNFRI108-R4 | 6% |
| TNFRI108-R5 | 26% |
| TNFRI108-R6 | 57% |
| TNFRI108-R7 | 108% |
| TNFRI108-R8 | 111% |
| TNFRI108-R9 | 43% |
| TNFRI108-R10 | 14% |
| TNFRI108-R11 | 24% |
| TNFRI108-R12 | 30% |
| TNFRI108-R13 | 166% |
| TNFRI108-R14 | 168% |
| TNFRI108-R15 | 14% |
| TNFRI108-R16 | 13% |
| TNFRI108-R17 | 17% |
| TNFRI108-R18 | 81% |
| TNFRI108-R19 | 89% |
| TNFRI108-R20 | 106% |
| TNFRI108-R21 | ND |
| TNFRI108-R22 | ND |
| TNFRI108-R23 | ND |
| TNFRI108-R24 | ND |
| TNFRI108-R25 | 75% |
| TNFRI108-R26 | 75% |
| TNFRI108-R27 | 93% |
| TNFRI108-R28 | 149% |
| TNFRI108-R29 | ND |
| TNFRI108-R30 | ND |
| TNFRI108-R31 | 70% |
| TNFRI108-R32 | 50% |
| TNFRI108-R33 | 70% |
| TNFRI108-R34 | 55% |
| TNFRI108-R35 | 80% |
| TNFRI108-R36 | 50% |
| TNFRI108-R37 | 84% |
| TNFRI108-R38 | 89% |

TABLE 8-continued

Protease Resistance of TNFRI108 Mutants (reacted at 37° C.)

| Mutant No. | Resistance compared to TNFRI108 |
|---|---|
| TNFRI108-R39 | 89% |
| TNFRI108-R40 | 90% |
| TNFRI108-R41 | 125% |
| TNFRI108-R42 | 113% |
| TNFRI108-R43 | 110% |
| TNFRI108-R44 | 96% |
| TNFRI108-R45 | 37% |
| TNFRI108-R46 | 57% |
| TNFRI108-R47 | 158% |
| TNFRI108-R48 | 103% |
| TNFRI108-R49 | 51% |
| TNFRI108-R50 | 23% |
| TNFRI108-R51 | 67% |
| TNFRI108-R52 | 71% |
| TNFRI108-R53 | 116% |
| TNFRI108-R54 | 119% |
| TNFRI108-R55 | 83% |
| TNFRI108-R56 | 28% |
| TNFRI108-R57 | 141% |
| TNFRI108-R58 | 116% |
| TNFRI108-R59 | 86% |
| TNFRI108-R60 | 84% |
| TNFRI108-R61 | 96% |
| TNFRI108-R62 | 89% |
| TNFRI108-R63 | 91% |
| TNFRI108-R64 | 213% |
| TNFRI108-R65 | 171% |
| TNFRI108-R66 | 111% |
| TNFRI108-R67 | 109% |
| TNFRI108-R68 | 288% |
| TNFRI108-R69 | 107% |
| TNFRI108-R70 | 105% |
| TNFRI108-R71 | 74% |
| TNFRI108-R72 | 103% |
| TNFRI108-R73 | 176% |
| TNFRI108-R74 | 158% |
| TNFRI108-R75 | 83% |

TABLE 8-continued

| Protease Resistance of TNFRI108 Mutants (reacted at 37° C.) | |
|---|---|
| Mutant No. | Resistance compared to TNFRI108 |
| TNFRI108-R76 | 97% |

(ND: Not Detected)

(6) Construction of Expression Vectors Carrying Met-TNFRI126 and Met-TNFRI126 Mutants The protease resistance of the single mutants, confirmed in TNFRI108, was also established for the Met-TNFRI126 and Met-TNFRI126 mutants. In this context, TNFRI108-R7, TNFRI108-R8, TNFRI108-R9, TNFRI108-R10, TNFRI108-R14, TNFRI108-R64, TNFRI108-R65, TNFRI108-R68, TNFRI108-R73, and TNFRI108-R74 were expressed in the form of Met-TNFRI126 to examine their resistance to proteases.

Plasmids carrying Met-TNFRI126 and Met-TNFRI126 mutants were constructed in the same manner as in (2) of [Preparation Example 2] with the exception that the pET44a-Met-TNFRI126 plasmid constructed in [Preparation Example 1] was used as a template in the presence of each of primer pairs corresponding to mutant Nos. R7, R8, R9, R10, R14, R64, R65, R68, R73 and R74 of Table 7.

(7) Production and Purification of Met-TNFRI126 and Met-TNFRI126 Mutants

Met-TNFRI126 and Met-TNFRI126 mutants were prepared and purified in the same manner as in (3) of [Preparation Example 2] with the exception that 1 μL of each of the plasmids constructed above was used.

EXPERIMENTAL EXAMPLE 5

Resistance of Met-TNFRI126 and Met-TNFRI126 Mutants to Proteases

Protease resistance was assayed in the same manner as in [Experimental Example 4] with the exception that Met-TNFRI126 and Met-TNFRI126 mutants were employed instead of TNFRI108 (Table 9). High protease resistance was also detected in R14, R64, R68, R73 and R74, which were observed to have high protease resistance in TNFRI108 while R9 and R10, which exhibited low protease resistance in TNFR108, were measured to have low resistance as well.

TABLE 9

| Protease Resistance Relative to Met-TNFRI126 | |
|---|---|
| Mutant No. | Resistance Relative to Met-TNFRI126 (%) |
| TNFRI126-R7 | 87% |
| TNFRI126-R8 | 95% |
| TNFRI126-R9 | 65% |
| TNFRI126-R10 | 30% |
| TNFRI126-R14 | 143% |
| TNFRI126-R64 | 152% |
| TNFRI126-R65 | 99% |
| TNFRI126-R68 | 120% |
| TNFRI126-R73 | 159% |
| TNFRI126-R74 | 169% |

(8) Construction of Expression Vectors Carrying Met-TNFRI171 and Met-TNFRI171 Mutants Single mutants resulting from a mutation in the fourth domain of TNFRI were chosen from the designed single mutants listed in Table 6 of (1) of [Preparation Example 3], and prepared in the form of Met-TNFRI171.

For this, expression vectors for expressing Met-TNFRI171 and Met-TNFRI171 mutants in *E. coli* were constructed. Genes encoding the Met-TNFRI171 mutants were constructed by PCR using the primers for the mutants shown in Table 10, below, with the pET44a-Met-TNFRI171 plasmid serving as a template.

Plasmids carrying Met-TNFRI171 and Met-TNFRI171 mutants were constructed in the same manner as in (2) of [Preparation Example 2] with the exception that the pET44a-Met-TNFRI171 plasmid constructed in [Preparation Example 1] was used as a template in the presence of each of primer pairs shown in Table 10.

TABLE 10

| Primers for Site-Directed Mutagenesis | | | |
|---|---|---|---|
| Mutant No. | Mutation | Primer Direction | Primer Sequence |
| TNFRI-R77 | L150I | Forward | 5'-aattgctccctgtgtattaacggcactgtgcatc-3' (SEQ ID NO: 326) |
| | | Reverse | 5'-gatgcacagtgccgttaatacacagggagcaatt-3' (SEQ ID NO: 327) |
| TNFRI-R78 | L150V | Forward | 5'-ttaattgctccctgtgtgtgaacggcactgtgca-3' (SEQ ID NO: 328) |
| | | Reverse | 5'-tgcacagtgccgttcacacacagggagcaattaa-3' (SEQ ID NO: 329) |
| TNFRI-R79 | L156I | Forward | 5'-gaacggcactgtgcatatttcctgtcaggagaag-3' (SEQ ID NO: 330) |

TABLE 10-continued

Primers for Site-Directed Mutagenesis

| Mutant No. | Mutation | Primer Direction | Primer Sequence |
|---|---|---|---|
| | | Reverse | 5'-cttctcctgacaggaaatatgcacagtgccgttc-3' (SEQ ID NO: 331) |
| TNFRI-R80 | L156V | Forward | 5'-tgaacggcactgtgcatgtgtcctgtcaggagaa-3' (SEQ ID NO: 332) |
| | | Reverse | 5'-ttctcctgacaggacacatgcacagtgccgttca-3' (SEQ ID NO: 333) |
| TNFRI-R81 | E160Q | Forward | 5'-gcatctgtcctgtcagcagaagcagaatacagtt-3' (SEQ ID NO: 334) |
| | | Reverse | 5'-aactgtattctgcttctgctgacaggacagatgc-3' (SEQ ID NO: 335) |
| TNFRI-R82 | E160N | Forward | 5'-gcatctgtcctgtcagaacaagcagaatacagtt-3' (SEQ ID NO: 336) |
| | | Reverse | 5'-aactgtattctgcttgttctgacaggacagatgc-3' (SEQ ID NO: 337) |
| TNFRI-R83 | K161Q | Forward | 5'-atctgtcctgtcaggagcagcagaatacagtttg-3' (SEQ ID NO: 338) |
| | | Reverse | 5'-caaactgtattctgctgctcctgacaggacagat-3' (SEQ ID NO: 339) |
| TNFRI-R84 | K161N | Forward | 5'-ctgtcctgtcaggagaaccagaatacagtttgta-3' (SEQ ID NO: 340) |
| | | Reverse | 5'-tacaaactgtattctggttctcctgacaggacag-3' (SEQ ID NO: 341) |
| TNFRI-R85 | E200Q | Forward | 5'-ttgtgcctaccccagattcagaatgttaagggca-3' (SEQ ID NO: 342) |
| | | Reverse | 5'-tgcccttaacattctgaatctggggtaggcacaa-3' (SEQ ID NO: 343) |
| TNFRI-R86 | E200N | Forward | 5'-gtgcctaccccagattaacaatgttaagggcact-3' (SEQ ID NO: 344) |
| | | Reverse | 5'-agtgcccttaacattgttaatctggggtaggcac-3' (SEQ ID NO: 345) |
| TNFRI-R87 | K203Q | Forward | 5'-ccccagattgagaatgttcagggcactgaggac-3' (SEQ ID NO: 346) |

TABLE 10-continued

| Primers for Site-Directed Mutagenesis | | | |
|---|---|---|---|
| Mutant No. | Mutation | Primer Direction | Primer Sequence |
| | | Reverse | 5'-gtcctcagtgccctgaacattctcaatctgggg-3' (SEQ ID NO: 347) |
| TNFRI-R88 | K203N | Forward | 5'-cccagattgagaatgttaacggcactggaggactc-3' (SEQ ID NO: 348) |
| | | Reverse | 5'-gagtcctcagtgccgttaacattctcaatctggg-3' (SEQ ID NO: 349) |
| TNFRI-R89 | E206Q | Forward | 5'-ttgagaatgttaagggcactcaggactcaggcac-3' (SEQ ID NO: 350) |
| | | Reverse | 5'-gtgcctgagtcctgagtgcccttaacattctcaa-3' (SEQ ID NO: 351) |
| TNFRI-R90 | E206N | Forward | 5'-aatgttaagggcactaacgactcaggcaccacat-3' (SEQ ID NO: 352) |
| | | Reverse | 5'-atgtggtgcctgagtcgttagtgcccttaacatt-3' (SEQ ID NO: 353) |
| TNFRI-R91 | D207Q | Forward | 5'-gttaagggcactgagcagtcaggcaccacataag-3' (SEQ ID NO: 354) |
| | | Reverse | 5'-cttatgtggtgcctgactgctcagtgcccttaac-3' (SEQ ID NO: 355) |
| TNFRI-R92 | D207N | Forward | 5'-atgttaagggcactgagaactcaggcaccacata-3' (SEQ ID NO: 356) |
| | | Reverse | 5'-tatgtggtgcctgagttctcagtgcccttaacat-3' (SEQ ID NO: 357) |

(9) Production and Purification of Met-TNFRI171 and Met-TNFRI171 Mutants

Met-TNFRI171 and Met-TNFRI171 mutants were prepared and purified in the same manner as in (3) of [Preparation Example 2] with the exception that 1 μL of each of the plasmids constructed above was used.

EXPERIMENTAL EXAMPLE 6

Resistance of Met-TNFRI171 and Met-TNFRI171 Mutants to Proteases

Figure 8:
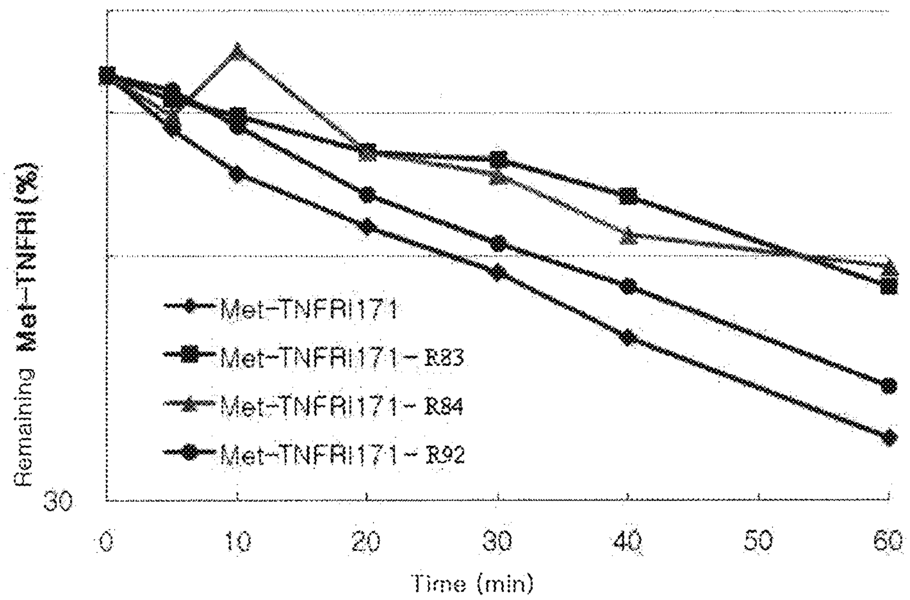
FIG. 8 is a graph showing the resistance of the Met-TNFRI171 fragment and the Met-TNFRI171 single mutants Met-TNFRI171-R83, Met-TNFRI171-R84, and Met-TNFRI171-R92 to proteases.

Protease resistance was assayed in the same manner as in [Experimental Example 3] with the exception that Met-TNFRI171 and Met-TNFRI171 mutants were employed instead of TNFRI108 (Table 11). Resistance of the representative mutants Met-TNFRI171-R83, Met-TNFRI171-R84, and Met-TNFRI171-R92 to pancreatin is shown in FIG. 8.

TABLE 11

| Protease Resistance Relative to Met-TNFRI171 | |
|---|---|
| Mutant No. | Reistance Relative to Met-TNFRI171 |
| TNFRI171-R77 | 120% |
| TNFRI171-R78 | 87% |
| TNFRI171-R79 | 113% |
| TNFRI171-R80 | 103% |
| TNFRI171-R81 | 57% |
| TNFRI171-R82 | 68% |
| TNFRI171-R83 | 187% |
| TNFRI171-R84 | 187% |
| TNFRI171-R85 | 116% |
| TNFRI171-R86 | 90% |
| TNFRI171-R87 | 111% |
| TNFRI171-R88 | 99% |
| TNFRI171-R89 | 114% |
| TNFRI171-R90 | 102% |

TABLE 11-continued

| Protease Resistance Relative to Met-TNFRI171 | |
|---|---|
| Mutant No. | Reistance Relative to Met-TNFRI171 |
| TNFRI171-R91 | 117% |
| TNFRI171-R92 | 127% |

EXAMPLE 1

Construction of Mutant with Improved Affinity for TNF-α as Well as Improved Resistance to Protease (Superlead)

(1) Design of Superlead

As evaluated in [Preparation Example 2], the mutants with improved affinity for TNF-α were highly susceptible to proteases. To confer improved Protease resistance on these mutants, the mutations for the improvement of protease resistance, confirmed in [Preparation Example 3], were combined with mutations for the improvement of affinity, as confirmed in [Preparation Example 2]. As a result, Superlead mutants were constructed according to the length of TNFRI, as shown in Tables 12 to 14.

TABLE 12

List of Designed Amino Acid Modifications in TNFRI171

| No. | Position and Kind of Amino Acid Modification |
|---|---|
| S31 | L68V, S92I, H95F, R97P, H98A |
| S32 | S92I, H95F, R97P, H98A, K161Q |
| S33 | S92I, H95F, R97P, H98A, K161N |
| S34 | S92I, H95F, R97P, H98A, E200Q |
| S35 | S92I, H95F, R97P, H98A, D207N |
| S36 | L68V, S92M, H95F, R97P, H98A |
| S37 | S92M, H95F, R97P, H98A, K161Q |
| S38 | S92M, H95F, R97P, H98A, K161N |
| S39 | S92M, H95F, R97P, H98A, E200Q |
| S40 | S92M, H95F, R97P, H98A, D207N |
| S41 | L68V, S92H, H95F, R97P, H98A |
| S42 | S92H, H95F, R97P, H98A, K161Q |
| S43 | S92H, H95F, R97P, H98A, K161N |
| S44 | S92H, H95F, R97P, H98A, E200Q |
| S45 | S92H, H95F, R97P, H98A, D207N |
| S46 | L68V, S92I, H95F, R97P, H98G |
| S47 | L68V, S92M, H95F, R97P, H98G |
| S48 | L68V, S92I, E93P, H95F, R97P, H98G |
| S49 | S92I, E93P, H95F, R97P, H98G, K161Q |
| S50 | S92I, E93P, H95F, R97P, H98G, K161N |
| S51 | S92I, E93P, H95F, R97P, H98G, E200Q |
| S52 | S92I, E93P, H95F, R97P, H98G, D207N |
| S53 | L68V, S92I, H95F, R97P, H98A, K161Q |
| S54 | L68V, S92I, H95F, R97P, H98A, K161N |
| S55 | L68V, S92I, H95F, R97P, H98A, D207N |
| S56 | L68V, S92M, H95F, R97P, H98A, K161Q |
| S57 | L68V, S92M, H95F, R97P, H98A, K161N |
| S58 | L68V, S92M, H95F, R97P, H98A, D207N |
| S59 | L68V, S92H, H95F, R97P, H98A, K161Q |
| S60 | L68V, S92H, H95F, R97P, H98A, K161N |
| S61 | L68V, S92H, H95F, R97P, H98A, D207N |
| S62 | L68V, S92I, H95F, R97P, H98G, K161Q |
| S63 | L68V, S92M, H95F, R97P, H98G, K161N |

TABLE 13

List of Designed Amino Acid Modifications in TNFRI126

| No. | Position and Kind of Amino Acid Modification |
|---|---|
| S31 | L68V, S92I, H95F, R97P, H98A |
| S36 | L68V, S92M, H95F, R97P, H98A |
| S41 | L68V, S92H, H95F, R97P, H98A |
| S46 | L68V, S92I, H95F, R97P, H98G |
| S47 | L68V, S92M, H95F, R97P, H98G |
| S48 | L68V, S92I, E93P, H95F, R97P, H98G |
| S49 | S92I, E93P, H95F, R97P, H98G, K161Q |
| S50 | S92I, E93P, H95F, R97P, H98G, K161N |
| S53 | L68V, S92I, H95F, R97P, H98A, K161Q |
| S54 | L68V, S92I, H95F, R97P, H98A, K161N |
| S56 | L68V, S92M, H95F, R97P, H98A, K161Q |
| S57 | L68V, S92M, H95F, R97P, H98A, K161N |
| S59 | L68V, S92H, H95F, R97P, H98A, K161Q |
| S60 | L68V, S92H, H95F, R97P, H98A, K161N |
| S62 | L68V, S92I, H95F, R97P, H98G, K161Q |
| S63 | L68V, S92M, H95F, R97P, H98G, K161N |

TABLE 14

List of Designed Amino Acid Modifications in TNFRI105

| No. | Position and Kind of Amino Acid Modification |
|---|---|
| S31 | L68V, S92I, H95F, R97P, H98A |
| S36 | L68V, S92M, H95F, R97P, H98A |
| S41 | L68V, S92H, H95F, R97P, H98A |
| S46 | L68V, S92I, H95F, R97P, H98G |
| S47 | L68V, S92M, H95F, R97P, H98G |

The amino acid sequences of TNFRI171, TNFRI126 and TNFRI105 mutants to which the combined mutations were applied are represented by SEQ ID NOS: 6 to 99.

(2) Construction of DNA Encoding TNFRI Mutants

Site-specific TNFRI mutants were constructed using site-directed mutagenesis. Primers that were employed for the construction of TNFRI mutants containing the amino acid mutations of Tables 12 to 14 are summarized in Table 15, below. DNAs coding for the TNFRI mutants were constructed in the same manner as in (2) of [Preparation Example 2], with the exception that the primer pairs shown in Table 15 were employed.

TABLE 15

Primers for Site-Directed Mutagenesis

| Mutation No. | Primer: PCR Template | Primer: Primer Sequence |
|---|---|---|
| S31 (pET-TNFRI_S31) | pET-TNFRI_A2 | 5'-cacaaagggacgtacgtgtataatgactgtccg-3' (SEQ ID NO: 358) 5'-cggacagtcattatacacgtacgtccctttgtg-3' (SEQ ID NO: 359) |
| S32 (pET-TNFRI_S32) | pET-TNFRI_A2 | 5'-atctgtcctgtcaggagcagcagaatacagtttg-3' (SEQ ID NO: 360) 5'-caaactgtattctgctgctcctgacaggacagat-3' (SEQ ID NO: 361) |
| S33 (pET-TNFRI_S33) | pET-TNFRI_A2 | 5'-ctgtcctgtcaggagaaccagaatacagtttgta-3' (SEQ ID NO: 362) 5'-tacaaactgtattctggttctcctgacaggacag-3' (SEQ ID NO: 363) |
| S34 (pET-TNFRI_S34) | pET-TNFRI_A2 | 5'-ttgtgcctaccccagattcagaatgttaagggca-3' (SEQ ID NO: 364) 5'-tgcccttaacattctgaatctggggtaggcacaa-3' (SEQ ID NO: 365) |
| S35 (pET-TNFRI_S35) | pET-TNFRI_A2 | 5'-atgttaagggcactgagaactcaggcaccacata-3' (SEQ ID NO: 366) 5'-tatgtggtgcctgagttctcagtgcccttaacat-3' (SEQ ID NO: 367) |
| S36 (pET-TNFRI_S36) | pET-TNFRI_A9 | 5'-cacaaagggacgtacgtgtataatgactgtccg-3' (SEQ ID NO: 368) 5'-cggacagtcattatacacgtacgtccctttgtg-3' (SEQ ID NO: 369) |
| S37 (pET-TNFRI_S37) | pET-TNFRI_A9 | 5'-atctgtcctgtcaggagcagcagaatacagtttg-3' (SEQ ID NO: 370) 5'-caaactgtattctgctgctcctgacaggacagat-3' (SEQ ID NO: 371) |
| S38 (pET-TNFRI_S38) | pET-TNFRI_A9 | 5'-ctgtcctgtcaggagaaccagaatacagtttgta-3' (SEQ ID NO: 372) 5'-tacaaactgtattctggttctcctgacaggacag-3' (SEQ ID NO: 373) |
| S39 (pET-TNFRI_S39) | pET-TNFRI_A9 | 5'-ttgtgcctaccccagattcagaatgttaagggca-3' (SEQ ID NO: 374) 5'-tgcccttaacattctgaatctggggtaggcacaa-3' (SEQ ID NO: 375) |
| S40 (pET-TNFRI_S40) | pET-TNFRI_A9 | 5'-atgttaagggcactgagaactcaggcaccacata-3' (SEQ ID NO: 376) 5'-tatgtggtgcctgagttctcagtgcccttaacat-3' (SEQ ID NO: 377) |
| S41 (pET-TNFRI_S41) | pET-TNFRI_A18 | 5'-cacaaagggacgtacgtgtataatgactgtccg-3' (SEQ ID NO: 378) 5'-cggacagtcattatacacgtacgtccctttgtg-3' (SEQ ID NO: 379) |
| S42 (pET-TNFRI_S42) | pET-TNFRI_A18 | 5'-atctgtcctgtcaggagcagcagaatacagtttg-3' (SEQ ID NO: 380) 5'-caaactgtattctgctgctcctgacaggacagat-3' (SEQ ID NO: 381) |
| S43 (pET-TNFRI_S43) | pET-TNFRI_A18 | 5'-ctgtcctgtcaggagaaccagaatacagtttgta-3' (SEQ ID NO: 382) 5'-tacaaactgtattctggttctcctgacaggacag-3' (SEQ ID NO: 383) |
| S44 (pET-TNFRI_S44) | pET-TNFRI_A18 | 5'-ttgtgcctaccccagattcagaatgttaagggca-3' (SEQ ID NO: 384) 5'-tgcccttaacattctgaatctggggtaggcacaa-3' (SEQ ID NO: 385) |
| S45 (pET-TNFRI_S45) | pET-TNFRI_A18 | 5'-atgttaagggcactgagaactcaggcaccacata-3' (SEQ ID NO: 386) 5'-tatgtggtgcctgagttctcagtgcccttaacat-3' (SEQ ID NO: 387) |

TABLE 15-continued

Primers for Site-Directed Mutagenesis

| Mutation No. | Primer PCR Template | Primer Sequence |
|---|---|---|
| S46 (pET-TNFRI_S46) | pET-TNFRI_A21 | 5'-GAGAATTTTCTGCCGGGGTGCCTGAGCTGTTCTA-3' (SEQ ID NO: 388)<br>5'-TAgaacagctcaggcaccccggcagaaaattCTC-3' (SEQ ID NO: 389) |
| S47 (pET-TNFRI_S47) | pET-TNFRI_A22 | 5'-GAGAATTTTCTGCCGGGGTGCCTGAGCTGTTCTA-3' (SEQ ID NO: 390)<br>5'-TAgaacagctcaggcaccccggcagaaaattCTC-3' (SEQ ID NO: 391) |
| S48 (pET-TNFRI_S48) | pET-TNFRI_A26 | 5'-cacaaagggacgtacgtgtataatgactgtccg-3' (SEQ ID NO: 392)<br>5'-cggacagtcattatacacgtacgtccctttgtg-3' (SEQ ID NO: 393) |
| S49 (pET-TNFRI_S49) | pET-TNFRI_A26 | 5'-atctgtcctgtcaggagcagcagaatacagtttg-3' (SEQ ID NO: 394)<br>5'-caaactgtattctgctgctcctgacaggacagat-3' (SEQ ID NO: 395) |
| S50 (pET-TNFRI_S50) | pET-TNFRI_A26 | 5'-ctgtcctgtcaggagaaccagaatacagtttgta-3' (SEQ ID NO: 396)<br>5'-tacaaactgtattctggttctcctgacaggacag-3' (SEQ ID NO: 397) |
| S51 (pET-TNFRI_S51) | pET-TNFRI_A26 | 5'-ttgtgcctaccccagattcagaatgttaagggca-3' (SEQ ID NO: 398)<br>5'-tgcccttaacattctgaatctggggtaggcacaa-3' (SEQ ID NO: 399) |
| S52 (pET-TNFRI_S52) | pET-TNFRI_A26 | 5'-atgttaagggcactgagaactcaggcaccacata-3' (SEQ ID NO: 400)<br>5'-tatgtggtgcctgagttctcagtgcccttaacat-3' (SEQ ID NO: 401) |
| S53 (pET-TNFRI_S53) | pET-TNFRI_S31 | 5'-atctgtcctgtcaggagcagcagaatacagtttg-3' (SEQ ID NO: 402)<br>5'-caaactgtattctgctgctcctgacaggacagat-3' (SEQ ID NO: 403) |
| S54 (pET-TNFRI_S54) | pET-TNFRI_S31 | 5'-ctgtcctgtcaggagaaccagaatacagtttgta-3' (SEQ ID NO: 404)<br>5'-tacaaactgtattctggttctcctgacaggacag-3' (SEQ ID NO: 405) |
| S55 (pET-TNFRI_S55) | pET-TNFRI_S31 | 5'-atgttaagggcactgagaactcaggcaccacata-3' (SEQ ID NO: 406)<br>5'-tatgtggtgcctgagttctcagtgcccttaacat-3' (SEQ ID NO: 407) |
| S56 (pET-TNFRI_S56) | pET-TNFRI_S36 | 5'-atctgtcctgtcaggagcagcagaatacagtttg-3' (SEQ ID NO: 408)<br>5'-caaactgtattctgctgctcctgacaggacagat-3' (SEQ ID NO: 409) |
| S57 (pET-TNFRI_S57) | pET-TNFRI_S36 | 5'-ctgtcctgtcaggagaaccagaatacagtttgta-3' (SEQ ID NO: 410)<br>5'-tacaaactgtattctggttctcctgacaggacag-3' (SEQ ID NO: 411) |
| S58 (pET-TNFRI_S58) | pET-TNFRI_S36 | 5'-atgttaagggcactgagaactcaggcaccacata-3' (SEQ ID NO: 412)<br>5'-tatgtggtgcctgagttctcagtgcccttaacat-3' (SEQ ID NO: 413) |
| S59 (pET-TNFRI_S59) | pET-TNFRI_S41 | 5'-atctgtcctgtcaggagcagcagaatacagtttg-3' (SEQ ID NO: 414)<br>5'-caaactgtattctgctgctcctgacaggacagat-3' (SEQ ID NO: 415) |
| S60 (pET-TNFRI_S60) | pET-TNFRI_S41 | 5'-ctgtcctgtcaggagaaccagaatacagtttgta-3' (SEQ ID NO: 416)<br>5'-tacaaactgtattctggttctcctgacaggacag-3' (SEQ ID NO: 417) |

TABLE 15-continued

| Primers for Site-Directed Mutagenesis | | |
|---|---|---|
| Mutation No. | Primer: PCR Template | Primer Sequence |
| S61 (pET-TNFRI_S61) | pET-TNFRI_S41 | 5'-atgttaagggcactgagaactcaggcaccacata-3' (SEQ ID NO: 418)<br>5'-tatgtggtgcctgagttctcagtgcccttaacat-3' (SEQ ID NO: 419) |
| S62 (pET-TNFRI_S62) | pET-TNFRI_S46 | 5'-atctgtcctgtcaggagcagcagaatacagtttg-3' (SEQ ID NO: 420)<br>5'-caaactgtattctgctgctcctgacaggacagat-3' (SEQ ID NO: 421) |
| S63 (pET-TNFRI_S63) | pET-TNFRI_S47 | 5'-ctgtcctgtcaggagaaccagaatacagtttgta-3' (SEQ ID NO: 422)<br>5'-tacaaactgtattctggttctcctgacaggacag-3' (SEQ ID NO: 423) |

(3) Production of Biologically Active Met-TNFRI and Met-TNFRI Mutants in *E. coli*

The above-constructed Met-TNFRI and Met-TNFRI mutants were produced and purified according to the method described in (3) of [Preparation Example 2].

EXPERIMENTAL EXAMPLE 7

Assay of Affinity of the Met-TNFRI Mutants for TNF-α

The affinity of the Met-TNFRI for TNF-α was assayed using the same procedure as in [Experimental Example 1] (Tables 16 to 18).

EXPERIMENTAL EXAMPLE 8

Resistance of the Met-TNFRI and Met-TNFRI Mutants to Proteases

Figure 9A:
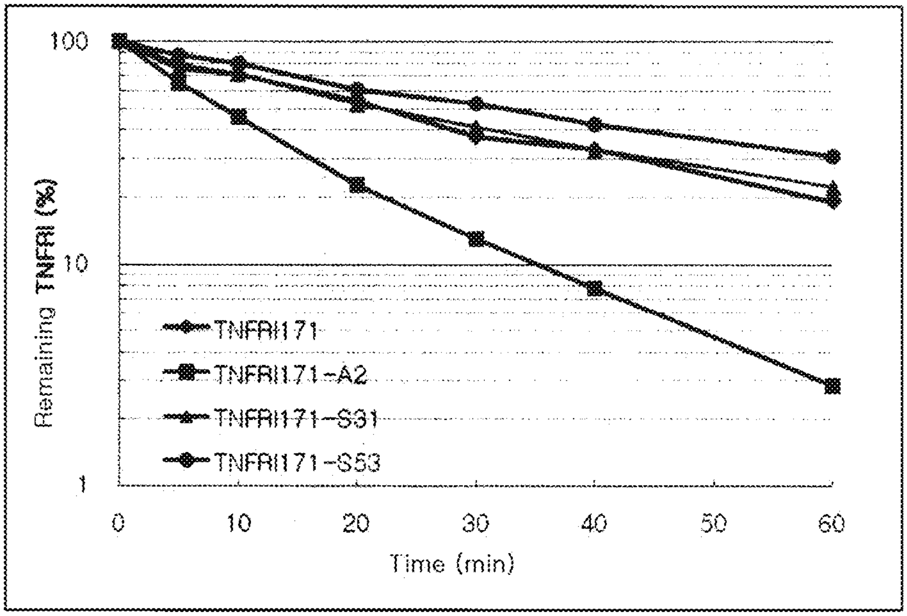
FIG. 9A is a graph showing the resistance of the TNFRI171 fragment and the TNFRI171 fragment mutants TNFRI171-A2, TNFRI171-S31, and TNFRI171-S53 to proteases.
Figure 9B:
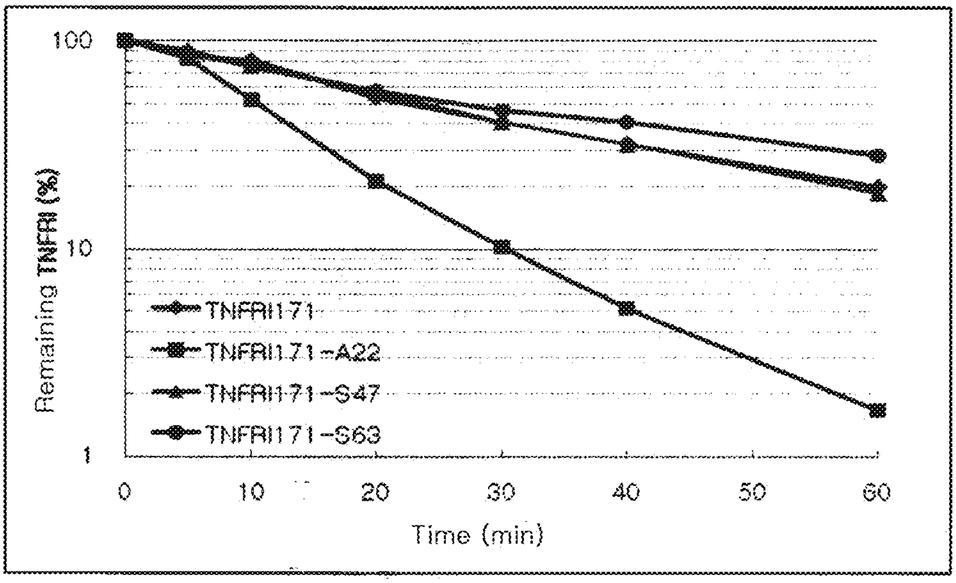
FIG. 9B is a graph showing the resistance of the TNFRI171 fragment and the TNFRI171 fragment mutants TNFRI171-A22, TNFRI171-S47 and TNFRI171-S63 to proteases.

Protease resistance was evaluated in the same manner as in [Experimental Example 3] (Tables 16 to 18). The resistance of the representative superlead mutants TNFRI171-S31, TNFRI171-S47, TNFRI171-S53 and TNFRI171-S63 to pancreatin is shown in FIG. 9. The TNFRI171 fragment was used as a control.

TABLE 16

Affinity and Protease Resistance of Superlead Mutants

| Mutant No. | Relative Affinity for Ligand (%) | Relative Protease Resistance (%) |
|---|---|---|
| Wild-type (TNFRI171) | 100 | 100 |
| TNFRI171-S31 | 563 | 97 |
| TNFRI171-S32 | 668 | 48 |
| TNFRI171-S33 | 568 | 50 |
| TNFRI171-S34 | 700 | 48 |
| TNFRI171-S35 | 521 | 44 |
| TNFRI171-S36 | 510 | 120 |

TABLE 16-continued

Affinity and Protease Resistance of Superlead Mutants

| Mutant No. | Relative Affinity for Ligand (%) | Relative Protease Resistance (%) |
|---|---|---|
| TNFRI171-S37 | 668 | 57 |
| TNFRI171-S38 | 589 | 61 |
| TNFRI171-S39 | 705 | 57 |
| TNFRI171-S40 | 773 | 56 |
| TNFRI171-S41 | 558 | 126 |
| TNFRI171-S42 | 416 | 67 |
| TNFRI171-S43 | 579 | 68 |
| TNFRI171-S44 | 694 | 69 |
| TNFRI171-S45 | 679 | 67 |
| TNFRI171-S46 | 805 | 81 |
| TNFRI171-S47 | 758 | 98 |
| TNFRI171-S48 | 594 | 36 |
| TNFRI171-S49 | 547 | 14 |
| TNFRI171-S50 | 589 | 14 |
| TNFRI171-S51 | 537 | 14 |
| TNFRI171-S52 | 626 | 15 |
| TNFRI171-S53 | 1017 | 123 |
| TNFRI171-S54 | 900 | 125 |
| TNFRI171-S55 | 973 | 85 |
| TNFRI171-S56 | 510 | 129 |
| TNFRI171-S57 | 773 | 159 |
| TNFRI171-S58 | 978 | 123 |
| TNFRI171-S59 | 684 | 148 |

TABLE 16-continued

Affinity and Protease Resistance of Superlead Mutants

| Mutant No. | Relative Affinity for Ligand (%) | Relative Protease Resistance (%) |
|---|---|---|
| TNFRI171-S60 | 775 | 132 |
| TNFRI171-S61 | 778 | 112 |
| TNFRI171-S62 | 1196 | 105 |
| TNFRI171-S63 | 1354 | 124 |

TABLE 17

Affinity and Protease Resistance of Superlead Mutants

| Mutant No. | Relative Affinity for Ligand (%) | Relative Protease Resistance (%) |
|---|---|---|
| Wild-type (TNFRI126) | 100 | 100 |
| TNFRI126-S31 | 457 | 137 |
| TNFRI126-S36 | 489 | 159 |
| TNFRI126-S41 | 432 | 157 |
| TNFRI126-S46 | 412 | 87 |
| TNFRI126-S47 | 501 | 94 |
| TNFRI126-S48 | 477 | 84 |
| TNFRI126-S53 | 522 | 156 |
| TNFRI126-S54 | 448 | 161 |
| TNFRI126-S56 | 602 | 172 |
| TNFRI126-S57 | 465 | 191 |
| TNFRI126-S59 | 463 | 171 |
| TNFRI126-S60 | 397 | 163 |
| TNFRI126-S62 | 543 | 129 |
| TNFRI126-S63 | 486 | 142 |

TABLE 18

Affinity and Protease Resistance of Superlead Mutants

| Mutant No. | Relative Affinity for Ligand (%) | Relative Protease Resistance (%) |
|---|---|---|
| Wild-type (TNFRI105) | 100 | 100 |
| TNFRI105-S31 | 453 | 153 |
| TNFRI105-S36 | 459 | 167 |
| TNFRI105-S41 | 403 | 182 |
| TNFRI105-S46 | 547 | 137 |
| TNFRI105-S47 | 497 | 143 |

EXPERIMENTAL EXAMPLE 9

Therapeutic Efficacy of 8 TNFRI171 Mutants (S54, S62, A2, A9, S36, S57, S58, S63) for Carrageenan-Induced Paw Edema in Mice In vivo the therapeutic efficacy of the mutants was determined by this experiment. Therapeutic efficacy of the mutants according to the present invention was assayed in vivo. For this, 8 mutants that exhibit high protease resistance and/or affinity for TNF-α were injected subcutaneously into mice suffering from carrageenan-induced paw edema and the size of paw edema and the level of IL-6 in the paws were measured.

0.25 mg/mL of 8 TNFRI171 mutants (TNFRI171-S54, TNFRI171-S62, TNFRI171-A2, TNFRI171-A9, TNFRI171-S36, TNFRI171-S57, TNFRI171-S58, and TNFRI171-S63), 0.25 mg/mL of wild-type (WT, TNFRI171 fragment), a vehicle (50 mM $NaPO_4$, 100 mM NaCl, pH7.0), 0.5 mg/mL of Enbrel (Wyeth) were prepared. ICR mice (20~25 g), 5 weeks old, purchased from OrientBio (CRJ) were acclimated for about 7 days in the Gyeonggi Bio-Center before use. They were allowed free access to water and foodstuff under automated conditions of temperature (23±2° C.), humidity (55±5%) and light/dark cycle (12 hours). Each group consisted of 5 mice. As an inflammation inducer, lamda-carrageenan (Sigma) was dissolved in distilled water to form a 1% solution. This carrageenan solution was administered at a dose of 50 μL into the right paw by intraplantar injection using a fine-needle syringe (BD)

The drug and the substances of interest were administered according to their PK properties. Enbrel, which has a long half-life, was administered 2 hours before the injection of carageenan while the 8 mutants, WT and the vehicle were introduced into the mice 30 min before the injection of carageenan. They were administered into the neck by subcutaneous injection (SC). Enbrel was injected at a dose of 5 mg/kg/10 mL while the injection dose of WT and the candidates was 2.5 mg/kg/10 mL.

Before and 1, 2, 3 and 4 hours after carrageenan injection, the volume of the right paw was measured using Plethysmometer (Ugo Basile). A mark was made on the ankle of the right paw before measurement so that difference on every measurement could be avoided. After the measurement of edema size for 4 hours, all the animals were euthanized with $CO_2$, and the right paws were excised and stored at −70° C. in a deep freezer (Thermo) before analysis. In order to measure the level of IL-6 in the paw tissue, the paws were thawed and finely cut using scissors and ground in 500 μL of PBS using a homogenizer. After centrifugation at 10,000 rpm for 5 min, the supernatant was divided into 100 μL for protein analysis and 200 μL for IL-6 analysis and stored at −70° C. in a deep freezer (Thermo). Quantitative analysis of the protein was carried out using the Bradford method while the level of IL-6 was determined using an ELISA kit (Komabiotech) according to the instructions of the manufacturer and normalized to the amount of protein. IL-6 levels are represented as percentages based on the vehicle group and shown in FIG. 10.

Figure 10A:
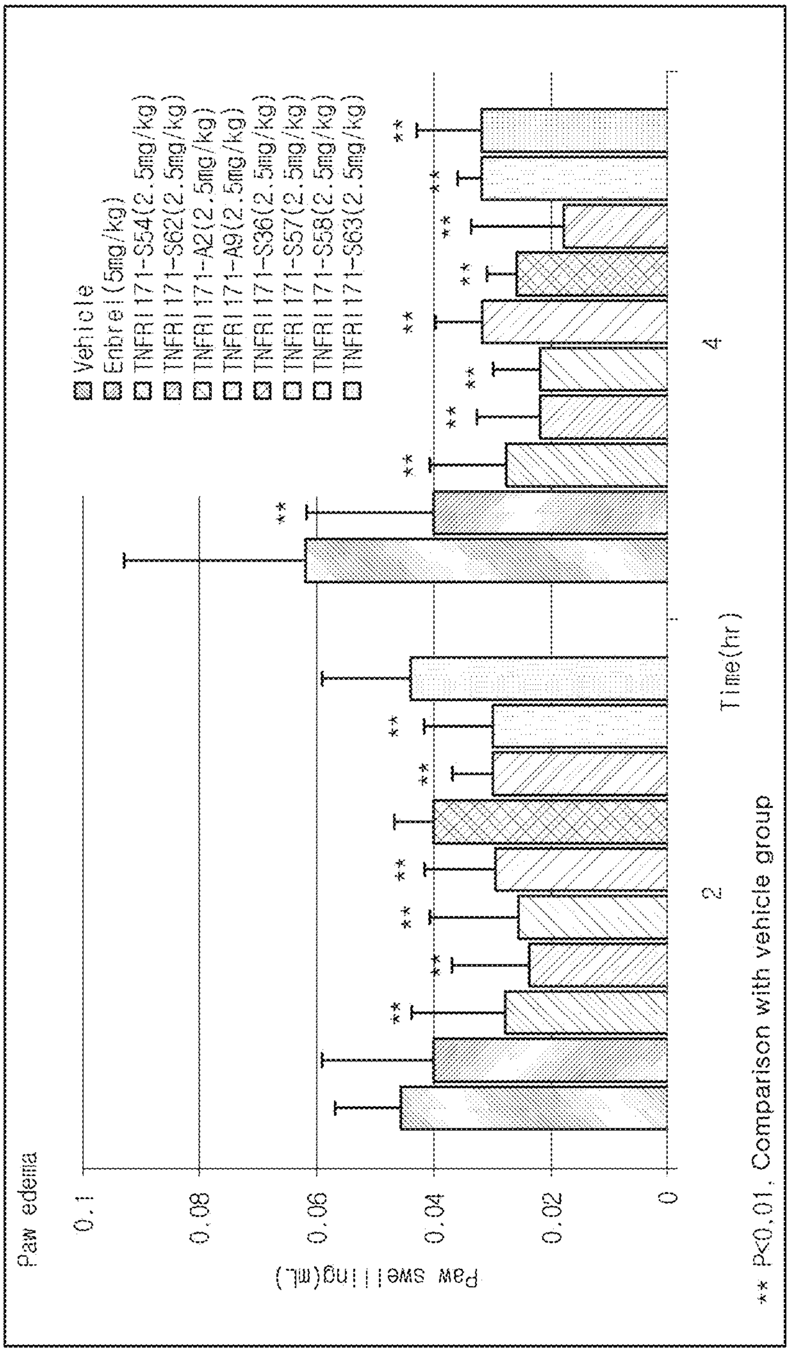
FIG. 10A is a graph showing the in vivo therapeutic effect of the TNFRI171 fragment mutants on carrageenan-induced paw edema in mice and FIG. 10B is a graph showing the levels of IL-6 in edema-induced foot tissues (vehicle, Enbrel, TNFRI171-S54, TNFRI171-S62, TNFRI171-A2, TNFRI171-A9, TNFRI171-S36, TNFRI171-S57, TNFRI171-S58, and TNFRI171-S63 from left).
Figure 10B:
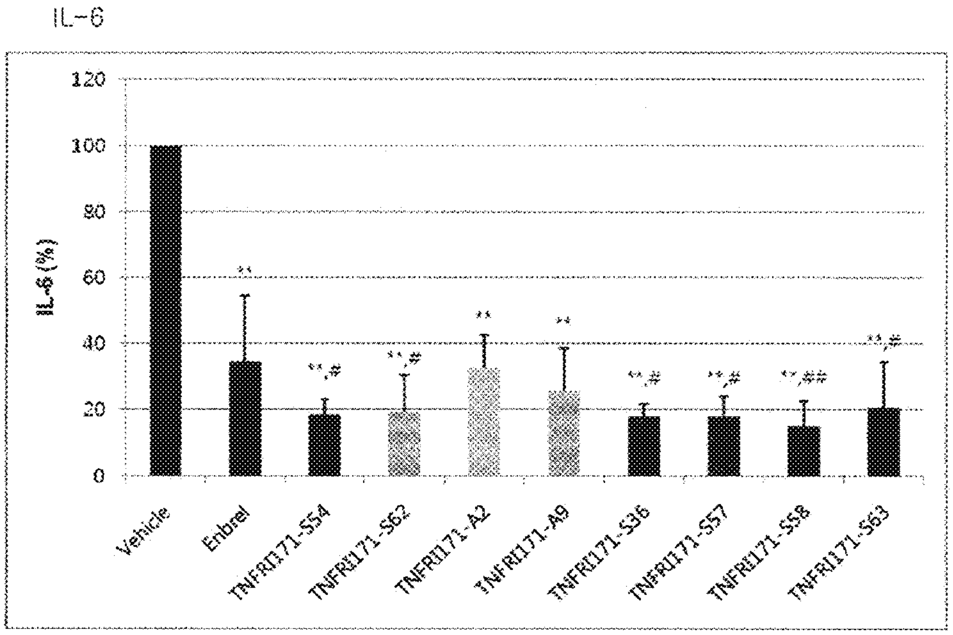

Two hours after the intraplantar injection of carrageenan, as can be seen in FIG. 10A, the edemas of all the test groups, except for the S63 group and the Ebrel group, were observed be significantly reduced in size, compared to the vehicle group. Four hours after the intraplantar injection of carrageenan, the edema in the feet of all the test groups had reduced with significance ($P<0.01$), compared to the vehicle group. As can be seen FIG. 10B, the level of the inflammatory cytokine IL-6 was significantly reduced in all the test groups, compared to the vehicle group (P<0.01), four hours after the intraplantar injection of carrageenan. The inhibitory activity against IL-6 was noticeable in S54, S62, S36, S57, S58 and S63 groups, compared to the Enbrel group, with the highest activity elicited from the S58 group (P<0.01).

EXPERIMENTAL EXAMPLE 10

Comparison of Therapeutic Efficacy for Carrageenan-Induced Paw Edema in Mice Between TNFRI171-S63 and Wild-Type (TNFRI171 Fragment)

In consideration of the physical properties and in vivo results of the TNFRI171 mutants, one (TNFRI171-S63) was selected, and compared to a vehicle (50 mM $NaPO_4$, 100 mM NaCl, pH7.0), Enbrel (Wyeth), and WT (TNFRI171 fragment). WT was formulated at 0.25 mg/mL while each of the TNFRI171-S63 mutant and Enbrel were formulated to a concentration of 0.5 mg/mL. The volume of paw edema and the level of IL-6 were measured in the same manner as in [Experimental Example 9] to evaluate the in vivo therapeutic efficacy of the mutant. The result is shown in FIG. 11.

Figure 11A:
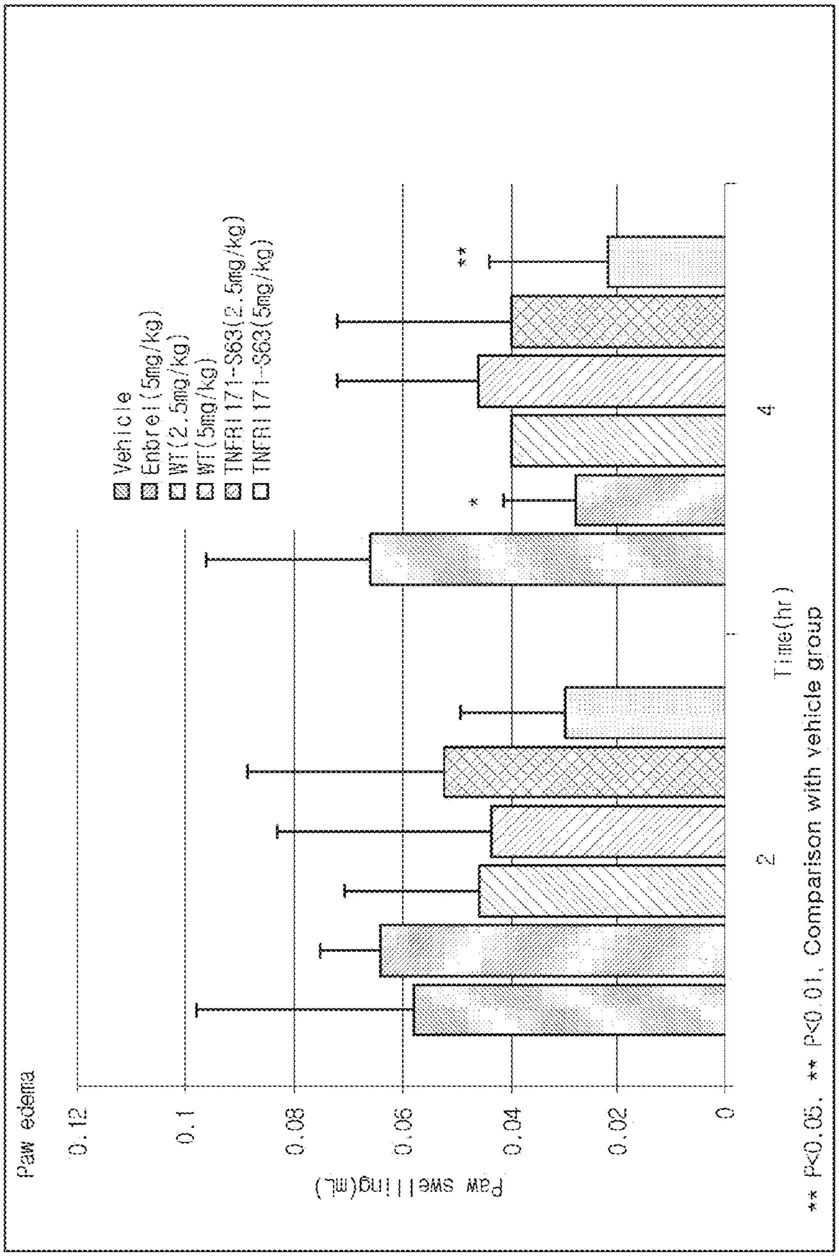
FIG. 11A is a graph showing the in vivo therapeutic effect of the TNFRI171 fragment and the TNFRI171 fragment mutants on carrageenan-induced paw edema in mice and FIG. 11B is a graph showing the levels of IL-6 in edema-induced foot tissues (vehicle, Enbrel, WT 2.5 mg/kg, WT 5 mg/kg, TNFRI-S63 2.5 mg/kg, TNFRI-S63 5 mg/ml from left).

Two hours after the intraplantar injection of carrageenan, as can be seen in FIG. 11A, the edemas of the group administered with TNFRI171-S63 at a dose of 5 mg/kg was observed to be significantly reduced in size, compared to the vehicle group. Four hours after the intraplantar injection of carrageenan, the edema in the Enbrel group and the TNFRI171-S63 group (5 mg/kg) had been significantly reduced, compared to the vehicle group. A greater reduction in edema was made in the TNFRI171-S63 group (5 mg/kg) than in the positive group administered with Enbrel at a dose of 5 mg/kg (FIG. 11A).

Figure 11B:
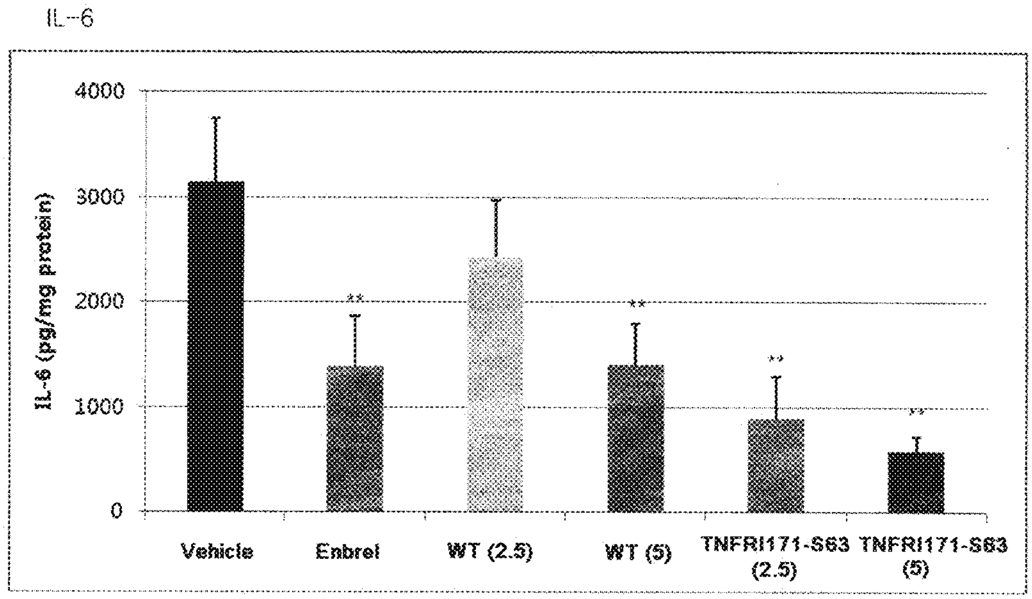

As can be seen FIG. 11B, the level of the inflammatory cytokine IL-6 was significantly reduced in all the test groups except for the WT group (2.5 mg/kg), compared to the vehicle group (P<0.01), four hours after the intraplantar injection of carrageenan (FIG. 11B). The inhibitory activity against IL-6 was noticeable in both the groups administered TNFRI171-S63 at a dose of 2.5 mg/kg and 5 mg/kg, compared to the Enbrel group (5 mg/kg). Given the same concentration, WT and Enbrel were found to reduce IL-6 to similar extent. Consequently, TNFRI171-S63 exhibited excellent inhibitory effects on edema and IL-6, compared to WT and Enbrel.

The invention claimed is:

1. A modified tumor necrosis factor receptor-1 polypeptide, comprising an amino acid sequence selected from the group consisting of:

an amino acid sequence comprising modifications of 5 amino acid residues consisting of 4 amino acid residues at positions 92, 95, 97 and 98, and 1 amino acid residue at one selected from among positions 68, 161, 200 and 207 in an amino acid sequence of a wild-type tumor necrosis factor receptor-1 polypeptide represented by SEQ ID NO: 1;

an amino acid sequence comprising modifications of 5 amino acid residues consisting of 4 amino acid residues at positions 92, 95, 97 and 98, and 1 amino acid residue at one selected from among positions 68, 161, 200 and 207 in an amino acid sequence (TNFRI171) consisting of amino acids 41-211 of an amino acid sequence of a wild-type tumor necrosis factor receptor-1 polypeptide represented by SEQ ID NO: 1;

an amino acid sequence comprising modifications of 5 amino acid residues consisting of 4 amino acid residues at positions 92, 95, 97 and 98, and 1 amino acid residue at one selected from among positions 68 and 161 in an amino acid sequence (TNFRI126) consisting of amino acids 41-166 of an amino acid sequence of a wild-type tumor necrosis factor receptor-1 polypeptide represented by SEQ ID NO: 1; and an amino acid sequence comprising modifications of 5 amino acid residues at positions 68, 92, 95, 97 and 98 in an amino acid sequence (TNFRI105) consisting of amino acids 41-145 of an amino acid sequence of a wild-type tumor necrosis factor receptor-1 polypeptide represented by SEQ ID NO: 1.

2. The modified tumor necrosis factor receptor-1 polypeptide of claim 1, comprising an amino acid sequence selected from the group consisting of:

an amino acid sequence comprising modifications of 5 amino acid residues at positions 68, 92, 95, 97 and 98 in an amino acid sequence of a wild-type tumor necrosis factor receptor-1 polypeptide represented by SEQ ID NO: 1;

an amino acid sequence comprising modifications of 5 amino acid residues at positions 68, 92, 95, 97 and 98 in an amino acid sequence (TNFRI171) consisting of amino acids 41-211 of an amino acid sequence of a wild-type tumor necrosis factor receptor-1 polypeptide represented by SEQ ID NO: 1;

an amino acid sequence comprising modifications of 5 amino acid residues at positions 68, 92, 95, 97 and 98 in an amino acid sequence (TNFRI126) consisting of amino acids 41-166 of an amino acid sequence of a wild-type tumor necrosis factor receptor-1 polypeptide represented by SEQ ID NO: 1.

3. The modified tumor necrosis factor receptor-1 polypeptide of claim 2, wherein the amino acid sequence based on the amino acid sequence of a wild-type tumor necrosis factor receptor-1 polypeptide represented by SEQ ID NO: 1 further comprises a modification of an amino acid residue at position 161 or 207;

the amino acid sequence based the amino acid sequence of TNFRI171 further comprises a modification of an amino acid residue at position 161 or 207; or the amino acid sequence based the amino acid sequence of TNFRI126 further comprises a modification of an amino acid residue at position 161.

4. The modified tumor necrosis factor receptor-1 polypeptide of claim 1, wherein amino acid residues are modified in such a way that:

L at position 68 is substituted with V;

S at position 92 is substituted with I, L, F, M, W, Q, T, Y, K, H, E, A, V, P, N or R;

H at position 95 is substituted with F;

R at position 97 is substituted with P, L or I;

H at position 98 is substituted with A or G;

K at position 161 is substituted with Q or N;

E at position 200 is substituted with Q; and

D at position 207 is substituted with N.

5. The modified tumor necrosis factor receptor-1 polypeptide of claim 4, wherein S at position 92 is substituted with I, M or H; and R at position 97 is substituted with P.

6. The modified tumor necrosis factor receptor-1 polypeptide of claim 1, wherein the amino acid sequence based on the amino acid sequence of a wild-type tumor necrosis factor receptor-1 polypeptide represented by SEQ ID NO: 1 further comprises a substitution of E with P at position 93;

the amino acid sequence based on the amino acid sequence of TNFRI171 further comprises a substitution of E with P at position 93;

the amino acid sequence based on the amino acid sequence of TNFRI126 further comprises a substitution of E with P at position 93; or the amino acid sequence based on the amino acid sequence of TNFRI105 further comprises a substitution of E with P at position 93.

7. The modified tumor necrosis factor receptor-1 polypeptide of claim 1, comprising an amino acid modification selected from the group consisting of L68V/S92I/H95F/R97P/H98A, L68V/S92M/H95F/R97P/H98A, L68V/S92H/H95F/R97P/H98A, L68V/S92I/H95F/R97P/H98G and L68V/S92M/H95F/R97P/H98G.

8. The modified tumor necrosis factor receptor-1 polypeptide of claim 3, comprising an amino acid modification selected from the group consisting of L68V/S92I/H95F/R97P/H98A/K161Q, L68V/S92I/H95F/R97P/H98A/K161N, L68V/S92I/H95F/R97P/H98A/D207N, L68V/S92M/H95F/R97P/H98A/K161Q, L68V/S92M/H95F/R97P/H98A/K161N, L68V/S92M/H95F/R97P/H98A/D207N, L68V/S92H/H95F/R97P/H98A/K161Q, L68V/S92H/H95F/R97P/H98A/K161N, L68V/S92H/H95F/R97P/H98A/D207N, L68V/S92I/H95F/R97P/H98G/K161Q, and L68V/S92M/H95F/R97P/H98G/K161N.

9. The modified tumor necrosis factor receptor-1 polypeptide of claim 6, comprising an amino acid modification of L68V/S92I/E93P/H95F/R97P/H98G.

10. The modified tumor necrosis factor receptor-1 polypeptide of claim 1, comprising an amino acid sequence selected from the group consisting of SEQ ID NOS: 6, 11, 16, 21, 22, 28-39, 44, 49, 54, 55, 61-72, 75, 78, 81, 82, and 86-98.

11. A polypeptide complex, comprising two or more copies of the modified tumor necrosis factor receptor-1 polypeptide of claim 1, said copies being covalently linked with each other.

12. The modified tumor necrosis factor receptor-1 polypeptide of claim 1, further comprising a chemical modification selected from the group consisting of glycosylation, acylation, methylation, phosphorylation, hasylation, carbamylation, sulfation, prenylation, oxidation, guanidination, amidination, carbamylation, trinitrophenylation, nitration, and PEGylation.

13. A cDNA comprising a nucleotide sequence encoding for the modified tumor necrosis factor receptor-1 polypeptide or fragment of claim 1.

14. The cDNA of claim 13, constructed on basis of the nucleotide sequence of SEQ ID NO: 5 with codon optimization, said codon optimization being performed to enable the cDNA to be expressed in *E. coli.*

15. A vector carrying the cDNA of claim 13.

16. A bacterial cell or non-human animal cell, transformed with the vector of claim 15.

17. The cell of claim 16, wherein the cell is *E. coli.*

18. A pharmaceutical formulation, comprising the modified tumor necrosis factor receptor-1 polypeptide of claim 1 and a pharmaceutically acceptable carrier.

19. A pharmaceutical composition for treating of a TNF-mediated disease selected from the group consisting of adult respiratory distress syndrome, anorexia, cancer, chronic fatigue syndrome, graft-versus-host rejection, hyperalgesia, inflammatory bowel disease, neuroinflammatory disease, ischemia including cerebral ischemia/reperfusion injury, trauma, epilepsy and hemorrhage, each causative of neurodegeneration, or brain injury resulting from spasm, diabetes, multiple sclerosis, eye diseases, pain, pancreatitis, pulmonary fibrosis, rheumatoid arthritis, osteoarthritis, juvenile (rheumatoid) arthritis, sero-negative polyarthritis, ankylosing spondylitis, Reiter's syndrome and reactive arthritis, psoriatic arthritis, enteropathic arthritis, polymyositis, dermatomyositis, dermato sclerosis, systemic sclerosis, vasculitis, cerebral vasculitis, Sjogren's syndrome, rheumatoid fever, polychondritis, polymyalgia rheumatica, rheumatoid and giant cell arteritis, septic shock, radiotherapy-induced side effects, systemic lupus erythematosus, temporomandibular joint disorder, thyroiditis, and tissue transplantation, comprising the modified tumor necrosis factor receptor-1 polypeptide of claim 1.

20. A pharmaceutical composition for treating of a TNF-mediated disease selected from the group consisting of adult respiratory distress syndrome, anorexia, cancer, chronic fatigue syndrome, graft-versus-host rejection, hyperalgesia, inflammatory bowel disease, neuroinflammatory disease, ischemia including cerebral ischemia/reperfusion injury, trauma, epilepsy and hemorrhage, each causative of neurodegeneration, or brain injury resulting from spasm, diabetes, multiple sclerosis, eye diseases, pain, pancreatitis, pulmonary fibrosis, rheumatoid arthritis, osteoarthritis, juvenile (rheumatoid) arthritis, sero-negative polyarthritis, ankylosing spondylitis, Reiter's syndrome and reactive arthritis, psoriatic arthritis, enteropathic arthritis, polymyositis, dermatomyositis, dermato sclerosis, systemic sclerosis, vasculitis, cerebral vasculitis, Sjogren's syndrome, rheumatoid fever, polychondritis, polymyalgia rheumatica, rheumatoid and giant cell arteritis, septic shock, radiotherapy-induced side effects, systemic lupus erythematosus, temporomandibular joint disorder, thyroiditis, and tissue transplantation, comprising the cDNA of claim 13 or a vector carrying the cDNA.

21. A method for treating a TNF-mediated disease, comprising administering the pharmaceutical composition of claim 19 to a subject in need thereof.

22. A method for treating a TNF-mediated disease, comprising administering the pharmaceutical composition of claim 20 to a subject in need thereof.

23. A method for producing the modified human tumor necrosis factor receptor-1 polypeptide of claim 1, comprising using the cDNA of claim 13 or a vector carrying the cDNA.

24. The modified tumor necrosis factor receptor-1 polypeptide of claim 3, comprising an amino acid modification of L68V/S92M/H95F/R97P/H98G/K161N.

* * * * *

SEQUENCE LISTING

```
<160> NUMBER OF SEQ ID NOS: 423

<210> SEQ ID NO 1
<211> LENGTH: 455
<212> TYPE: PRT
<213> ORGANISM: Homo sapiens
<220> FEATURE:
<223> OTHER INFORMATION: TNFRI wild type

<400> SEQUENCE: 1

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190
```

```
Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 2
<211> LENGTH: 171
<212> TYPE: PRT
<213> ORGANISM: Homo sapiens

<400> SEQUENCE: 2

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110
```

```
Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 3
<211> LENGTH: 126
<212> TYPE: PRT
<213> ORGANISM: Homo sapiens

<400> SEQUENCE: 3

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 4
<211> LENGTH: 105
<212> TYPE: PRT
<213> ORGANISM: Homo sapiens

<400> SEQUENCE: 4

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105


<210> SEQ ID NO 5
<211> LENGTH: 516
<212> TYPE: DNA
<213> ORGANISM: Artificial Sequence
<220> FEATURE:
<223> OTHER INFORMATION: Description of Artificial Sequence: Synthetic
```

TNFRI171 polynucleotide (for bacterial
expression)

<400> SEQUENCE: 5

```
gatagcgtgt gcccgcaggg taagtatatt catccgcaaa ataactctat ctgttgcaca     60

aagtgtcaca aagggacgta cctgtataat gactgtccgg ggccgggtca ggataccgac    120

tgccgcgagt gcgagagtgg gtcatttaca gcgagtgaga atcatctgcg ccactgcctg    180

agctgttcta agtgtcgtaa agagatgggc caagttgaaa tttcttcatg tacggtagac    240

cgcgatacgg tatgtggttg ccgtaaaaac cagtatcgcc attattggtc agaaaacctg    300

ttccagtgtt ttaattgctc cctgtgtctg aacggcactg tgcatctgtc ctgtcaggag    360

aagcagaata cagtttgtac ctgccatgca ggtttctttc taagagaaaa cgagtgtgtc    420

tcctgtagta actgtaagaa aagcctggag tgcacgaagt tgtgcctacc ccagattgag    480

aatgttaagg gcactgagga ctcaggcacc acataa                              516
```

<210> SEQ ID NO 6
<211> LENGTH: 455
<212> TYPE: PRT
<213> ORGANISM: Artificial Sequence
<220> FEATURE:
<223> OTHER INFORMATION: Description of Artificial Sequence: Synthetic
TNFRI-S31 L68V/S92I/H95F/R97P/H98A polypeptide

<400> SEQUENCE: 6

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Ile Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240
```

```
Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 7
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S32 S92I/H95F/R97P/H98A/K161Q polypeptide

<400> SEQUENCE: 7

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ile Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140
```

```
Asn Cys Ser Leu Cys Leu Asn Gly Thr Val His Leu Ser Cys Gln Glu
145                 150                 155                 160

Gln Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 8
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S33 S92I/H95F/R97P/H98A/K161N polypeptide

<400> SEQUENCE: 8

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45
```

```
Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ile Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Asn Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455
```

<210> SEQ ID NO 9

<211> LENGTH: 455
<212> TYPE: PRT
<213> ORGANISM: Artificial Sequence
<220> FEATURE:
<223> OTHER INFORMATION: Description of Artificial Sequence: Synthetic
TNFRI-S34 S92I/H95F/R97P/H98A/E200Q polypeptide

<400> SEQUENCE: 9

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ile Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Gln Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380
```

```
Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 10
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S35 S92I/H95F/R97P/H98A/D207N polypeptide

<400> SEQUENCE: 10

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ile Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asn Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285
```

```
Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 11
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S36 L68V/S92M/H95F/R97P/H98A polypeptide

<400> SEQUENCE: 11

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Met Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190
```

```
Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455
```

<210> SEQ ID NO 12
<211> LENGTH: 455
<212> TYPE: PRT
<213> ORGANISM: Artificial Sequence
<220> FEATURE:
<223> OTHER INFORMATION: Description of Artificial Sequence: Synthetic TNFRI-S37 S92M/H95F/R97P/H98A/K161Q polypeptide

<400> SEQUENCE: 12

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Met Glu Asn Phe Leu
                85                  90                  95
```

```
Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Gln Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455
```

<210> SEQ ID NO 13
<211> LENGTH: 455
<212> TYPE: PRT
<213> ORGANISM: Artificial Sequence
<220> FEATURE:
<223> OTHER INFORMATION: Description of Artificial Sequence: Synthetic
TNFRI-S38 S92M/H95F/R97P/H98A/K161N polypeptide

<400> SEQUENCE: 13

-continued

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Met Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Asn Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415
```

```
Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 14
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S39 S92M/H95F/R97P/H98A/E200Q polypeptide

<400> SEQUENCE: 14

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Met Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Gln Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320
```

```
Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 15
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S40 S92M/H95F/R97P/H98A/D207N polypeptide

<400> SEQUENCE: 15

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Met Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asn Ser
        195                 200                 205

Gly Thr Thr Val Leu Leu Pro Leu Val Ile Phe Phe Gly Leu Cys Leu
    210                 215                 220
```

```
Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455
```

<210> SEQ ID NO 16
<211> LENGTH: 455
<212> TYPE: PRT
<213> ORGANISM: Artificial Sequence
<220> FEATURE:
<223> OTHER INFORMATION: Description of Artificial Sequence: Synthetic TNFRI-S41 L68V/S92H/H95F/R97P/H98A polypeptide

<400> SEQUENCE: 16

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala His Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125
```

```
Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 17
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S42 S92H/H95F/R97P/H98A/K161Q polypeptide

<400> SEQUENCE: 17

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30
```

-continued

```
His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala His Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Gln Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455
```

<210> SEQ ID NO 18
<211> LENGTH: 455
<212> TYPE: PRT
<213> ORGANISM: Artificial Sequence
<220> FEATURE:
<223> OTHER INFORMATION: Description of Artificial Sequence: Synthetic
TNFRI-S43 S92H/H95F/R97P/H98A/K161N polypeptide

<400> SEQUENCE: 18

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala His Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Asn Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365
```

```
Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 19
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S44 S92H/H95F/R97P/H98A/E200Q polypeptide

<400> SEQUENCE: 19

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala His Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Gln Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270
```

```
Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 20
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S45 S92H/H95F/R97P/H98A/D207N polypeptide

<400> SEQUENCE: 20

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala His Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175
```

```
Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asn Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 21
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S46 L68V/S92I/H95F/R97P/H98G polypeptide

<400> SEQUENCE: 21

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80
```

```
Cys Arg Glu Cys Glu Ser Gly Ser Phe Thr Ala Ile Glu Asn Phe Leu
                85                  90                  95

Pro Gly Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455
```

<210> SEQ ID NO 22
<211> LENGTH: 455
<212> TYPE: PRT
<213> ORGANISM: Artificial Sequence
<220> FEATURE:
<223> OTHER INFORMATION: Description of Artificial Sequence: Synthetic -continued TNFRI-S47 L68V/S92M/H95F/R97P/H98G polypeptide

<400> SEQUENCE: 22

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Met Glu Asn Phe Leu
                85                  90                  95

Pro Gly Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400
```

```
Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 23
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S48 L68V/S92I/E93P/H95F/R97P/H98G polypeptide

<400> SEQUENCE: 23

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Ile Pro Asn Phe Leu
                85                  90                  95

Pro Gly Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300
```

Pro Asn Phe Ala Ala Pro Arg Arg Glu Val Ala Pro Pro Tyr Gln Gly
305 310 315 320

Ala Asp Pro Ile Leu Ala Thr Ala Leu Ala Ser Asp Pro Ile Pro Asn
325 330 335

Pro Leu Gln Lys Trp Glu Asp Ser Ala His Lys Pro Gln Ser Leu Asp
340 345 350

Thr Asp Asp Pro Ala Thr Leu Tyr Ala Val Val Glu Asn Val Pro Pro
355 360 365

Leu Arg Trp Lys Glu Phe Val Arg Arg Leu Gly Leu Ser Asp His Glu
370 375 380

Ile Asp Arg Leu Glu Leu Gln Asn Gly Arg Cys Leu Arg Glu Ala Gln
385 390 395 400

Tyr Ser Met Leu Ala Thr Trp Arg Arg Arg Thr Pro Arg Arg Glu Ala
405 410 415

Thr Leu Glu Leu Leu Gly Arg Val Leu Arg Asp Met Asp Leu Leu Gly
420 425 430

Cys Leu Glu Asp Ile Glu Glu Ala Leu Cys Gly Pro Ala Ala Leu Pro
435 440 445

Pro Ala Pro Ser Leu Leu Arg
450 455

<210> SEQ ID NO 24
<211> LENGTH: 455
<212> TYPE: PRT
<213> ORGANISM: Artificial Sequence
<220> FEATURE:
<223> OTHER INFORMATION: Description of Artificial Sequence: Synthetic
TNFRI-S49 S92I/E93P/H95F/R97P/H98G/K161Q polypeptide

<400> SEQUENCE: 24

Met Gly Leu Ser Thr Val Pro Asp Leu Leu Leu Pro Leu Val Leu Leu
1 5 10 15

Glu Leu Leu Val Gly Ile Tyr Pro Ser Gly Val Ile Gly Leu Val Pro
20 25 30

His Leu Gly Asp Arg Glu Lys Arg Asp Ser Val Cys Pro Gln Gly Gln
35 40 45

Tyr Ile His Pro Gln Asn Asn Ser Ile Cys Cys Thr Lys Cys His Lys
50 55 60

Gly Thr Tyr Leu Tyr Asn Asp Cys Pro Gly Pro Gly Gln Asp Thr Asp
65 70 75 80

Cys Arg Glu Cys Glu Ser Gly Ser Phe Thr Ala Ile Pro Asn Phe Leu
85 90 95

Pro Gly Cys Leu Ser Cys Ser Lys Cys Arg Lys Glu Met Gly Gln Val
100 105 110

Glu Ile Ser Ser Cys Thr Val Asp Arg Asp Thr Val Cys Gly Cys Arg
115 120 125

Lys Asn Gln Tyr Arg His Tyr Trp Ser Glu Asn Leu Phe Gln Cys Phe
130 135 140

Asn Cys Ser Leu Cys Leu Asn Gly Thr Val His Leu Ser Cys Gln Glu
145 150 155 160

Gln Gln Asn Thr Val Cys Thr Cys His Ala Gly Phe Phe Leu Arg Glu
165 170 175

Asn Glu Cys Val Ser Cys Ser Asn Cys Lys Lys Ser Leu Glu Cys Thr
180 185 190

Lys Leu Cys Leu Pro Gln Ile Glu Asn Val Lys Gly Thr Glu Asp Ser
195 200 205

```
Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455
```

<210> SEQ ID NO 25
<211> LENGTH: 455
<212> TYPE: PRT
<213> ORGANISM: Artificial Sequence
<220> FEATURE:
<223> OTHER INFORMATION: Description of Artificial Sequence: Synthetic
TNFRI-S50 S92I/E93P/H95F/R97P/H98G/K161N polypeptide

<400> SEQUENCE: 25

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ile Pro Asn Phe Leu
                85                  90                  95

Pro Gly Cys Leu Ser Cys Ser Lys Cys Arg Lys Glu Met Gly Gln Val
            100                 105                 110
```

-continued

```
Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Asn Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 26
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S51 S92I/E93P/H95F/R97P/H98G/E200Q polypeptide

<400> SEQUENCE: 26

Met Gly Leu Ser Thr Val Pro Asp Leu Leu Leu Pro Leu Val Leu Leu
1               5                   10                  15
```

-continued

```
Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ile Pro Asn Phe Leu
                85                  90                  95

Pro Gly Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Gln Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445
```

Pro Ala Pro Ser Leu Leu Arg
450 455

<210> SEQ ID NO 27
<211> LENGTH: 455
<212> TYPE: PRT
<213> ORGANISM: Artificial Sequence
<220> FEATURE:
<223> OTHER INFORMATION: Description of Artificial Sequence: Synthetic
TNFRI-S52 S92I/E93P/H95F/R97P/H98G/D207N polypeptide

<400> SEQUENCE: 27

Met Gly Leu Ser Thr Val Pro Asp Leu Leu Leu Pro Leu Val Leu Leu
1 5 10 15

Glu Leu Leu Val Gly Ile Tyr Pro Ser Gly Val Ile Gly Leu Val Pro
20 25 30

His Leu Gly Asp Arg Glu Lys Arg Asp Ser Val Cys Pro Gln Gly Gln
35 40 45

Tyr Ile His Pro Gln Asn Asn Ser Ile Cys Cys Thr Lys Cys His Lys
50 55 60

Gly Thr Tyr Leu Tyr Asn Asp Cys Pro Gly Pro Gly Gln Asp Thr Asp
65 70 75 80

Cys Arg Glu Cys Glu Ser Gly Ser Phe Thr Ala Ile Pro Asn Phe Leu
85 90 95

Pro Gly Cys Leu Ser Cys Ser Lys Cys Arg Lys Glu Met Gly Gln Val
100 105 110

Glu Ile Ser Ser Cys Thr Val Asp Arg Asp Thr Val Cys Gly Cys Arg
115 120 125

Lys Asn Gln Tyr Arg His Tyr Trp Ser Glu Asn Leu Phe Gln Cys Phe
130 135 140

Asn Cys Ser Leu Cys Leu Asn Gly Thr Val His Leu Ser Cys Gln Glu
145 150 155 160

Lys Gln Asn Thr Val Cys Thr Cys His Ala Gly Phe Phe Leu Arg Glu
165 170 175

Asn Glu Cys Val Ser Cys Ser Asn Cys Lys Lys Ser Leu Glu Cys Thr
180 185 190

Lys Leu Cys Leu Pro Gln Ile Glu Asn Val Lys Gly Thr Glu Asn Ser
195 200 205

Gly Thr Thr Val Leu Leu Pro Leu Val Ile Phe Phe Gly Leu Cys Leu
210 215 220

Leu Ser Leu Leu Phe Ile Gly Leu Met Tyr Arg Tyr Gln Arg Trp Lys
225 230 235 240

Ser Lys Leu Tyr Ser Ile Val Cys Gly Lys Ser Thr Pro Glu Lys Glu
245 250 255

Gly Glu Leu Glu Gly Thr Thr Thr Lys Pro Leu Ala Pro Asn Pro Ser
260 265 270

Phe Ser Pro Thr Pro Gly Phe Thr Pro Thr Leu Gly Phe Ser Pro Val
275 280 285

Pro Ser Ser Thr Phe Thr Ser Ser Ser Thr Tyr Thr Pro Gly Asp Cys
290 295 300

Pro Asn Phe Ala Ala Pro Arg Arg Glu Val Ala Pro Pro Tyr Gln Gly
305 310 315 320

Ala Asp Pro Ile Leu Ala Thr Ala Leu Ala Ser Asp Pro Ile Pro Asn
325 330 335

Pro Leu Gln Lys Trp Glu Asp Ser Ala His Lys Pro Gln Ser Leu Asp
340 345 350

Thr Asp Asp Pro Ala Thr Leu Tyr Ala Val Val Glu Asn Val Pro Pro
355 360 365

Leu Arg Trp Lys Glu Phe Val Arg Arg Leu Gly Leu Ser Asp His Glu
370 375 380

Ile Asp Arg Leu Glu Leu Gln Asn Gly Arg Cys Leu Arg Glu Ala Gln
385 390 395 400

Tyr Ser Met Leu Ala Thr Trp Arg Arg Arg Thr Pro Arg Arg Glu Ala
405 410 415

Thr Leu Glu Leu Leu Gly Arg Val Leu Arg Asp Met Asp Leu Leu Gly
420 425 430

Cys Leu Glu Asp Ile Glu Glu Ala Leu Cys Gly Pro Ala Ala Leu Pro
435 440 445

Pro Ala Pro Ser Leu Leu Arg
450 455

<210> SEQ ID NO 28
<211> LENGTH: 455
<212> TYPE: PRT
<213> ORGANISM: Artificial Sequence
<220> FEATURE:
<223> OTHER INFORMATION: Description of Artificial Sequence: Synthetic
TNFRI-S53 L68V/S92I/H95F/R97P/H98A/K161Q polypeptide

<400> SEQUENCE: 28

Met Gly Leu Ser Thr Val Pro Asp Leu Leu Leu Pro Leu Val Leu Leu
1 5 10 15

Glu Leu Leu Val Gly Ile Tyr Pro Ser Gly Val Ile Gly Leu Val Pro
20 25 30

His Leu Gly Asp Arg Glu Lys Arg Asp Ser Val Cys Pro Gln Gly Gln
35 40 45

Tyr Ile His Pro Gln Asn Asn Ser Ile Cys Cys Thr Lys Cys His Lys
50 55 60

Gly Thr Tyr Val Tyr Asn Asp Cys Pro Gly Pro Gly Gln Asp Thr Asp
65 70 75 80

Cys Arg Glu Cys Glu Ser Gly Ser Phe Thr Ala Ile Glu Asn Phe Leu
85 90 95

Pro Ala Cys Leu Ser Cys Ser Lys Cys Arg Lys Glu Met Gly Gln Val
100 105 110

Glu Ile Ser Ser Cys Thr Val Asp Arg Asp Thr Val Cys Gly Cys Arg
115 120 125

Lys Asn Gln Tyr Arg His Tyr Trp Ser Glu Asn Leu Phe Gln Cys Phe
130 135 140

Asn Cys Ser Leu Cys Leu Asn Gly Thr Val His Leu Ser Cys Gln Glu
145 150 155 160

Gln Gln Asn Thr Val Cys Thr Cys His Ala Gly Phe Phe Leu Arg Glu
165 170 175

Asn Glu Cys Val Ser Cys Ser Asn Cys Lys Lys Ser Leu Glu Cys Thr
180 185 190

Lys Leu Cys Leu Pro Gln Ile Glu Asn Val Lys Gly Thr Glu Asp Ser
195 200 205

Gly Thr Thr Val Leu Leu Pro Leu Val Ile Phe Phe Gly Leu Cys Leu
210 215 220

Leu Ser Leu Leu Phe Ile Gly Leu Met Tyr Arg Tyr Gln Arg Trp Lys
225 230 235 240

Ser Lys Leu Tyr Ser Ile Val Cys Gly Lys Ser Thr Pro Glu Lys Glu
245 250 255

```
Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455
```

<210> SEQ ID NO 29
<211> LENGTH: 455
<212> TYPE: PRT
<213> ORGANISM: Artificial Sequence
<220> FEATURE:
<223> OTHER INFORMATION: Description of Artificial Sequence: Synthetic TNFRI-S54 L68V/S92I/H95F/R97P/H98A/K161N polypeptide

<400> SEQUENCE: 29

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Ile Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160
```

```
Asn Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 30
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S55 L68V/S92I/H95F/R97P/H98A/D207N polypeptide

<400> SEQUENCE: 30

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60
```

```
Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Ile Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asn Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455
```

<210> SEQ ID NO 31
<211> LENGTH: 455
<212> TYPE: PRT

```
<213> ORGANISM: Artificial Sequence
<220> FEATURE:
<223> OTHER INFORMATION: Description of Artificial Sequence: Synthetic
      TNFRI-S56 L68V/S92M/H95F/R97P/H98A/K161Q polypeptide

<400> SEQUENCE: 31

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Met Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Gln Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380
```

-continued

```
Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 32
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S57 L68V/S92M/H95F/R97P/H98A/K161N polypeptide

<400> SEQUENCE: 32

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Met Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Asn Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285
```

```
Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 33
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S58 L68V/S92M/H95F/R97P/H98A/D207N polypeptide

<400> SEQUENCE: 33

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Met Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190
```

```
Lys Leu Cys Leu Pro Gln Ile Glu Asn Val Lys Gly Thr Glu Asn Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 34
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S59 L68V/S92H/H95F/R97P/H98A/K161Q polypeptide

<400> SEQUENCE: 34

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala His Glu Asn Phe Leu
                85                  90                  95
```

```
Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Gln Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455
```

<210> SEQ ID NO 35
<211> LENGTH: 455
<212> TYPE: PRT
<213> ORGANISM: Artificial Sequence
<220> FEATURE:
<223> OTHER INFORMATION: Description of Artificial Sequence: Synthetic TNFRI-S60 L68V/S92H/H95F/R97P/H98A/K161N polypeptide

<400> SEQUENCE: 35

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala His Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Asn Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430
```

```
Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 36
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S61 L68V/S92H/H95F/R97P/H98A/D207N polypeptide

<400> SEQUENCE: 36

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala His Glu Asn Phe Leu
                85                  90                  95

Pro Ala Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asn Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335
```

```
Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 37
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S62 L68V/S92I/H95F/R97P/H98G/K161Q polypeptide

<400> SEQUENCE: 37

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Ile Glu Asn Phe Leu
                85                  90                  95

Pro Gly Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240
```

```
Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 38
<211> LENGTH: 455
<212> TYPE: PRT
<213> ORGANISM: Artificial Sequence
<220> FEATURE:
<223> OTHER INFORMATION: Description of Artificial Sequence: Synthetic
      TNFRI-S63 L68V/S92M/H95F/R97P/H98G/K161N polypeptide

<400> SEQUENCE: 38

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Gln
        35                  40                  45

Tyr Ile His Pro Gln Asn Asn Ser Ile Cys Cys Thr Lys Cys His Lys
    50                  55                  60

Gly Thr Tyr Val Tyr Asn Asp Cys Pro Gly Pro Gly Gln Asp Thr Asp
65                  70                  75                  80

Cys Arg Glu Cys Glu Ser Gly Ser Phe Thr Ala Met Glu Asn Phe Leu
                85                  90                  95

Pro Gly Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140
```

Asn Cys Ser Leu Cys Leu Asn Gly Thr Val His Leu Ser Cys Gln Glu
145 150 155 160

Asn Gln Asn Thr Val Cys Thr Cys His Ala Gly Phe Phe Leu Arg Glu
165 170 175

Asn Glu Cys Val Ser Cys Ser Asn Cys Lys Lys Ser Leu Glu Cys Thr
180 185 190

Lys Leu Cys Leu Pro Gln Ile Glu Asn Val Lys Gly Thr Glu Asp Ser
195 200 205

Gly Thr Thr Val Leu Leu Pro Leu Val Ile Phe Phe Gly Leu Cys Leu
210 215 220

Leu Ser Leu Leu Phe Ile Gly Leu Met Tyr Arg Tyr Gln Arg Trp Lys
225 230 235 240

Ser Lys Leu Tyr Ser Ile Val Cys Gly Lys Ser Thr Pro Glu Lys Glu
245 250 255

Gly Glu Leu Glu Gly Thr Thr Thr Lys Pro Leu Ala Pro Asn Pro Ser
260 265 270

Phe Ser Pro Thr Pro Gly Phe Thr Pro Thr Leu Gly Phe Ser Pro Val
275 280 285

Pro Ser Ser Thr Phe Thr Ser Ser Ser Thr Tyr Thr Pro Gly Asp Cys
290 295 300

Pro Asn Phe Ala Ala Pro Arg Arg Glu Val Ala Pro Pro Tyr Gln Gly
305 310 315 320

Ala Asp Pro Ile Leu Ala Thr Ala Leu Ala Ser Asp Pro Ile Pro Asn
325 330 335

Pro Leu Gln Lys Trp Glu Asp Ser Ala His Lys Pro Gln Ser Leu Asp
340 345 350

Thr Asp Asp Pro Ala Thr Leu Tyr Ala Val Val Glu Asn Val Pro Pro
355 360 365

Leu Arg Trp Lys Glu Phe Val Arg Arg Leu Gly Leu Ser Asp His Glu
370 375 380

Ile Asp Arg Leu Glu Leu Gln Asn Gly Arg Cys Leu Arg Glu Ala Gln
385 390 395 400

Tyr Ser Met Leu Ala Thr Trp Arg Arg Arg Thr Pro Arg Arg Glu Ala
405 410 415

Thr Leu Glu Leu Leu Gly Arg Val Leu Arg Asp Met Asp Leu Leu Gly
420 425 430

Cys Leu Glu Asp Ile Glu Glu Ala Leu Cys Gly Pro Ala Ala Leu Pro
435 440 445

Pro Ala Pro Ser Leu Leu Arg
450 455

<210> SEQ ID NO 39
<211> LENGTH: 171
<212> TYPE: PRT
<213> ORGANISM: Artificial Sequence
<220> FEATURE:
<223> OTHER INFORMATION: Description of Artificial Sequence: Synthetic
TNFRI171-S31 L68V/S92I/H95F/R97P/H98A polypeptide

<400> SEQUENCE: 39

Asp Ser Val Cys Pro Gln Gly Gln Tyr Ile His Pro Gln Asn Asn Ser
1 5 10 15

Ile Cys Cys Thr Lys Cys His Lys Gly Thr Tyr Val Tyr Asn Asp Cys
20 25 30

Pro Gly Pro Gly Gln Asp Thr Asp Cys Arg Glu Cys Glu Ser Gly Ser
35 40 45

```
Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 40
<211> LENGTH: 171
<212> TYPE: PRT
<213> ORGANISM: Artificial Sequence
<220> FEATURE:
<223> OTHER INFORMATION: Description of Artificial Sequence: Synthetic TNFRI 171-S32 S92I/H95F/R97P/H98A/K161Q polypeptide

<400> SEQUENCE: 40

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Gln Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 41
<211> LENGTH: 171
<212> TYPE: PRT
<213> ORGANISM: Artificial Sequence
<220> FEATURE:
<223> OTHER INFORMATION: Description of Artificial Sequence: Synthetic TNFRI 171-S33 S92I/H95F/R97P/H98A/K161N polypeptide

<400> SEQUENCE: 41

-continued

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Asn Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 42
<211> LENGTH: 171
<212> TYPE: PRT
<213> ORGANISM: Artificial Sequence
<220> FEATURE:
<223> OTHER INFORMATION: Description of Artificial Sequence: Synthetic
      TNFRI 171-S34 S92I/H95F/R97P/H98A/E200Q polypeptide

<400> SEQUENCE: 42

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Gln
145                 150                 155                 160

Asn Val Lys Gly Thr Glu Asp Ser Gly Thr Thr
                165                 170


<210> SEQ ID NO 43
<211> LENGTH: 171
```

<212> TYPE: PRT
<213> ORGANISM: Artificial Sequence
<220> FEATURE:
<223> OTHER INFORMATION: Description of Artificial Sequence: Synthetic
TNFRI 171-S35 S92I/H95F/R97P/H98A/D207N polypeptide

<400> SEQUENCE: 43

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asn Ser Gly Thr Thr
                165                 170
```

<210> SEQ ID NO 44
<211> LENGTH: 171
<212> TYPE: PRT
<213> ORGANISM: Artificial Sequence
<220> FEATURE:
<223> OTHER INFORMATION: Description of Artificial Sequence: Synthetic
TNFRI 171-S36 L68V/S92M/H95F/R97P/H98A polypeptide

<400> SEQUENCE: 44

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140
```

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 45
<211> LENGTH: 171
<212> TYPE: PRT
<213> ORGANISM: Artificial Sequence
<220> FEATURE:
<223> OTHER INFORMATION: Description of Artificial Sequence: Synthetic TNFRI 171-S37 S92M/H95F/R97P/H98A/K161Q polypeptide

<400> SEQUENCE: 45

Asp Ser Val Cys Pro Gln Gly Gln Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Met Glu Asn Phe Leu Pro Ala Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Gln Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 46
<211> LENGTH: 171
<212> TYPE: PRT
<213> ORGANISM: Artificial Sequence
<220> FEATURE:
<223> OTHER INFORMATION: Description of Artificial Sequence: Synthetic TNFRI 171-S38 S92M/H95F/R97P/H98A/K161N polypeptide

<400> SEQUENCE: 46

Asp Ser Val Cys Pro Gln Gly Gln Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Met Glu Asn Phe Leu Pro Ala Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

-continued

```
Ser Glu Asn Leu Phe Gln Cys Phe Asn Cys Ser Leu Cys Leu Asn Gly
            100                 105                 110

Thr Val His Leu Ser Cys Gln Glu Asn Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 47
<211> LENGTH: 171
<212> TYPE: PRT
<213> ORGANISM: Artificial Sequence
<220> FEATURE:
<223> OTHER INFORMATION: Description of Artificial Sequence: Synthetic
      TNFRI 171-S39 S92M/H95F/R97P/H98A/E200Q polypeptide

<400> SEQUENCE: 47

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Gln
145                 150                 155                 160

Asn Val Lys Gly Thr Glu Asp Ser Gly Thr Thr
        165                 170


<210> SEQ ID NO 48
<211> LENGTH: 171
<212> TYPE: PRT
<213> ORGANISM: Artificial Sequence
<220> FEATURE:
<223> OTHER INFORMATION: Description of Artificial Sequence: Synthetic
      TNFRI 171-S40 S92M/H95F/R97P/H98A/D207N polypeptide

<400> SEQUENCE: 48

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45
```

```
Phe Thr Ala Met Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asn Ser Gly Thr Thr
                165                 170


<210> SEQ ID NO 49
<211> LENGTH: 171
<212> TYPE: PRT
<213> ORGANISM: Artificial Sequence
<220> FEATURE:
<223> OTHER INFORMATION: Description of Artificial Sequence: Synthetic
      TNFRI 171-S41 L68V/S92H/H95F/R97P/H98A polypeptide

<400> SEQUENCE: 49

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala His Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 50
<211> LENGTH: 171
<212> TYPE: PRT
<213> ORGANISM: Artificial Sequence
<220> FEATURE:
<223> OTHER INFORMATION: Description of Artificial Sequence: Synthetic
      TNFRI 171-S42 S92H/H95F/R97P/H98A/K161Q polypeptide

<400> SEQUENCE: 50
```

Asp Ser Val Cys Pro Gln Gly Gln Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala His Glu Asn Phe Leu Pro Ala Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Gln Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 51
<211> LENGTH: 171
<212> TYPE: PRT
<213> ORGANISM: Artificial Sequence
<220> FEATURE:
<223> OTHER INFORMATION: Description of Artificial Sequence: Synthetic
TNFRI 171-S43 S92H/H95F/R97P/H98A/K161N polypeptide

<400> SEQUENCE: 51

Asp Ser Val Cys Pro Gln Gly Gln Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala His Glu Asn Phe Leu Pro Ala Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Asn Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 52
<211> LENGTH: 171

<212> TYPE: PRT
<213> ORGANISM: Artificial Sequence
<220> FEATURE:
<223> OTHER INFORMATION: Description of Artificial Sequence: Synthetic
TNFRI 171-S44 S92H/H95F/R97P/H98A/E200Q polypeptide

<400> SEQUENCE: 52

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala His Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Gln
145                 150                 155                 160

Asn Val Lys Gly Thr Glu Asp Ser Gly Thr Thr
                165                 170
```

<210> SEQ ID NO 53
<211> LENGTH: 171
<212> TYPE: PRT
<213> ORGANISM: Artificial Sequence
<220> FEATURE:
<223> OTHER INFORMATION: Description of Artificial Sequence: Synthetic
TNFRI 171-S45 S92H/H95F/R97P/H98A/D207N polypeptide

<400> SEQUENCE: 53

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala His Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140
```

Cys Lys Lys Ser Leu Glu Cys Thr Lys Leu Cys Leu Pro Gln Ile Glu
145 150 155 160

Asn Val Lys Gly Thr Glu Asn Ser Gly Thr Thr
165 170

<210> SEQ ID NO 54
<211> LENGTH: 171
<212> TYPE: PRT
<213> ORGANISM: Artificial Sequence
<220> FEATURE:
<223> OTHER INFORMATION: Description of Artificial Sequence: Synthetic TNFRI 171-S46 L68V/S92I/H95F/R97P/H98G polypeptide

<400> SEQUENCE: 54

Asp Ser Val Cys Pro Gln Gly Gln Tyr Ile His Pro Gln Asn Asn Ser
1 5 10 15

Ile Cys Cys Thr Lys Cys His Lys Gly Thr Tyr Val Tyr Asn Asp Cys
20 25 30

Pro Gly Pro Gly Gln Asp Thr Asp Cys Arg Glu Cys Glu Ser Gly Ser
35 40 45

Phe Thr Ala Ile Glu Asn Phe Leu Pro Gly Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 55
<211> LENGTH: 171
<212> TYPE: PRT
<213> ORGANISM: Artificial Sequence
<220> FEATURE:
<223> OTHER INFORMATION: Description of Artificial Sequence: Synthetic TNFRI 171-S47 L68V/S92M/H95F/R97P/H98G polypeptide

<400> SEQUENCE: 55

Asp Ser Val Cys Pro Gln Gly Gln Tyr Ile His Pro Gln Asn Asn Ser
1 5 10 15

Ile Cys Cys Thr Lys Cys His Lys Gly Thr Tyr Val Tyr Asn Asp Cys
20 25 30

Pro Gly Pro Gly Gln Asp Thr Asp Cys Arg Glu Cys Glu Ser Gly Ser
35 40 45

Phe Thr Ala Met Glu Asn Phe Leu Pro Gly Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

```
Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 56
<211> LENGTH: 171
<212> TYPE: PRT
<213> ORGANISM: Artificial Sequence
<220> FEATURE:
<223> OTHER INFORMATION: Description of Artificial Sequence: Synthetic
      TNFRI 171-S48 L68V/S92I/E93P/H95F/R97P/H98G polypeptide

<400> SEQUENCE: 56

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Pro Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 57
<211> LENGTH: 171
<212> TYPE: PRT
<213> ORGANISM: Artificial Sequence
<220> FEATURE:
<223> OTHER INFORMATION: Description of Artificial Sequence: Synthetic
      TNFRI 171-S49 S92I/E93P/H95F/R97P/H98G/K161Q polypeptide

<400> SEQUENCE: 57

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45
```

```
Phe Thr Ala Ile Pro Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Gln Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 58
<211> LENGTH: 171
<212> TYPE: PRT
<213> ORGANISM: Artificial Sequence
<220> FEATURE:
<223> OTHER INFORMATION: Description of Artificial Sequence: Synthetic TNFRI 171-S50 S92I/E93P/H95F/R97P/H98G/K161N polypeptide

<400> SEQUENCE: 58

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Pro Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Asn Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 59
<211> LENGTH: 171
<212> TYPE: PRT
<213> ORGANISM: Artificial Sequence
<220> FEATURE:
<223> OTHER INFORMATION: Description of Artificial Sequence: Synthetic TNFRI 171-S51 S92I/E93P/H95F/R97P/H98G/E200Q polypeptide

<400> SEQUENCE: 59

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Pro Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Gln
145                 150                 155                 160

Asn Val Lys Gly Thr Glu Asp Ser Gly Thr Thr
                165                 170


<210> SEQ ID NO 60
<211> LENGTH: 171
<212> TYPE: PRT
<213> ORGANISM: Artificial Sequence
<220> FEATURE:
<223> OTHER INFORMATION: Description of Artificial Sequence: Synthetic
      TNFRI 171-S52 S92I/E93P/H95F/R97P/H98G/D207N polypeptide

<400> SEQUENCE: 60

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Pro Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asn Ser Gly Thr Thr
                165                 170


<210> SEQ ID NO 61
<211> LENGTH: 171
```

<212> TYPE: PRT
<213> ORGANISM: Artificial Sequence
<220> FEATURE:
<223> OTHER INFORMATION: Description of Artificial Sequence: Synthetic
TNFRI 171-S53 L68V/S92I/H95F/R97P/H98A/K161Q polypeptide

<400> SEQUENCE: 61

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Gln Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 62
<211> LENGTH: 171
<212> TYPE: PRT
<213> ORGANISM: Artificial Sequence
<220> FEATURE:
<223> OTHER INFORMATION: Description of Artificial Sequence: Synthetic
TNFRI 171-S54 L68V/S92I/H95F/R97P/H98A/K161N polypeptide

<400> SEQUENCE: 62

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Asn Gln Asn Thr Val Cys Thr Cys
        115                 120                 125

His Ala Gly Phe Phe Leu Arg Glu Asn Glu Cys Val Ser Cys Ser Asn
    130                 135                 140
```

```
Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 63
<211> LENGTH: 171
<212> TYPE: PRT
<213> ORGANISM: Artificial Sequence
<220> FEATURE:
<223> OTHER INFORMATION: Description of Artificial Sequence: Synthetic
      TNFRI 171-S55 L68V/S92I/H95F/R97P/H98A/D207N polypeptide

<400> SEQUENCE: 63

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asn Ser Gly Thr Thr
                165                 170


<210> SEQ ID NO 64
<211> LENGTH: 171
<212> TYPE: PRT
<213> ORGANISM: Artificial Sequence
<220> FEATURE:
<223> OTHER INFORMATION: Description of Artificial Sequence: Synthetic
      TNFRI 171-S56 L68V/S92M/H95F/R97P/H98A/K161Q polypeptide

<400> SEQUENCE: 64

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95
```

```
Ser Glu Asn Leu Phe Gln Cys Phe Asn Cys Ser Leu Cys Leu Asn Gly
            100                 105                 110

Thr Val His Leu Ser Cys Gln Glu Gln Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 65
<211> LENGTH: 170
<212> TYPE: PRT
<213> ORGANISM: Artificial Sequence
<220> FEATURE:
<223> OTHER INFORMATION: Description of Artificial Sequence: Synthetic
      TNFRI 171-S57 L68V/S92M/H95F/R97P/H98A/K161N polypeptide

<400> SEQUENCE: 65

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Asn Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr
                165                 170


<210> SEQ ID NO 66
<211> LENGTH: 171
<212> TYPE: PRT
<213> ORGANISM: Artificial Sequence
<220> FEATURE:
<223> OTHER INFORMATION: Description of Artificial Sequence: Synthetic
      TNFRI 171-S58 L68V/S92M/H95F/R97P/H98A/D207N polypeptide

<400> SEQUENCE: 66

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45
```

```
Phe Thr Ala Met Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asn Ser Gly Thr Thr
                165                 170


<210> SEQ ID NO 67
<211> LENGTH: 171
<212> TYPE: PRT
<213> ORGANISM: Artificial Sequence
<220> FEATURE:
<223> OTHER INFORMATION: Description of Artificial Sequence: Synthetic
      TNFRI 171-S59 L68V/S92H/H95F/R97P/H98A/K161Q polypeptide

<400> SEQUENCE: 67

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala His Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Gln Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 68
<211> LENGTH: 171
<212> TYPE: PRT
<213> ORGANISM: Artificial Sequence
<220> FEATURE:
<223> OTHER INFORMATION: Description of Artificial Sequence: Synthetic
      TNFRI 171-S60 L68V/S92H/H95F/R97P/H98A/K161N polypeptide

<400> SEQUENCE: 68
```

Asp Ser Val Cys Pro Gln Gly Gln Tyr Ile His Pro Gln Asn Asn Ser
1 5 10 15

Ile Cys Cys Thr Lys Cys His Lys Gly Thr Tyr Val Tyr Asn Asp Cys
20 25 30

Pro Gly Pro Gly Gln Asp Thr Asp Cys Arg Glu Cys Glu Ser Gly Ser
35 40 45

Phe Thr Ala His Glu Asn Phe Leu Pro Ala Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Asn Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asp Ser Gly Thr Thr
165 170

<210> SEQ ID NO 69
<211> LENGTH: 171
<212> TYPE: PRT
<213> ORGANISM: Artificial Sequence
<220> FEATURE:
<223> OTHER INFORMATION: Description of Artificial Sequence: Synthetic
TNFRI 171-S61 L68V/S92H/H95F/R97P/H98A/D207N polypeptide

<400> SEQUENCE: 69

Asp Ser Val Cys Pro Gln Gly Gln Tyr Ile His Pro Gln Asn Asn Ser
1 5 10 15

Ile Cys Cys Thr Lys Cys His Lys Gly Thr Tyr Val Tyr Asn Asp Cys
20 25 30

Pro Gly Pro Gly Gln Asp Thr Asp Cys Arg Glu Cys Glu Ser Gly Ser
35 40 45

Phe Thr Ala His Glu Asn Phe Leu Pro Ala Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn Val Lys Gly Thr Glu Asn Ser Gly Thr Thr
165 170

<210> SEQ ID NO 70
<211> LENGTH: 171

<212> TYPE: PRT
<213> ORGANISM: Artificial Sequence
<220> FEATURE:
<223> OTHER INFORMATION: Description of Artificial Sequence: Synthetic
TNFRI 171-S62 L68V/S92I/H95F/R97P/H98G/K161Q polypeptide

<400> SEQUENCE: 70

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 71
<211> LENGTH: 171
<212> TYPE: PRT
<213> ORGANISM: Artificial Sequence
<220> FEATURE:
<223> OTHER INFORMATION: Description of Artificial Sequence: Synthetic
TNFRI 171-S63 L68V/S92M/H95F/R97P/H98G/K161N polypeptide

<400> SEQUENCE: 71

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Asn Gln Asn Thr Val Cys Thr Cys
        115                 120                 125

His Ala Gly Phe Phe Leu Arg Glu Asn Glu Cys Val Ser Cys Ser Asn
    130                 135                 140
```

```
Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170


<210> SEQ ID NO 72
<211> LENGTH: 126
<212> TYPE: PRT
<213> ORGANISM: Artificial Sequence
<220> FEATURE:
<223> OTHER INFORMATION: Description of Artificial Sequence: Synthetic
      TNFRI126-S31 L68V/S92I/H95F/R97P/H98A polypeptide

<400> SEQUENCE: 72

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 73
<211> LENGTH: 126
<212> TYPE: PRT
<213> ORGANISM: Artificial Sequence
<220> FEATURE:
<223> OTHER INFORMATION: Description of Artificial Sequence: Synthetic
              TNFRI 126-S32 S92I/H95F/R97P/H98A/K161Q polypeptide

<400> SEQUENCE: 73

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Gln Gln Asn Thr Val Cys
        115                 120                 125


<210> SEQ ID NO 74
<211> LENGTH: 126
<212> TYPE: PRT
```

```
<213> ORGANISM: Artificial Sequence
<220> FEATURE:
<223> OTHER INFORMATION: Description of Artificial Sequence: Synthetic
      TNFRI 126-S33 S92I/H95F/R97P/H98A/K161N polypeptide

<400> SEQUENCE: 74

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Asn Gln Asn Thr Val Cys
        115                 120                 125


<210> SEQ ID NO 75
<211> LENGTH: 126
<212> TYPE: PRT
<213> ORGANISM: Artificial Sequence
<220> FEATURE:
<223> OTHER INFORMATION: Description of Artificial Sequence: Synthetic
      TNFRI 126-S36 L68V/S92M/H95F/R97P/H98A polypeptide

<400> SEQUENCE: 75

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 76
<211> LENGTH: 126
<212> TYPE: PRT
<213> ORGANISM: Artificial Sequence
<220> FEATURE:
<223> OTHER INFORMATION: Description of Artificial Sequence: Synthetic
      TNFRI 126-S37 S92M/H95F/R97P/H98A/K161Q polypeptide

<400> SEQUENCE: 76

Asp Ser Val Cys Pro Gln Gly Gln Tyr Ile His Pro Gln Asn Asn Ser
1               5                   10                  15
```

```
Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Gln Gln Asn Thr Val Cys
        115                 120                 125


<210> SEQ ID NO 77
<211> LENGTH: 126
<212> TYPE: PRT
<213> ORGANISM: Artificial Sequence
<220> FEATURE:
<223> OTHER INFORMATION: Description of Artificial Sequence: Synthetic
      TNFRI 126-S38 S92M/H95F/R97P/H98A/K161N polypeptide

<400> SEQUENCE: 77

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Asn Gln Asn Thr Val Cys
        115                 120                 125


<210> SEQ ID NO 78
<211> LENGTH: 126
<212> TYPE: PRT
<213> ORGANISM: Artificial Sequence
<220> FEATURE:
<223> OTHER INFORMATION: Description of Artificial Sequence: Synthetic
      TNFRI 126-S41 L68V/S92H/H95F/R97P/H98A polypeptide

<400> SEQUENCE: 78

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala His Glu Asn Phe Leu Pro Ala Cys Leu Ser Cys Ser Lys
    50                  55                  60
```

-continued

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys
115 120 125

<210> SEQ ID NO 79
<211> LENGTH: 126
<212> TYPE: PRT
<213> ORGANISM: Artificial Sequence
<220> FEATURE:
<223> OTHER INFORMATION: Description of Artificial Sequence: Synthetic
TNFRI 126-S42 S92H/H95F/R97P/H98A/K161Q polypeptide

<400> SEQUENCE: 79

Asp Ser Val Cys Pro Gln Gly Gln Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala His Glu Asn Phe Leu Pro Ala Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Gln Gln Asn Thr Val Cys
115 120 125

<210> SEQ ID NO 80
<211> LENGTH: 126
<212> TYPE: PRT
<213> ORGANISM: Artificial Sequence
<220> FEATURE:
<223> OTHER INFORMATION: Description of Artificial Sequence: Synthetic
TNFRI 126-S43 S92H/H95F/R97P/H98A/K161N polypeptide

<400> SEQUENCE: 80

Asp Ser Val Cys Pro Gln Gly Gln Tyr Ile His Pro Gln Asn Asn Ser
1 5 10 15

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala His Glu Asn Phe Leu Pro Ala Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

-continued

```
Thr Val His Leu Ser Cys Gln Glu Asn Gln Asn Thr Val Cys
        115                 120                 125


<210> SEQ ID NO 81
<211> LENGTH: 126
<212> TYPE: PRT
<213> ORGANISM: Artificial Sequence
<220> FEATURE:
<223> OTHER INFORMATION: Description of Artificial Sequence: Synthetic
      TNFRI 126-S46 L68V/S92I/H95F/R97P/H98G polypeptide

<400> SEQUENCE: 81

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 82
<211> LENGTH: 126
<212> TYPE: PRT
<213> ORGANISM: Artificial Sequence
<220> FEATURE:
<223> OTHER INFORMATION: Description of Artificial Sequence: Synthetic
      TNFRI 126-S47 L68V/S92M/H95F/R97P/H98G polypeptide

<400> SEQUENCE: 82

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125


<210> SEQ ID NO 83
<211> LENGTH: 126
<212> TYPE: PRT
<213> ORGANISM: Artificial Sequence
<220> FEATURE:
<223> OTHER INFORMATION: Description of Artificial Sequence: Synthetic
```

TNFRI 126-S48 L68V/S92I/E93P/H95F/R97P/H98G polypeptide

<400> SEQUENCE: 83

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Pro Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125
```

<210> SEQ ID NO 84
<211> LENGTH: 126
<212> TYPE: PRT
<213> ORGANISM: Artificial Sequence
<220> FEATURE:
<223> OTHER INFORMATION: Description of Artificial Sequence: Synthetic
TNFRI 126-S49 S92I/E93P/H95F/R97P/H98G/K161Q polypeptide

<400> SEQUENCE: 84

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Pro Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Gln Gln Asn Thr Val Cys
        115                 120                 125
```

<210> SEQ ID NO 85
<211> LENGTH: 126
<212> TYPE: PRT
<213> ORGANISM: Artificial Sequence
<220> FEATURE:
<223> OTHER INFORMATION: Description of Artificial Sequence: Synthetic
TNFRI 126-S50 S92I/E93P/H95F/R97P/H98G/K161N polypeptide

<400> SEQUENCE: 85

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30
```

Pro Gly Pro Gly Gln Asp Thr Asp Cys Arg Glu Cys Glu Ser Gly Ser
35 40 45

Phe Thr Ala Ile Pro Asn Phe Leu Pro Gly Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Asn Gln Asn Thr Val Cys
115 120 125

<210> SEQ ID NO 86
<211> LENGTH: 126
<212> TYPE: PRT
<213> ORGANISM: Artificial Sequence
<220> FEATURE:
<223> OTHER INFORMATION: Description of Artificial Sequence: Synthetic
TNFRI 126-S53 L68V/S92I/H95F/R97P/H98A/K161Q polypeptide

<400> SEQUENCE: 86

Asp Ser Val Cys Pro Gln Gly Gln Tyr Ile His Pro Gln Asn Asn Ser
1 5 10 15

Ile Cys Cys Thr Lys Cys His Lys Gly Thr Tyr Val Tyr Asn Asp Cys
20 25 30

Pro Gly Pro Gly Gln Asp Thr Asp Cys Arg Glu Cys Glu Ser Gly Ser
35 40 45

Phe Thr Ala Ile Glu Asn Phe Leu Pro Ala Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Gln Gln Asn Thr Val Cys
115 120 125

<210> SEQ ID NO 87
<211> LENGTH: 126
<212> TYPE: PRT
<213> ORGANISM: Artificial Sequence
<220> FEATURE:
<223> OTHER INFORMATION: Description of Artificial Sequence: Synthetic
TNFRI 126-S54 L68V/S92I/H95F/R97P/H98A/K161N polypeptide

<400> SEQUENCE: 87

Asp Ser Val Cys Pro Gln Gly Gln Tyr Ile His Pro Gln Asn Asn Ser
1 5 10 15

Ile Cys Cys Thr Lys Cys His Lys Gly Thr Tyr Val Tyr Asn Asp Cys
20 25 30

Pro Gly Pro Gly Gln Asp Thr Asp Cys Arg Glu Cys Glu Ser Gly Ser
35 40 45

Phe Thr Ala Ile Glu Asn Phe Leu Pro Ala Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Asn Gln Asn Thr Val Cys
115 120 125

<210> SEQ ID NO 88
<211> LENGTH: 126
<212> TYPE: PRT
<213> ORGANISM: Artificial Sequence
<220> FEATURE:
<223> OTHER INFORMATION: Description of Artificial Sequence: Synthetic
TNFRI 126-S56 L68V/S92M/H95F/R97P/H98A/K161Q polypeptide

<400> SEQUENCE: 88

Asp Ser Val Cys Pro Gln Gly Gln Tyr Ile His Pro Gln Asn Asn Ser
1 5 10 15

Ile Cys Cys Thr Lys Cys His Lys Gly Thr Tyr Val Tyr Asn Asp Cys
20 25 30

Pro Gly Pro Gly Gln Asp Thr Asp Cys Arg Glu Cys Glu Ser Gly Ser
35 40 45

Phe Thr Ala Met Glu Asn Phe Leu Pro Ala Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Gln Gln Asn Thr Val Cys
115 120 125

<210> SEQ ID NO 89
<211> LENGTH: 126
<212> TYPE: PRT
<213> ORGANISM: Artificial Sequence
<220> FEATURE:
<223> OTHER INFORMATION: Description of Artificial Sequence: Synthetic
TNFRI 126-S57 L68V/S92M/H95F/R97P/H98A/K161N polypeptide

<400> SEQUENCE: 89

Asp Ser Val Cys Pro Gln Gly Gln Tyr Ile His Pro Gln Asn Asn Ser
1 5 10 15

Ile Cys Cys Thr Lys Cys His Lys Gly Thr Tyr Val Tyr Asn Asp Cys
20 25 30

Pro Gly Pro Gly Gln Asp Thr Asp Cys Arg Glu Cys Glu Ser Gly Ser
35 40 45

Phe Thr Ala Met Glu Asn Phe Leu Pro Ala Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Asn Gln Asn Thr Val Cys
115 120 125

<210> SEQ ID NO 90
<211> LENGTH: 126
<212> TYPE: PRT
<213> ORGANISM: Artificial Sequence
<220> FEATURE:
<223> OTHER INFORMATION: Description of Artificial Sequence: Synthetic
TNFRI 126-S59 L68V/S92H/H95F/R97P/H98A/K161Q polypeptide

<400> SEQUENCE: 90

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala His Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Gln Gln Asn Thr Val Cys
        115                 120                 125
```

<210> SEQ ID NO 91
<211> LENGTH: 126
<212> TYPE: PRT
<213> ORGANISM: Artificial Sequence
<220> FEATURE:
<223> OTHER INFORMATION: Description of Artificial Sequence: Synthetic
TNFRI 126-S60 L68V/S92H/H95F/R97P/H98A/K161N polypeptide

<400> SEQUENCE: 91

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala His Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Asn Gln Asn Thr Val Cys
        115                 120                 125
```

<210> SEQ ID NO 92
<211> LENGTH: 126
<212> TYPE: PRT
<213> ORGANISM: Artificial Sequence
<220> FEATURE:
<223> OTHER INFORMATION: Description of Artificial Sequence: Synthetic
TNFRI 126-S62 L68V/S92I/H95F/R97P/H98G/K161Q polypeptide

<400> SEQUENCE: 92

Asp Ser Val Cys Pro Gln Gly Gln Tyr Ile His Pro Gln Asn Asn Ser
1 5 10 15

Ile Cys Cys Thr Lys Cys His Lys Gly Thr Tyr Val Tyr Asn Asp Cys
20 25 30

Pro Gly Pro Gly Gln Asp Thr Asp Cys Arg Glu Cys Glu Ser Gly Ser
35 40 45

Phe Thr Ala Ile Glu Asn Phe Leu Pro Gly Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys
115 120 125

<210> SEQ ID NO 93
<211> LENGTH: 126
<212> TYPE: PRT
<213> ORGANISM: Artificial Sequence
<220> FEATURE:
<223> OTHER INFORMATION: Description of Artificial Sequence: Synthetic
TNFRI 171-S63 L68V/S92M/H95F/R97P/H98G/K161N polypeptide

<400> SEQUENCE: 93

Asp Ser Val Cys Pro Gln Gly Gln Tyr Ile His Pro Gln Asn Asn Ser
1 5 10 15

Ile Cys Cys Thr Lys Cys His Lys Gly Thr Tyr Val Tyr Asn Asp Cys
20 25 30

Pro Gly Pro Gly Gln Asp Thr Asp Cys Arg Glu Cys Glu Ser Gly Ser
35 40 45

Phe Thr Ala Met Glu Asn Phe Leu Pro Gly Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Asn Gln Asn Thr Val Cys
115 120 125

<210> SEQ ID NO 94
<211> LENGTH: 105
<212> TYPE: PRT
<213> ORGANISM: Artificial Sequence
<220> FEATURE:
<223> OTHER INFORMATION: Description of Artificial Sequence: Synthetic
TNFRI105-S31 L68V/S92I/H95F/R97P/H98A polypeptide

<400> SEQUENCE: 94

Asp Ser Val Cys Pro Gln Gly Gln Tyr Ile His Pro Gln Asn Asn Ser
1 5 10 15

Ile Cys Cys Thr Lys Cys His Lys Gly Thr Tyr Val Tyr Asn Asp Cys
20 25 30

Pro Gly Pro Gly Gln Asp Thr Asp Cys Arg Glu Cys Glu Ser Gly Ser
35 40 45

```
Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105


<210> SEQ ID NO 95
<211> LENGTH: 105
<212> TYPE: PRT
<213> ORGANISM: Artificial Sequence
<220> FEATURE:
<223> OTHER INFORMATION: Description of Artificial Sequence: Synthetic
      TNFRI 105-S36 L68V/S92M/H95F/R97P/H98A polypeptide

<400> SEQUENCE: 95

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105


<210> SEQ ID NO 96
<211> LENGTH: 105
<212> TYPE: PRT
<213> ORGANISM: Artificial Sequence
<220> FEATURE:
<223> OTHER INFORMATION: Description of Artificial Sequence: Synthetic
      TNFRI 105-S41 L68V/S92H/H95F/R97P/H98A polypeptide

<400> SEQUENCE: 96

Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala His Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105


<210> SEQ ID NO 97
<211> LENGTH: 105
<212> TYPE: PRT
```

<213> ORGANISM: Artificial Sequence
<220> FEATURE:
<223> OTHER INFORMATION: Description of Artificial Sequence: Synthetic
TNFRI 105-S46 L68V/S92I/H95F/R97P/H98G polypeptide

<400> SEQUENCE: 97

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105
```

<210> SEQ ID NO 98
<211> LENGTH: 105
<212> TYPE: PRT
<213> ORGANISM: Artificial Sequence
<220> FEATURE:
<223> OTHER INFORMATION: Description of Artificial Sequence: Synthetic
TNFRI 105-S47 L68V/S92M/H95F/R97P/H98G polypeptide

<400> SEQUENCE: 98

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105
```

<210> SEQ ID NO 99
<211> LENGTH: 105
<212> TYPE: PRT
<213> ORGANISM: Artificial Sequence
<220> FEATURE:
<223> OTHER INFORMATION: Description of Artificial Sequence: Synthetic
TNFRI 105-S48 L68V/S92I/E93P/H95F/R97P/H98G polypeptide

<400> SEQUENCE: 99

```
Asp Ser Val Cys Pro Gln Gly Gln Tyr Ile His Pro Gln Asn Asn Ser
1               5                   10                  15

Ile Cys Cys Thr Lys Cys His Lys Gly Thr Tyr Val Tyr Asn Asp Cys
            20                  25                  30

Pro Gly Pro Gly Gln Asp Thr Asp Cys Arg Glu Cys Glu Ser Gly Ser
        35                  40                  45
```

```
Phe Thr Ala Ile Pro Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105


<210> SEQ ID NO 100
<211> LENGTH: 321
<212> TYPE: DNA
<213> ORGANISM: Artificial Sequence
<220> FEATURE:
<223> OTHER INFORMATION: Description of Artificial Sequence: Synthetic
      Met-TNFRI105 polynucleotide (for bacterial expression)

<400> SEQUENCE: 100

atggatagcg tgtgcccgca gggtaagtat attcatccgc aaaataactc tatctgttgc     60

acaaagtgtc acaaagggac gtacctgtat aatgactgtc cggggccggg tcaggatacc    120

gactgccgcg agtgcgagag tgggtcattt acagcgagtg agaatcatct gcgccactgc    180

ctgagctgtt ctaagtgtcg taaagagatg ggccaagttg aaatttcttc atgtacggta    240

gaccgcgata cggtatgtgg ttgccgtaaa aaccagtatc gccattattg gtcagaaaac    300

ctgttccagt gttttaatta a                                              321


<210> SEQ ID NO 101
<211> LENGTH: 384
<212> TYPE: DNA
<213> ORGANISM: Artificial Sequence
<220> FEATURE:
<223> OTHER INFORMATION: Description of Artificial Sequence: Synthetic
      Met-TNFRI126 polynucleotide (for bacterial expression)

<400> SEQUENCE: 101

atggatagcg tgtgcccgca gggtaagtat attcatccgc aaaataactc tatctgttgc     60

acaaagtgtc acaaagggac gtacctgtat aatgactgtc cggggccggg tcaggatacc    120

gactgccgcg agtgcgagag tgggtcattt acagcgagtg agaatcatct gcgccactgc    180

ctgagctgtt ctaagtgtcg taaagagatg ggccaagttg aaatttcttc atgtacggta    240

gaccgcgata cggtatgtgg ttgccgtaaa aaccagtatc gccattattg gtcagaaaac    300

ctgttccagt gttttaattg ctccctgtgt ctgaacggca ctgtgcatct gtcctgtcag    360

gagaagcaga atacagtttg ttaa                                           384


<210> SEQ ID NO 102
<211> LENGTH: 519
<212> TYPE: DNA
<213> ORGANISM: Artificial Sequence
<220> FEATURE:
<223> OTHER INFORMATION: Description of Artificial Sequence: Synthetic
      Met-TNFRI171 polynucleotide (for bacterial expression)

<400> SEQUENCE: 102

atggatagcg tgtgcccgca gggtaagtat attcatccgc aaaataactc tatctgttgc     60

acaaagtgtc acaaagggac gtacctgtat aatgactgtc cggggccggg tcaggatacc    120

gactgccgcg agtgcgagag tgggtcattt acagcgagtg agaatcatct gcgccactgc    180

ctgagctgtt ctaagtgtcg taaagagatg ggccaagttg aaatttcttc atgtacggta    240

gaccgcgata cggtatgtgg ttgccgtaaa aaccagtatc gccattattg gtcagaaaac    300
```

```
ctgttccagt gttttaattg ctccctgtgt ctgaacggca ctgtgcatct gtcctgtcag    360

gagaagcaga atacagtttg tacctgccat gcaggtttct ttctaagaga aaacgagtgt    420

gtctcctgta gtaactgtaa gaaaagcctg gagtgcacga agttgtgcct accccagatt    480

gagaatgtta agggcactga ggactcaggc accacataa                           519


<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103

acatatggat agcgtgtgcc cgc                                             23


<210> SEQ ID NO 104
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104

taagcttatt aattaaaaca ctggaac                                         27


<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105

acatatggat agcgtgtgcc cgc                                             23


<210> SEQ ID NO 106
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106

cggatcctta acaaactgta ttctgcttc                                       29


<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107

acatatggat agcgtgtgcc cgc                                             23


<210> SEQ ID NO 108
<211> LENGTH: 28
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 108
cggatcctta tgtggtgcct gagtcctc 28

<210> SEQ ID NO 109
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gagtgggtca tttacagcga ttccgaattt tctgccggcg tgcctgagct gttctaag 58

<210> SEQ ID NO 110
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
cttagaacag ctcaggcacg ccggcagaaa attcggaatc gctgtaaatg acccactc 58

<210> SEQ ID NO 111
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
catttacagc gagtgagaat tttctgcgcg cgtgcctgag ctgttctaag 50

<210> SEQ ID NO 112
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cttagaacag ctcaggcacg cgcgcagaaa attctcactc gctgtaaatg 50

<210> SEQ ID NO 113
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gagtgagaat tttctgccgg cgtgcctgag ctgt 34

<210> SEQ ID NO 114
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
acagctcagg cacgccggca gaaaattctc actc 34

<210> SEQ ID NO 115
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
gtcatttaca gcgattgaga attttctgcc ggc 33

<210> SEQ ID NO 116
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
gccggcagaa aattctcaat cgctgtaaat gac 33

<210> SEQ ID NO 117
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
gggtcattta cagcggggga gaattttctg c 31

<210> SEQ ID NO 118
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
gcagaaaatt ctcccccgct gtaaatgacc c 31

<210> SEQ ID NO 119
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
gggtcattta cagcggcgga gaattttctg c 31

<210> SEQ ID NO 120
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
gcagaaaatt ctccgccgct gtaaatgacc c 31

<210> SEQ ID NO 121
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
gggtcattta cagcggttga gaattttctg c 31

<210> SEQ ID NO 122
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
gcagaaaatt ctcaaccgct gtaaatgacc c 31

<210> SEQ ID NO 123
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
gggtcattta cagcgctgga gaattttctg c 31

<210> SEQ ID NO 124
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
gcagaaaatt ctccagcgct gtaaatgacc c 31

<210> SEQ ID NO 125
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 125
gggtcattta cagcgccgga gaattttctg c 31

<210> SEQ ID NO 126
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 126
gcagaaaatt ctccggcgct gtaaatgacc c 31

<210> SEQ ID NO 127
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 127
gggtcattta cagcgtttga gaattttctg c 31

<210> SEQ ID NO 128
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 128
gcagaaaatt ctcaaacgct gtaaatgacc c 31

<210> SEQ ID NO 129
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 129
gggtcattta cagcgatgga gaattttctg c 31

<210> SEQ ID NO 130
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 130
gcagaaaatt ctccatcgct gtaaatgacc c 31

<210> SEQ ID NO 131
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 131
gggtcattta cagcgtggga gaattttctg c 31

<210> SEQ ID NO 132
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 132
gcagaaaatt ctcccacgct gtaaatgacc c 31

-continued

<210> SEQ ID NO 133
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 133
gggtcattta cagcgtgcga gaattttctg c 31

<210> SEQ ID NO 134
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 134
gcagaaaatt ctcgcacgct gtaaatgacc c 31

<210> SEQ ID NO 135
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 135
gggtcattta cagcgaatga gaattttctg c 31

<210> SEQ ID NO 136
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 136
gcagaaaatt ctcattcgct gtaaatgacc c 31

<210> SEQ ID NO 137
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 137
gggtcattta cagcgcagga gaattttctg c 31

<210> SEQ ID NO 138
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 138
gcagaaaatt ctcctgcgct gtaaatgacc c 31

<210> SEQ ID NO 139
<211> LENGTH: 31

<212> TYPE: DNA
<213> ORGANISM: Artificial Sequence
<220> FEATURE:
<223> OTHER INFORMATION: Description of Artificial Sequence: Synthetic primer

<400> SEQUENCE: 139
gggtcattta cagcgacaga gaattttctg c 31

<210> SEQ ID NO 140
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 140
gcagaaaatt ctctgtcgct gtaaatgacc c 31

<210> SEQ ID NO 141
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 141
gggtcattta cagcgtacga gaattttctg c 31

<210> SEQ ID NO 142
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 142
gcagaaaatt ctcgtacgct gtaaatgacc c 31

<210> SEQ ID NO 143
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 143
gggtcattta cagcgaagga gaattttctg c 31

<210> SEQ ID NO 144
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 144
gcagaaaatt ctccttcgct gtaaatgacc c 31

<210> SEQ ID NO 145
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 145
gggtcattta cagcgcgcga gaattttctg c 31

<210> SEQ ID NO 146
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 146
gcagaaaatt ctcgcgcgct gtaaatgacc c 31

<210> SEQ ID NO 147
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
gggtcattta cagcgcatga gaattttctg c 31

<210> SEQ ID NO 148
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 148
gcagaaaatt ctcatgcgct gtaaatgacc c 31

<210> SEQ ID NO 149
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 149
gggtcattta cagcggatga gaattttctg c 31

<210> SEQ ID NO 150
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 150
gcagaaaatt ctcatccgct gtaaatgacc c 31

<210> SEQ ID NO 151
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
gggtcattta cagcggaaga gaattttctg c 31

<210> SEQ ID NO 152
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
gcagaaaatt ctcttccgct gtaaatgacc c 31

<210> SEQ ID NO 153
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 153
gagaattttc tgccggggtg cctgagctgt tcta 34

<210> SEQ ID NO 154
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 154
tagaacagct caggcacccc ggcagaaaat tctc 34

<210> SEQ ID NO 155
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 155
gagaattttc tgccggggtg cctgagctgt tcta 34

<210> SEQ ID NO 156
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 156
tagaacagct caggcacccc ggcagaaaat tctc 34

<210> SEQ ID NO 157
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 157
gattccgaat tttctgctgg cgtgcctgag ctgt 34

<210> SEQ ID NO 158
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 158
acagctcagg cacgccagca gaaaattcgg aatc 34

<210> SEQ ID NO 159
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 159
gattccgaat tttctgattg cgtgcctgag ctgt 34

<210> SEQ ID NO 160
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 160
acagctcagg cacgcaatca gaaaattcgg aatc 34

<210> SEQ ID NO 161
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
gattccgaat tttctgtttg cgtgcctgag ctgt 34

<210> SEQ ID NO 162
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 162
acagctcagg cacgcaaaca gaaaattcgg aatc 34

<210> SEQ ID NO 163
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
tccgaatttt ctgccggggt gcctgagctg ttc 33

<210> SEQ ID NO 164
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 164
gaacagctca ggcaccccgg cagaaaattc gga 33

<210> SEQ ID NO 165
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 165
agcgattccg aattttctgc tggggtgcct gagctgttct aag 43

<210> SEQ ID NO 166
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
cttagaacag ctcaggcacc ccagcagaaa attcggaatc gct 43

<210> SEQ ID NO 167
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 167
agcgattccg aattttctga ttgggtgcct gagctgttct aag 43

<210> SEQ ID NO 168
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 168
cttagaacag ctcaggcacc caatcagaaa attcggaatc gct 43

<210> SEQ ID NO 169
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 169
agcgattccg aattttctgt ttgggtgcct gagctgttct aag 43

-continued

<210> SEQ ID NO 170
<211> LENGTH: 43
<212> TYPE: DNA
<213> ORGANISM: Artificial Sequence
<220> FEATURE:
<223> OTHER INFORMATION: Description of Artificial Sequence: Synthetic
primer

<400> SEQUENCE: 170
cttagaacag ctcaggcacc caaacagaaa attcggaatc gct 43

<210> SEQ ID NO 171
<211> LENGTH: 5
<212> TYPE: PRT
<213> ORGANISM: Unknown
<220> FEATURE:
<223> OTHER INFORMATION: Description of Unknown: Chymotrypsin
cleavage site peptide

<400> SEQUENCE: 171

Phe Tyr Trp Met Leu
1 5

<210> SEQ ID NO 172
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 172
ccccggggcg atgacgatga caaagatagc gtgtgcccg 39

<210> SEQ ID NO 173
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 173
taagcttatt acagggagca attaaaacac tgg 33

<210> SEQ ID NO 174
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 174
atagcgtgtg cccgcagggt cagtatattc atcc 34

<210> SEQ ID NO 175
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 175
ggatgaatat actgaccctg cgggcacacg ctat 34

<210> SEQ ID NO 176
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 176
gtgtgcccgc agggtaacta tattcatccg caaa 34

<210> SEQ ID NO 177
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 177
tttgcggatg aatatagtta ccctgcgggc acac 34

<210> SEQ ID NO 178
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 178
gcccgcaggg taagattatt catccgcaaa at 32

<210> SEQ ID NO 179
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 179
attttgcgga tgaataatct taccctgcgg gc 32

<210> SEQ ID NO 180
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 180
gtgcccgcag ggtaagcata ttcatccgca aaat 34

<210> SEQ ID NO 181
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 181
attttgcgga tgaatatgct taccctgcgg gcac 34

<210> SEQ ID NO 182
<211> LENGTH: 34

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
cgcagggtaa gtatattcat gcgcaaaata actc 34

<210> SEQ ID NO 183
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
gagttatttt gcgcatgaat atacttaccc tgcg 34

<210> SEQ ID NO 184
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
gggtaagtat attcatagcc aaaataactc tatc 34

<210> SEQ ID NO 185
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
gatagagtta ttttggctat gaatatactt accc 34

<210> SEQ ID NO 186
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
taactctatc tgttgcacac agtgtcacaa aggg 34

<210> SEQ ID NO 187
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ccctttgtga cactgtgtgc aacagataga gtta 34

<210> SEQ ID NO 188
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 188
ctctatctgt tgcacaaact gtcacaaagg gac 33

<210> SEQ ID NO 189
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 189
gtccctttgt gacagtttgt gcaacagata gag 33

<210> SEQ ID NO 190
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 190
gcacaaagtg tcaccagggg acgtacctgt at 32

<210> SEQ ID NO 191
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 191
atacaggtac gtcccctggt gacactttgt gc 32

<210> SEQ ID NO 192
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 192
gcacaaagtg tcacaacggg acgtacctgt ata 33

<210> SEQ ID NO 193
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 193
tatacaggta cgtcccgttg tgacactttg tgc 33

<210> SEQ ID NO 194
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 194
gtcacaaagg gacgattctg tataatgact gtc 33

<210> SEQ ID NO 195
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 195
gacagtcatt atacagaatc gtccctttgt gac 33

<210> SEQ ID NO 196
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 196
gtgtcacaaa gggacgcatc tgtataatga ctg 33

<210> SEQ ID NO 197
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 197
cagtcattat acagatgcgt ccctttgtga cac 33

<210> SEQ ID NO 198
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 198
cacaaaggga cgtacattta taatgactgt ccgg 34

<210> SEQ ID NO 199
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 199
ccggacagtc attataaatg tacgtccctt tgtg 34

<210> SEQ ID NO 200
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 200
gtgtcacaaa gggacgcatc tgtataatga ctg 33

<210> SEQ ID NO 201
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 201
cagtcattat acagatgcgt ccctttgtga cac 33

<210> SEQ ID NO 202
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 202
caaagggacg tacctgatta atgactgtcc gggg 34

<210> SEQ ID NO 203
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 203
ccccggacag tcattaatca ggtacgtccc tttg 34

<210> SEQ ID NO 204
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 204
caaagggacg tacctgcata atgactgtcc ggg 33

<210> SEQ ID NO 205
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 205
cccggacagt cattatgcag gtacgtccct ttg 33

<210> SEQ ID NO 206
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 206
gggacgtacc tgtataataa ctgtccgggg c 31

<210> SEQ ID NO 207
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 207
gccccggaca gttattatac aggtacgtcc c 31

<210> SEQ ID NO 208
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 208
gggacgtacc tgtataatca gtgtccgggg cc 32

<210> SEQ ID NO 209
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 209
ggccccggac actgattata caggtacgtc cc 32

<210> SEQ ID NO 210
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 210
ggggccgggt cagaacaccg actgccgcg 29

<210> SEQ ID NO 211
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 211
cgcggcagtc ggtgttctga cccggccc 28

<210> SEQ ID NO 212
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 212
gggccgggtc agcagaccga ctgccgc 27

<210> SEQ ID NO 213
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 213
gcggcagtcg gtctgctgac ccggccc 27

<210> SEQ ID NO 214
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 214
gggtcaggat accaactgcc gcgagtg 27

<210> SEQ ID NO 215
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 215
cactcgcggc agttggtatc ctgaccc 27

<210> SEQ ID NO 216
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 216
gggtcaggat acccagtgcc gcgagtgcg 29

<210> SEQ ID NO 217
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 217
cgcactcgcg gcactgggta tcctgaccc 29

<210> SEQ ID NO 218
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 218
ggataccgac tgccatgagt gcgagagtgg g 31

<210> SEQ ID NO 219

<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 219
cccactctcg cactcatggc agtcggtatc c 31

<210> SEQ ID NO 220
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 220
ggataccgac tgccaggagt gcgagagtgg 30

<210> SEQ ID NO 221
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 221
ccactctcgc actcctggca gtcggtatcc 30

<210> SEQ ID NO 222
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 222
accgactgcc gccagtgcga gagtg 25

<210> SEQ ID NO 223
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 223
cactctcgca ctggcggcag tcggt 25

<210> SEQ ID NO 224
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 224
ataccgactg ccgcaactgc gagagtgggt c 31

<210> SEQ ID NO 225
<211> LENGTH: 31
<212> TYPE: DNA

<213> ORGANISM: Artificial Sequence
<220> FEATURE:
<223> OTHER INFORMATION: Description of Artificial Sequence: Synthetic
primer

<400> SEQUENCE: 225
gacccactct cgcagttgcg gcagtcggta t 31

<210> SEQ ID NO 226
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 226
ctgccgcgag tgccagagtg ggtcatt 27

<210> SEQ ID NO 227
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 227
aatgacccac tctggcactc gcggcag 27

<210> SEQ ID NO 228
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 228
gactgccgcg agtgcaacag tgggtcattt acag 34

<210> SEQ ID NO 229
<211> LENGTH: 35
<212> TYPE: DNA
<213> ORGANISM: Artificial Sequence
<220> FEATURE:
<223> OTHER INFORMATION: Description of Artificial Sequence: Synthetic
primer

<400> SEQUENCE: 229
ctgtaaatga cccactgttg cactcgcggc agtcg 35

<210> SEQ ID NO 230
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 230
gtgcgagagt gggtcaatta cagcgagtga g 31

<210> SEQ ID NO 231
<211> LENGTH: 31
<212> TYPE: DNA
<213> ORGANISM: Artificial Sequence
<220> FEATURE:

<223> OTHER INFORMATION: Description of Artificial Sequence: Synthetic primer

<400> SEQUENCE: 231
ctcactcgct gtaattgacc cactctcgca c 31

<210> SEQ ID NO 232
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 232
cgagtgcgag agtgggtcag tgacagcgag tg 32

<210> SEQ ID NO 233
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 233
cactcgctgt cactgaccca ctctcgcact cg 32

<210> SEQ ID NO 234
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 234
gtgggtcatt tacagcgagt cagaatcatc tgcg 34

<210> SEQ ID NO 235
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 235
cgcagatgat tctgactcgc tgtaaatgac ccac 34

<210> SEQ ID NO 236
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 236
gtcatttaca gcgagtaaca atcatctgcg ccac 34

<210> SEQ ID NO 237
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 237
gtggcgcaga tgattgttac tcgctgtaaa tgac 34

<210> SEQ ID NO 238
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 238
gcgagtgaga atcatattcg ccactgcctg agc 33

<210> SEQ ID NO 239
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 239
gctcaggcag tggcgaatat gattctcact cgc 33

<210> SEQ ID NO 240
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 240
tacagcgagt gagaatcatg tgcgccactg c 31

<210> SEQ ID NO 241
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 241
gcagtggcgc acatgattct cactcgctgt a 31

<210> SEQ ID NO 242
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 242
gagtgagaat catctgcatc actgcctgag ctg 33

<210> SEQ ID NO 243
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 243
cagctcaggc agtgatgcag atgattctca ctc 33

<210> SEQ ID NO 244
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 244
gagtgagaat catctgcagc actgcctgag ctg 33

<210> SEQ ID NO 245
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 245
cagctcaggc agtgctgcag atgattctca ctc 33

<210> SEQ ID NO 246
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 246
catctgcgcc actgcattag ctgttctaag tgtc 34

<210> SEQ ID NO 247
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 247
gacacttaga acagctaatg cagtggcgca gatg 34

<210> SEQ ID NO 248
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 248
catctgcgcc actgcgtgag ctgttctaag 30

<210> SEQ ID NO 249
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 249
cttagaacag ctcacgcagt ggcgcagatg 30

<210> SEQ ID NO 250
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 250
cgccactgcc tgagctgttc tcagtgtcgt aaa 33

<210> SEQ ID NO 251
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 251
tttacgacac tgagaacagc tcaggcagtg gcg 33

<210> SEQ ID NO 252
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 252
cactgcctga gctgttctaa ctgtcgtaaa gag 33

<210> SEQ ID NO 253
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 253
ctctttacga cagttagaac agctcaggca gtg 33

<210> SEQ ID NO 254
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 254
gctgttctaa gtgtcataaa gagatgggcc aag 33

<210> SEQ ID NO 255
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 255
cttggcccat ctctttatga cacttagaac agc 33

<210> SEQ ID NO 256
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 256
gctgttctaa gtgtcagaaa gagatgggcc aag 33

<210> SEQ ID NO 257
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 257
cttggcccat ctctttctga cacttagaac agc 33

<210> SEQ ID NO 258
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 258
gttctaagtg tcgtcaggag atgggccaag ttg 33

<210> SEQ ID NO 259
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 259
caacttggcc catctcctga cgacacttag aac 33

<210> SEQ ID NO 260
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 260
gttctaagtg tcgtaacgag atgggccaag ttg 33

<210> SEQ ID NO 261
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 261
caacttggcc catctcgtta cgacacttag aac 33

<210> SEQ ID NO 262
<211> LENGTH: 33

<212> TYPE: DNA
<213> ORGANISM: Artificial Sequence
<220> FEATURE:
<223> OTHER INFORMATION: Description of Artificial Sequence: Synthetic primer

<400> SEQUENCE: 262
gctgttctaa gtgtcgtaaa cagatgggcc aag 33

<210> SEQ ID NO 263
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 263
cttggcccat ctgtttacga cacttagaac agc 33

<210> SEQ ID NO 264
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 264
gttctaagtg tcgtaaaaac atgggccaag ttg 33

<210> SEQ ID NO 265
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 265
caacttggcc catgttttta cgacacttag aac 33

<210> SEQ ID NO 266
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 266
ctaagtgtcg taaagagatt ggccaagttg aaat 34

<210> SEQ ID NO 267
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 267
atttcaactt ggccaatctc tttacgacac ttag 34

<210> SEQ ID NO 268
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 268
ctaagtgtcg taaagaggtg ggccaagttg aaat 34

<210> SEQ ID NO 269
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 269
atttcaactt ggcccacctc tttacgacac ttag 34

<210> SEQ ID NO 270
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 270
gagatgggcc aagttcagat ttcttcatgt acgg 34

<210> SEQ ID NO 271
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 271
ccgtacatga agaaatctga acttggccca tctc 34

<210> SEQ ID NO 272
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 272
gagatgggcc aagttaacat ttcttcatgt acgg 34

<210> SEQ ID NO 273
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 273
ccgtacatga agaaatgtta acttggccca tctc 34

<210> SEQ ID NO 274
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 274
tttcttcatg tacggtaaac cgcgatacgg tatg 34

<210> SEQ ID NO 275
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 275
cataccgtat cgcggtttac cgtacatgaa gaaa 34

<210> SEQ ID NO 276
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 276
tttcttcatg tacggtacag cgcgatacgg tatg 34

<210> SEQ ID NO 277
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 277
cataccgtat cgcgctgtac cgtacatgaa gaaa 34

<210> SEQ ID NO 278
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 278
catgtacggt agaccatgat acggtatgtg gttg 34

<210> SEQ ID NO 279
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 279
caaccacata ccgtatcatg gtctaccgta catg 34

<210> SEQ ID NO 280
<211> LENGTH: 34
<212> TYPE: DNA
<213> ORGANISM: Artificial Sequence
<220> FEATURE:
<223> OTHER INFORMATION: Description of Artificial Sequence: Synthetic primer -continued

<400> SEQUENCE: 280
catgtacggt agaccaggat acggtatgtg gttg 34

<210> SEQ ID NO 281
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 281
caaccacata ccgtatcctg gtctaccgta catg 34

<210> SEQ ID NO 282
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 282
gtacggtaga ccgcaacacg gtatgtggtt gcc 33

<210> SEQ ID NO 283
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 283
ggcaaccaca taccgtgttg cggtctaccg tac 33

<210> SEQ ID NO 284
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 284
gtacggtaga ccgccagacg gtatgtggtt gcc 33

<210> SEQ ID NO 285
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 285
ggcaaccaca taccgtctgg cggtctaccg tac 33

<210> SEQ ID NO 286
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 286
cggtatgtgg ttgccataaa aaccagtatc gcc 33

<210> SEQ ID NO 287
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 287
ggcgatactg gtttttatgg caaccacata ccg 33

<210> SEQ ID NO 288
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 288
cggtatgtgg ttgccagaaa aaccagtatc gcc 33

<210> SEQ ID NO 289
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 289
ggcgatactg gtttttctgg caaccacata ccg 33

<210> SEQ ID NO 290
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 290
ggtatgtggt tgccgtcaga accagtatcg cc 32

<210> SEQ ID NO 291
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 291
ggcgatactg gttctgacgg caaccacata cc 32

<210> SEQ ID NO 292
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 292
ggtatgtggt tgccgtaaca accagtatcg cc 32

<210> SEQ ID NO 293
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 293
ggcgatactg gttgttacgg caaccacata cc 32

<210> SEQ ID NO 294
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 294
gttgccgtaa aaaccagatt cgccattatt ggtc 34

<210> SEQ ID NO 295
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 295
gaccaataat ggcgaatctg gtttttacgg caac 34

<210> SEQ ID NO 296
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 296
gttgccgtaa aaaccagcat cgccattatt ggtc 34

<210> SEQ ID NO 297
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 297
gaccaataat ggcgatgctg gtttttacgg caac 34

<210> SEQ ID NO 298
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 298
gccgtaaaaa ccagtatcat cattattggt cag 33

<210> SEQ ID NO 299

<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 299
ctgaccaata atgatgatac tggtttttac ggc 33

<210> SEQ ID NO 300
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 300
gccgtaaaaa ccagtatcag cattattggt cag 33

<210> SEQ ID NO 301
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 301
ctgaccaata atgctgatac tggtttttac ggc 33

<210> SEQ ID NO 302
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 302
ccagtatcgc catatttggt cagaaaacct gttc 34

<210> SEQ ID NO 303
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 303
gaacaggttt tctgaccaaa tatggcgata ctgg 34

<210> SEQ ID NO 304
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 304
ccagtatcgc catcattggt cagaaaacct gttc 34

<210> SEQ ID NO 305
<211> LENGTH: 34
<212> TYPE: DNA

<213> ORGANISM: Artificial Sequence
<220> FEATURE:
<223> OTHER INFORMATION: Description of Artificial Sequence: Synthetic
primer

<400> SEQUENCE: 305
gaacaggttt tctgaccaat gatggcgata ctgg 34

<210> SEQ ID NO 306
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 306
cagtatcgcc attatcattc agaaaacctg ttcc 34

<210> SEQ ID NO 307
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 307
ggaacaggtt ttctgaatga taatggcgat actg 34

<210> SEQ ID NO 308
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 308
cagtatcgcc attatagctc agaaaacctg ttcc 34

<210> SEQ ID NO 309
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 309
ggaacaggtt ttctgagcta taatggcgat actg 34

<210> SEQ ID NO 310
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 310
cgccattatt ggtcacagaa cctgttccag tg 32

<210> SEQ ID NO 311
<211> LENGTH: 32
<212> TYPE: DNA
<213> ORGANISM: Artificial Sequence
<220> FEATURE:

<223> OTHER INFORMATION: Description of Artificial Sequence: Synthetic
primer

<400> SEQUENCE: 311
cactggaaca ggttctgtga ccaataatgg cg 32

<210> SEQ ID NO 312
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 312
cgccattatt ggtcaaacaa cctgttccag tg 32

<210> SEQ ID NO 313
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 313
cactggaaca ggttgtttga ccaataatgg cg 32

<210> SEQ ID NO 314
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 314
attggtcaga aaacattttc cagtgtttta attg 34

<210> SEQ ID NO 315
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 315
caattaaaac actggaaaat gttttctgac caat 34

<210> SEQ ID NO 316
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 316
attggtcaga aaacgtgttc cagtgtttta attg 34

<210> SEQ ID NO 317
<211> LENGTH: 34
<212> TYPE: DNA
<213> ORGANISM: Artificial Sequence
<220> FEATURE:
<223> OTHER INFORMATION: Description of Artificial Sequence: Synthetic
primer -continued

<400> SEQUENCE: 317
caattaaaac actggaacac gttttctgac caat 34

<210> SEQ ID NO 318
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 318
ggtcagaaaa cctgattcag tgttttaatt gctc 34

<210> SEQ ID NO 319
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 319
gagcaattaa aacactgaat caggttttct gacc 34

<210> SEQ ID NO 320
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 320
ggtcagaaaa cctggtgcag tgttttaatt gctc 34

<210> SEQ ID NO 321
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 321
gagcaattaa aacactgcac caggttttct gacc 34

<210> SEQ ID NO 322
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 322
gaaaacctgt tccagtgtat taattgctcc ctg 33

<210> SEQ ID NO 323
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 323
cagggagcaa ttaatacact ggaacaggtt ttc 33

<210> SEQ ID NO 324
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 324
gaaaacctgt tccagtgtgt gaattgctcc ctg 33

<210> SEQ ID NO 325
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 325
cagggagcaa ttcacacact ggaacaggtt ttc 33

<210> SEQ ID NO 326
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 326
aattgctccc tgtgtattaa cggcactgtg catc 34

<210> SEQ ID NO 327
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 327
gatgcacagt gccgttaata cacagggagc aatt 34

<210> SEQ ID NO 328
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 328
ttaattgctc cctgtgtgtg aacggcactg tgca 34

<210> SEQ ID NO 329
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 329
tgcacagtgc cgttcacaca cagggagcaa ttaa 34

<210> SEQ ID NO 330
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 330
gaacggcact gtgcatattt cctgtcagga gaag 34

<210> SEQ ID NO 331
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 331
cttctcctga caggaaatat gcacagtgcc gttc 34

<210> SEQ ID NO 332
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 332
tgaacggcac tgtgcatgtg tcctgtcagg agaa 34

<210> SEQ ID NO 333
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 333
ttctcctgac aggacacatg cacagtgccg ttca 34

<210> SEQ ID NO 334
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 334
gcatctgtcc tgtcagcaga agcagaatac agtt 34

<210> SEQ ID NO 335
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 335
aactgtattc tgcttctgct gacaggacag atgc 34

<210> SEQ ID NO 336
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
gcatctgtcc tgtcagaaca agcagaatac agtt 34

<210> SEQ ID NO 337
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
aactgtattc tgcttgttct gacaggacag atgc 34

<210> SEQ ID NO 338
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
atctgtcctg tcaggagcag cagaatacag tttg 34

<210> SEQ ID NO 339
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
caaactgtat tctgctgctc ctgacaggac agat 34

<210> SEQ ID NO 340
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
ctgtcctgtc aggagaacca gaatacagtt tgta 34

<210> SEQ ID NO 341
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
tacaaactgt attctggttc tcctgacagg acag 34

<210> SEQ ID NO 342
<211> LENGTH: 34

<212> TYPE: DNA
<213> ORGANISM: Artificial Sequence
<220> FEATURE:
<223> OTHER INFORMATION: Description of Artificial Sequence: Synthetic
primer

<400> SEQUENCE: 342
ttgtgcctac cccagattca gaatgttaag ggca 34

<210> SEQ ID NO 343
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 343
tgcccttaac attctgaatc tggggtaggc acaa 34

<210> SEQ ID NO 344
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 344
gtgcctaccc cagattaaca atgttaaggg cact 34

<210> SEQ ID NO 345
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 345
agtgccctta acattgttaa tctggggtag gcac 34

<210> SEQ ID NO 346
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 346
ccccagattg agaatgttca gggcactgag gac 33

<210> SEQ ID NO 347
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 347
gtcctcagtg ccctgaacat tctcaatctg ggg 33

<210> SEQ ID NO 348
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 348
cccagattga gaatgttaac ggcactgagg actc 34

<210> SEQ ID NO 349
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 349
gagtcctcag tgccgttaac attctcaatc tggg 34

<210> SEQ ID NO 350
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 350
ttgagaatgt taagggcact caggactcag gcac 34

<210> SEQ ID NO 351
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 351
gtgcctgagt cctgagtgcc cttaacattc tcaa 34

<210> SEQ ID NO 352
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 352
aatgttaagg gcactaacga ctcaggcacc acat 34

<210> SEQ ID NO 353
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 353
atgtggtgcc tgagtcgtta gtgcccttaa catt 34

<210> SEQ ID NO 354
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 354
gttaagggca ctgagcagtc aggcaccaca taag 34

<210> SEQ ID NO 355
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 355
cttatgtggt gcctgactgc tcagtgccct taac 34

<210> SEQ ID NO 356
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 356
atgttaaggg cactgagaac tcaggcacca cata 34

<210> SEQ ID NO 357
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 357
tatgtggtgc ctgagttctc agtgccctta acat 34

<210> SEQ ID NO 358
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 358
cacaaaggga cgtacgtgta taatgactgt ccg 33

<210> SEQ ID NO 359
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 359
cggacagtca ttatacacgt acgtcccttt gtg 33

<210> SEQ ID NO 360
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 360
atctgtcctg tcaggagcag cagaatacag tttg 34

<210> SEQ ID NO 361
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 361
caaactgtat tctgctgctc ctgacaggac agat 34

<210> SEQ ID NO 362
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 362
ctgtcctgtc aggagaacca gaatacagtt tgta 34

<210> SEQ ID NO 363
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 363
tacaaactgt attctggttc tcctgacagg acag 34

<210> SEQ ID NO 364
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 364
ttgtgcctac cccagattca gaatgttaag ggca 34

<210> SEQ ID NO 365
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 365
tgcccttaac attctgaatc tggggtaggc acaa 34

<210> SEQ ID NO 366
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 366

-continued atgttaaggg cactgagaac tcaggcacca cata 34

<210> SEQ ID NO 367
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 367
tatgtggtgc ctgagttctc agtgccctta acat 34

<210> SEQ ID NO 368
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 368
cacaaaggga cgtacgtgta taatgactgt ccg 33

<210> SEQ ID NO 369
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 369
cggacagtca ttatacacgt acgtcccttt gtg 33

<210> SEQ ID NO 370
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 370
atctgtcctg tcaggagcag cagaatacag tttg 34

<210> SEQ ID NO 371
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 371
caaactgtat tctgctgctc ctgacaggac agat 34

<210> SEQ ID NO 372
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 372
ctgtcctgtc aggagaacca gaatacagtt tgta 34

<210> SEQ ID NO 373
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 373
tacaaactgt attctggttc tcctgacagg acag 34

<210> SEQ ID NO 374
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 374
ttgtgcctac cccagattca gaatgttaag ggca 34

<210> SEQ ID NO 375
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 375
tgcccttaac attctgaatc tggggtaggc acaa 34

<210> SEQ ID NO 376
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 376
atgttaaggg cactgagaac tcaggcacca cata 34

<210> SEQ ID NO 377
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 377
tatgtggtgc ctgagttctc agtgccctta acat 34

<210> SEQ ID NO 378
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 378
cacaaaggga cgtacgtgta taatgactgt ccg 33

<210> SEQ ID NO 379

<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 379
cggacagtca ttatacacgt acgtcccttt gtg 33

<210> SEQ ID NO 380
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 380
atctgtcctg tcaggagcag cagaatacag tttg 34

<210> SEQ ID NO 381
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 381
caaactgtat tctgctgctc ctgacaggac agat 34

<210> SEQ ID NO 382
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 382
ctgtcctgtc aggagaacca gaatacagtt tgta 34

<210> SEQ ID NO 383
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 383
tacaaactgt attctggttc tcctgacagg acag 34

<210> SEQ ID NO 384
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 384
ttgtgcctac cccagattca gaatgttaag ggca 34

<210> SEQ ID NO 385
<211> LENGTH: 34
<212> TYPE: DNA

<213> ORGANISM: Artificial Sequence
<220> FEATURE:
<223> OTHER INFORMATION: Description of Artificial Sequence: Synthetic
primer

<400> SEQUENCE: 385
tgcccttaac attctgaatc tggggtaggc acaa 34

<210> SEQ ID NO 386
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 386
atgttaaggg cactgagaac tcaggcacca cata 34

<210> SEQ ID NO 387
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 387
tatgtggtgc ctgagttctc agtgccctta acat 34

<210> SEQ ID NO 388
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 388
gagaattttc tgccggggtg cctgagctgt tcta 34

<210> SEQ ID NO 389
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 389
tagaacagct caggcacccc ggcagaaaat tctc 34

<210> SEQ ID NO 390
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 390
gagaattttc tgccggggtg cctgagctgt tcta 34

<210> SEQ ID NO 391
<211> LENGTH: 34
<212> TYPE: DNA
<213> ORGANISM: Artificial Sequence
<220> FEATURE:

<223> OTHER INFORMATION: Description of Artificial Sequence: Synthetic primer

<400> SEQUENCE: 391
tagaacagct caggcacccc ggcagaaaat tctc 34

<210> SEQ ID NO 392
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 392
cacaaaggga cgtacgtgta taatgactgt ccg 33

<210> SEQ ID NO 393
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 393
cggacagtca ttatacacgt acgtcccttt gtg 33

<210> SEQ ID NO 394
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 394
atctgtcctg tcaggagcag cagaatacag tttg 34

<210> SEQ ID NO 395
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 395
caaactgtat tctgctgctc ctgacaggac agat 34

<210> SEQ ID NO 396
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 396
ctgtcctgtc aggagaacca gaatacagtt tgta 34

<210> SEQ ID NO 397
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 397
tacaaactgt attctggttc tcctgacagg acag 34

<210> SEQ ID NO 398
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 398
ttgtgcctac cccagattca gaatgttaag ggca 34

<210> SEQ ID NO 399
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 399
tgcccttaac attctgaatc tggggtaggc acaa 34

<210> SEQ ID NO 400
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 400
atgttaaggg cactgagaac tcaggcacca cata 34

<210> SEQ ID NO 401
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 401
tatgtggtgc ctgagttctc agtgccctta acat 34

<210> SEQ ID NO 402
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 402
atctgtcctg tcaggagcag cagaatacag tttg 34

<210> SEQ ID NO 403
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 403
caaactgtat tctgctgctc ctgacaggac agat 34

<210> SEQ ID NO 404
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 404
ctgtcctgtc aggagaacca gaatacagtt tgta 34

<210> SEQ ID NO 405
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 405
tacaaactgt attctggttc tcctgacagg acag 34

<210> SEQ ID NO 406
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 406
atgttaaggg cactgagaac tcaggcacca cata 34

<210> SEQ ID NO 407
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 407
tatgtggtgc ctgagttctc agtgccctta acat 34

<210> SEQ ID NO 408
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 408
atctgtcctg tcaggagcag cagaatacag tttg 34

<210> SEQ ID NO 409
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 409
caaactgtat tctgctgctc ctgacaggac agat 34

<210> SEQ ID NO 410
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 410
ctgtcctgtc aggagaacca gaatacagtt tgta 34

<210> SEQ ID NO 411
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 411
tacaaactgt attctggttc tcctgacagg acag 34

<210> SEQ ID NO 412
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 412
atgttaaggg cactgagaac tcaggcacca cata 34

<210> SEQ ID NO 413
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 413
tatgtggtgc ctgagttctc agtgccctta acat 34

<210> SEQ ID NO 414
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 414
atctgtcctg tcaggagcag cagaatacag tttg 34

<210> SEQ ID NO 415
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 415
caaactgtat tctgctgctc ctgacaggac agat 34

<210> SEQ ID NO 416
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 416
ctgtcctgtc aggagaacca gaatacagtt tgta 34

<210> SEQ ID NO 417
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 417
tacaaactgt attctggttc tcctgacagg acag 34

<210> SEQ ID NO 418
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 418
atgttaaggg cactgagaac tcaggcacca cata 34

<210> SEQ ID NO 419
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 419
tatgtggtgc ctgagttctc agtgccctta acat 34

<210> SEQ ID NO 420
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 420
atctgtcctg tcaggagcag cagaatacag tttg 34

<210> SEQ ID NO 421
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 421
caaactgtat tctgctgctc ctgacaggac agat 34

<210> SEQ ID NO 422
<211> LENGTH: 34

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422

ctgtcctgtc aggagaacca gaatacagtt tgta                              34


<210> SEQ ID NO 423
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423

tacaaactgt attctggttc tcctgacagg acag                              34
```